(12) United States Patent
Vakalopoulos et al.

(10) Patent No.: US 8,772,498 B2
(45) Date of Patent: *Jul. 8, 2014

(54) ALKYLAMINE-SUBSTITUTED DICYANOPYRIDINE AND AMINO ACID ESTER PRODRUGS THEREOF

(71) Applicant: Bayer Intellectual Property GmbH, Monheim (DE)

(72) Inventors: Alexandros Vakalopoulos, Hilden (DE); Daniel Meibom, Leverkusen (DE); Barbara Albrecht-Küpper, Wüfrath (DE); Katja Zimmermann, Düsseldorf (DE); Jörg Keldenich, Wuppertal (DE); Hans-Georg Lerchen, Leverkusen (DE); Peter Nell, Woodside, CA (US); Frank Süßmeier, Munich (DE); Ursula Krenz, Leichlingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/801,484

(22) Filed: Mar. 13, 2013

(65) Prior Publication Data

US 2013/0267700 A1  Oct. 10, 2013

Related U.S. Application Data

(63) Continuation of application No. 12/697,000, filed on Jan. 29, 2010, now Pat. No. 8,420,825.

(30) Foreign Application Priority Data

Jan. 29, 2009 (DE) .......................... 10 2009 006 602

(51) Int. Cl.
*A61K 31/44* (2006.01)
*C07D 409/00* (2006.01)

(52) U.S. Cl.
USPC ....................................... 546/281.4; 514/342

(58) Field of Classification Search
None
See application file for complete search history.

(56) References Cited

U.S. PATENT DOCUMENTS

| | | | |
|---|---|---|---|
| 8,420,825 B2 * | 4/2013 | Vakalopoulos et al. ... | 546/281.4 |
| 2011/0003845 A1 * | 1/2011 | Nell et al. ..................... | 514/300 |
| 2011/0136871 A1 * | 6/2011 | Hubsch et al. ................ | 514/335 |

* cited by examiner

*Primary Examiner* — Heidi Reese
(74) *Attorney, Agent, or Firm* — Karen B. King

(57) ABSTRACT

The present application relates to novel 6-alkylamino-substituted dicyanopyridines, to their amino acid ester prodrugs, to processes for their preparation, to their use for the treatment and/or prophylaxis of diseases and to their use for preparing medicaments for the treatment and/or prophylaxis of diseases, preferably for the treatment and/or prevention of cardiovascular disorders.

7 Claims, 3 Drawing Sheets

ALKYLAMINE-SUBSTITUTED DICYANOPYRIDINE AND AMINO ACID ESTER PRODRUGS THEREOF

BACKGROUND OF THE INVENTION

1. Field of the Invention

The present application relates to novel 6-alkylamino-substituted dicyanopyridines, to their amino acid ester prodrugs, to processes for their preparation, to their use for the treatment and/or prophylaxis of diseases and to their use for preparing medicaments for the treatment and/or prophylaxis of diseases, preferably for the treatment and/or prevention of cardiovascular disorders.

2. Description of the Prior Art

Adenosine, a purine nucleoside, is present in all cells and is released by a large number of physiological and pathophysiological stimuli. Adenosine is formed intracellularly as an intermediate during the degradation of adenosine 5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the blood pressure, on the heart rate, on the release of neurotransmitters and on lymphocyte differentiation. In adipocytes, adenosine is capable of inhibiting lipolysis, thus lowering the concentration of free fatty acids and triglycerides in the blood.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. According to the invention, "adenosine-receptor-selective ligands" are substances which bind selectively to one or more subtypes of the adenosine receptors, thus either mimicking the action of adenosine (adenosine agonists) or blocking its action (adenosine antagonists).

The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

In the cardiovascular system, the main consequences of the activation of adenosine receptors are: bradycardia, negative inotropism and protection of the heart against ischemia ("preconditioning") via A1 receptors, dilation of the blood vessels via A2a and A2b receptors and inhibition of the fibroblasts and smooth-muscle-cell proliferation via A2b receptors.

In the case of A1 agonists (coupling preferably via G, proteins), a decrease of the intracellular cAMP concentration is observed (preferably after direct prestimulation of adenylate cyclase by forskolin). Correspondingly, A2a and A2b agonists (coupling preferably via Gs proteins) leads to an increase and A2a and A2b antagonists to a decrease of the cAMP concentration in the cells. In the case of A2 receptors, a direct prestimulation of adenylate cyclase by forskolin is of no benefit.

In humans, activation of A1 receptors by specific A1 agonists leads to a frequency-dependent lowering of the heart rate, without any effect on blood pressure. Selective A1 agonists may thus be suitable inter alia for treating angina pectoris and atrial fibrillation.

The cardioprotective action of the A1 receptors in the heart may be utilized inter alia by activating these A1 receptors with specific A1 agonists for treatment and organ protection in cases of acute myocardial infarction, acute coronary syndrome, heart failure, bypass operations, heart catheter examinations and organ transplantations.

The activation of A2b receptors by adenosine or specific A2b agonists leads, via dilation of blood vessels, to lowering of the blood pressure. The lowering of the blood pressure is accompanied by a reflectory increase in heart rate. The increased heart rate can be reduced by activation of A1 receptors using specific A1 agonists.

The combined action of selective A1/A2b agonists on the vascular system and heart rate thus results in a systemic lowering of the blood pressure without relevant heart-rate increase. Dual A1/A2b agonists having such a pharmacological profile could be employed, for example, for treating hypertension in humans.

In adipocytes, the activation of A1 and A2b receptors leads to an inhibition of lipolysis. Thus, the selective or combined action of A1 and A1/A2b agonists on lipid metabolism results in a lowering of free fatty acids and triglycerides. In turn, in patients suffering from metabolic syndrome and in diabetics, reducing lipids leads to lower insulin resistance and improved symptoms.

The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis", J. Biol. Chem. 267 (1992), pages 10764-10770, the disclosure of which is hereby fully incorporated by way of reference).

The effect of the substances on such cell lines can be monitored by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells", *Naunyn Schmiedebergs Arch. Pharmacol.* 357 (1998), pages 1-9, the disclosure of which is hereby fully incorporated by way of reference).

The "adenosine-receptor-specific" ligands known from the prior art are mainly derivatives based on natural adenosine (S.-A. Poulsen and R. J. Quinn, "Adenosine receptors: New opportunities for future drugs", *Bioorganic and Medicinal Chemistry* 6 (1998), pages 619-641). However, most of these adenosine ligands known from the prior art have the disadvantage that their action is not really receptor-specific, that their activity is less than that of natural adenosine, that they have only very weak activity after oral administration or unwanted side effects on the central nervous system (CNS) (A. K. Dhalla et al, Curr. Topics in Med. Chem. 2003, 3, 369-385; E. Elzein, J. Zablocki, *Exp. Opin. Invest. Drugs* 2008, 17(12), 1901-1910). Thus, they are mainly used only for experimental purposes. Compounds of this type which are still in clinical development are hitherto only suitable for intravenous application.

Prodrugs are derivatives of an active ingredient which undergo in vivo an enzymatic and/or chemical biotransformation in one or more stages before the actual active ingredient is liberated. A prodrug residue is ordinarily used in order to improve the profile of properties of the underlying active ingredient (P. Ettmayer et al., *J. Med. Chem.* 47, 2393 (2004)). In order to achieve an optimal profile of effects it is necessary in this connection for the design of the prodrug residue as well as the desired mechanism of liberation to be coordinated very accurately with the individual active ingredient, the indication, the site of action and the administration route. A large number of medicaments is administered as prodrugs which exhibit an improved bioavailability by comparison with the underlying active ingredient, for example achieved by improving the physicochemical profile, specifically the solubility, the active or passive absorption properties or the tissue-specific distribution. An example which may be mentioned from the wide-ranging literature on prodrugs is: H. Bundgaard (Ed.), *Design of Prodrugs: Bioreversible derivatives for various functional groups and chemical entities*, Elsevier Science Publishers B.V., 1985. A review of prodrug derivatives based on carboxylic acid esters and possible properties of such compounds can be found, for example, in K. Beaumont et al., *Curr. Drug Metab.* 4, 461-485 (2003). Also known are dipeptide prodrugs of acyclovir for treating ocular herpes infections (B. S. Anand et al., *Curr. Eye Res.* 26, No. 3-4, 151-163 (2003)) which interact with the oligopeptide transporter on the cornea, thus increasing the bioavailability of acylovir in the eye.

WO 01/25210, WO 02/070484, WO 02/070485, WO 03/053441, WO 2008/028590, WO 2009/100827, WO 2009/015776 and WO 2009/112155 disclose variously substituted 3,5-dicyano-6-aminopyridines as adenosine receptor ligands for treating cardiovascular disorders. WO 2009/015811 and WO 2009/015812 describe amino acid ester prodrugs of 3,5-dicyano-6-aminopyridines.

SUMMARY OF THE INVENTION

It was an object of the present invention to provide novel compounds which act as potent and selective agonists of the adenosine A1 receptor or as selective dual agonists of the A1 and A2b receptor, have identical or improved physicochemical and/or pharmacokinetic properties and also an advantageous therapeutic and/or pharmacological activity profile, and which, as such, are suitable for the treatment and/or prevention of diseases, in particular for the treatment and/or prevention of cardiovascular disorders, and also for identifying suitable amino acid ester prodrugs of the novel compounds which have improved solubility in water, physiological media and organic solvents and/or improved bioavailability after oral administration and at the same time allow, after administration, controlled release of the active ingredient in the body of the patient. By improved intravenous administrability it may furthermore be possible to open other therapeutic areas of use for this active ingredient.

DETAILED DESCRIPTION OF THE INVENTION

Figure 1:
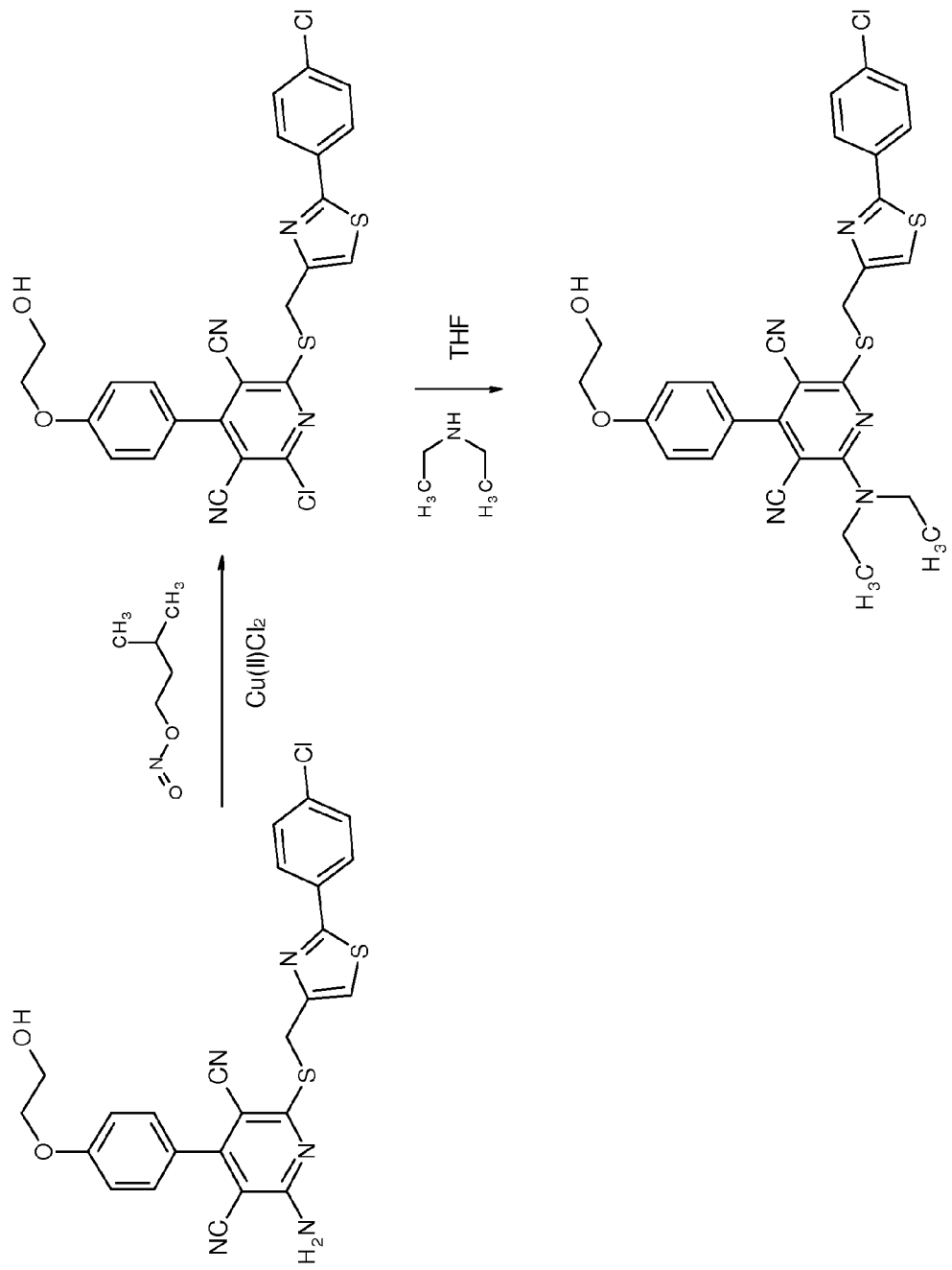
FIG. 1 is Scheme 1 for preparing the compounds of the formula (I).

The present invention provides compounds of the formula (I)

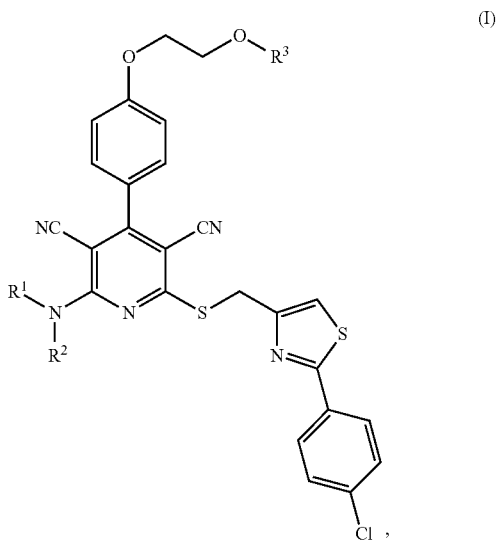

in which $R^1$ represents hydrogen or $(C_1-C_4)$-alkyl, $R^2$ represents $(C_1-C_6)$-alkyl, $(C_2-C_4)$-alkenyl, $(C_2-C_4)$-alkynyl or $(C_3-C_7)$-cycloalkyl, where $(C_1-C_6)$-alkyl may be substituted by 1 to 3 substituents selected independently of one another from the group consisting of fluorine, chlorine, trifluoromethyl, trifluoromethoxy, $(C_1-C_4)$-alkoxy, $(C_3-C_7)$-cycloalkyl, $(C_3-C_7)$-cycloalkoxy, $(C_1-C_4)$-alkylsulfanyl and $(C_1-C_4)$-alkylsulfonyl, and where $(C_2-C_4)$-alkenyl and $(C_2-C_4)$-alkynyl may be substituted by 1 or 2 substituents selected independently of one another from the group consisting of fluorine, trifluoromethyl, $(C_1-C_4)$-alkyl, trifluoromethoxy and $(C_1-C_4)$-alkoxy, and where $(C_3-C_7)$-cycloalkyl may be substituted by 1 or 2 substituents selected independently of one another from the group consisting of fluorine, chlorine, trifluoromethyl, $(C_1-C_4)$-alkyl, trifluoromethoxy and $(C_1-C_4)$-alkoxy, or $R^1$ and $R^2$ together with the nitrogen atom to which they are attached form a 4- to 7-membered heterocycle which may contain a further heteroatom from the group consisting of N, O and S, where the 4- to 7-membered heterocycle may be substituted by 1 or 2 substituents selected independently of one another from the group consisting of fluorine, chlorine, oxo, trifluoromethyl, $(C_1-C_4)$-alkyl, trifluoromethoxy and $(C_1-C_4)$-alkoxy, $R^3$ represents hydrogen or a group of the formula

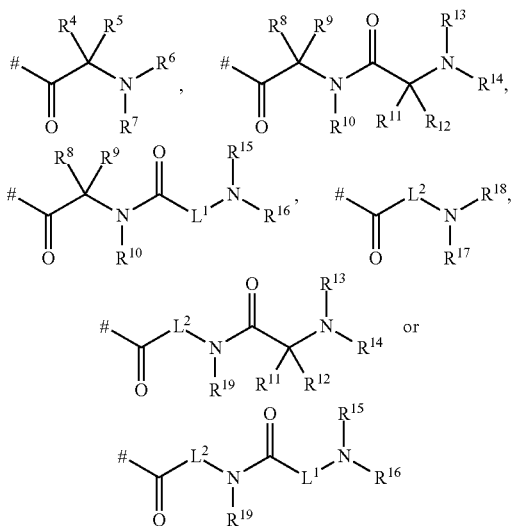

where
\# represents the point of attachment to the oxygen atom,
$L^1$ represents $(C_2-C_6)$-alkanediyl,
$L^2$ represents $(C_2-C_6)$-alkanediyl,
$R^4$ represents hydrogen or the side group of a natural α-amino acid or its homologs or isomers,
$R^5$ represents hydrogen or methyl,
$R^6$ represents hydrogen or $(C_1-C_4)$-alkyl,
$R^7$ represents hydrogen or $(C_1-C_4)$-alkyl,
or
$R^6$ and $R^7$ together with the nitrogen atom to which they are attached form a 5- or 6-membered heterocycle,
where the 5- or 6-membered heterocycle may be substituted by 1 or 2 substituents independently selected from the group consisting of $(C_1-C_4)$-alkyl, amino, hydroxyl and $(C_1-C_4)$-alkoxy,
or
$R^7$ together with $R^4$ and the atoms, to which they are attached, forms a pyrrolidine or piperidine ring,
$R^8$ represents hydrogen or the side group of a natural α-amino acid or its homologs or isomers,
$R^9$ represents hydrogen or methyl,
$R^{10}$ represents hydrogen or methyl,
$R^{11}$ represents hydrogen or the side group of a natural α-amino acid or its homologs or isomers,
$R^{12}$ represents hydrogen or methyl,
$R^{13}$ represents hydrogen or $(C_1-C_4)$-alkyl,
$R^{14}$ represents hydrogen or $(C_1-C_4)$-alkyl,
or
$R^{13}$ and $R^{14}$ together with the nitrogen atom to which they are attached form a 5- or 6-membered heterocycle,
where the 5- or 6-membered heterocycle may be substituted by 1 or 2 substituents independently selected from the group consisting of $(C_1-C_4)$-alkyl, amino, hydroxyl and $(C_1-C_4)$-alkoxy,
or
$R^{14}$ together with $R^{11}$ and the atoms, to which they are attached, forms a pyrrolidine or piperidine ring,
$R^{15}$ represents hydrogen or $(C_1-C_4)$-alkyl,
$R^{16}$ represents hydrogen or $(C_1-C_4)$-alkyl,
or
$R^{15}$ and $R^{16}$ together with the nitrogen atom to which they are attached form a 5- or 6-membered heterocycle,
where the 5- or 6-membered heterocycle may be substituted by 1 or 2 substituents independently selected from the group consisting of $(C_1-C_4)$-alkyl, amino, hydroxyl and $(C_1-C_4)$-alkoxy,
$R^{17}$ represents hydrogen or $(C_1-C_4)$-alkyl,
$R^{18}$ represents hydrogen or $(C_1-C_4)$-alkyl,
or
$R^{17}$ and $R^{18}$ together with the nitrogen atom to which they are attached form a 5- or 6-membered heterocycle,
where the 5- or 6-membered heterocycle may be substituted by 1 or 2 substituents independently selected from the group consisting of $(C_1-C_4)$-alkyl, amino, hydroxyl and $(C_1-C_4)$-alkoxy,
$R^{19}$ represents hydrogen or methyl,
and N-oxides, salts, solvates, salts of the N-oxides and solvates of the N-oxides and salts thereof.

Compounds according to the invention are the compounds of the formula (I) and the N-oxides, salts, solvates, salts of the N-oxides and solvates of the salts and N-oxides thereof, the compounds which are encompassed by the formula (I) of the formulae mentioned below, and the salts, solvates and solvates of the salts thereof, and the compounds which are encompassed by formula (I) and are mentioned below as exemplary embodiments, and the salts, solvates and solvates of the salts thereof, where the compounds which are encompassed by the formula (I) and are mentioned below are not already salts, solvates and solvates of the salts.

The compounds according to the invention may, depending on their structure, exist in stereoisomeric forms (enantiomers, diastereomers). The invention therefore encompasses the enantiomers or diastereomers and respective mixtures thereof. The stereoisomerically pure constituents can be isolated from such mixtures of enantiomers and/or diastereomers in a known manner.

Where the compounds according to the invention can exist in tautomeric forms, the present invention encompasses all tautomeric forms.

Salts preferred for the purposes of the present invention are physiologically acceptable salts of the compounds according to the invention. Also included are salts which are not themselves suitable for pharmaceutical applications but can be used, for example, for the isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. For the purposes of the present invention, preferred solvates are hydrates.

In addition, the present invention also encompasses prodrugs of the compounds according to the invention. The term "prodrugs" encompasses compounds which for their part may be biologically active or inactive but are converted (for example metabolically or hydrolytically) into compounds according to the invention during their residence time in the body.

For the purposes of the present invention, the substituents have the following meaning, unless specified otherwise:

Alkyl is in the context of the invention a straight-chain or branched alkyl radical having 1 to 6 or 1 to 4 carbon atoms. A straight-chain or branched alkyl radical having 1 to 4 carbon atoms is preferred. The following radicals may be mentioned by way of example and by way of preference: methyl, ethyl, n-propyl, isopropyl, n-butyl, isobutyl, sec-butyl, tert-butyl, 1-ethyl-propyl, n-pentyl and n-hexyl.

Alkenyl is in the context of the invention a straight-chain or branched alkenyl radical having 2 to 4 carbon atoms and a double bond. The following radicals may be mentioned by way of example and by way of preference: vinyl, allyl, isopropenyl and n-but-2-en-1-yl.

Alkynyl is in the context of the invention a straight-chain or branched alkynyl radical having 2 to 4 carbon atoms and a triple bond. The following radicals may be mentioned by way of example and by way of preference: ethynyl, n-prop-1-yn-1-yl, n-prop-2-yn-1-yl, n-but-2-yn-1-yl and n-but-3-yn-1-yl.

Alkanediyl is in the context of the invention a straight-chain or branched divalent alkyl radical having 2 to 6 carbon atoms. The following radicals may be mentioned by way of example and by way of preference: methylene, ethane-1,1-diyl, ethane-1,2-diyl, propane-1,1-diyl, propane-1,2-diyl, propane-2,2-diyl, propane-1,3-diyl, butane-1,4-diyl, butane-1,2-diyl, butane-1,3-diyl, butane-2,3-diyl or butane-3,4-diyl.

Cycloalkyl is in the context of the invention a monocyclic saturated carbocycle having 3 to 7 or 5 or 6 ring carbon atoms. The following radicals may be mentioned by way of example and by way of preference: cyclopropyl, cyclobutyl, cyclopentyl, cyclohexyl and cycloheptyl.

Alkoxy is in the context of the invention a straight-chain or branched alkoxy radical having 1 to 6 or 1 to 4 or 2 to 4 carbon atoms. A straight-chain or branched alkoxy adical having 1 to 4 or 2 to 4 carbon atoms is preferred. The following radicals may be mentioned by way of example and by way of preference: methoxy, ethoxy, n-propoxy, isopropoxy, n-butoxy, tert-butoxy, n-pentoxy and n-hexoxy.

Cycloalkoxy is in the context of the invention a monocyclic saturated carbocycle having 3 to 7 carbon atoms which is attached via an oxygen atom. The following radicals may be mentioned by way of example and by way of preference: cyclopropyloxy, cyclobutyloxy, cyclopentyloxy, cyclohexyloxy and cycloheptyloxy.

Alkylsulfanyl is in the context of the invention a straight-chain or branched alkyl radical having 1 to 4 carbon atoms which is attached via a sulfanyl group. The following radicals may be mentioned by way of example and by way of preference: methylsulfanyl, ethylsulfanyl, n-propylsulfanyl, isopropylsulfanyl, n-butylsulfanyl and tert-butylsulfanyl.

Alkylsulfonyl is in the context of the invention a straight-chain or branched alkyl radical having 1 to 4 carbon atoms which is attached via a sulfonyl group. The following radicals may be mentioned by way of example and by way of preference: methylsulfonyl, ethylsulfonyl, n-propylsulfonyl, isopropylsulfonyl, n-butylsulfonyl and tert-butylsulfonyl.

Heterocycle is in the context of the invention a saturated heterocycle having a total of 4 to 7 ring atoms which contains one or two ring heteroatoms from the group consisting of N, O and S and is attached via a ring carbon atom or, if appropriate, a ring nitrogen atom. The following radicals may be mentioned by way of example: azetidinyl, pyrrolidinyl, pyrazolidinyl, tetrahydrofuranyl, piperidinyl, piperazinyl, tetrahydropyranyl, morpholinyl, thiomorpholinyl and azepanyl. Azetidinyl, pyrrolidinyl, tetrahydrofuranyl, piperidinyl, piperazinyl, tetrahydropyranyl and morpholinyl are preferred. Azetidinyl, pyrrolidinyl, piperidinyl and morpholinyl are particular.

The side group of an α-amino acid in the meaning of $R^3$ encompasses both the side groups of naturally occurring α-amino acids and the side groups of homologs and isomers of these α-amino acids. The α-amino acid may in this connection have both the L and the D configuration or else be a mixture of the L form and D form. Examples of side groups which may be mentioned are: methyl (alanine), propan-2-yl (valine), propan-1-yl (norvaline), 2-methylpropan-1-yl (leucine), 1-methylpropan-1-yl (isoleucine), butan-1-yl (norleucine), tert-butyl (2-tert-butylglycine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 2-aminoethyl (2,4-diaminobutyric acid), aminomethyl (2,3-diaminopropionic acid), 3-guanidinopropan-1-yl (arginine), 3-ureidopropan-1-yl (citrulline). Preferred α-amino acid side groups in the meaning of $R^3$ are methyl (alanine), propan-2-yl (valine), 2-methylpropan-1-yl (leucine), benzyl (phenylalanine), imidazol-4-ylmethyl (histidine), hydroxymethyl (serine), 1-hydroxyethyl (threonine), 4-aminobutan-1-yl (lysine), 3-aminopropan-1-yl (ornithine), 2-aminoethyl (2,4-diaminobutyric acid), aminomethyl (2,3-diaminopropionic acid), 3-guanidinopropan-1-yl (arginine). The L configuration is preferred in each case.

An oxo group is in the context of the invention an oxygen atom which is attached via a double bond to a carbon atom.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one, two or three identical or different substituents. Very particularly preferred is substitution by one or two identical or different substituents.

In the context of the present invention, preference is given to compounds of the formula (I) in which $R^1$ represents hydrogen, methyl or ethyl, $R^2$ represents $(C_1$-$C_6)$-alkyl or $(C_3$-$C_6)$-cycloalkyl, where $(C_1$-$C_6)$-alkyl may be substituted by 1 to 3 substituents selected independently of one another from the group consisting of fluorine, chlorine, trifluoromethyl, trifluoromethoxy and $(C_1$-$C_3)$-alkoxy, or $R^1$ and $R^2$ together with the nitrogen atom to which they are attached form a 4- to 6-membered heterocycle which may contain a further heteroatom from the group consisting of N, O and S, where the 4- to 6-membered heterocycle may be substituted by 1 or 2 substituents selected independently of one another from the group consisting of fluorine, trifluoromethyl, (C$_1$-C$_4$)-alkyl, trifluoromethoxy, methoxy and ethoxy,
R$^3$ represents hydrogen or a group of the formula where
# represents the point of attachment to the oxygen atom,
L$^1$ represents ethane-1,2-diyl,
L$^2$ represents ethane-1,2-diyl or propane-1,3-diyl,
R$^4$ represents hydrogen, methyl, 2-methylpropan-1-yl, hydroxymethyl, 1-hydroxyethyl, 4-aminobutan-1-yl or 3-aminopropan-1-yl,
R$^5$ represents hydrogen,
R$^6$ represents hydrogen or methyl,
R$^7$ represents hydrogen or methyl,
or
R$^7$ together with R$^4$ and the atoms, to which they are attached, forms a pyrrolidine ring,
R$^8$ represents hydrogen, methyl, propan-2-yl, 1-methylpropan-1-yl, 2-methylpropan-1-yl or 1-hydroxyethyl,
R$^9$ represents hydrogen,
R$^{10}$ represents hydrogen,
R$^{11}$ represents methyl, 1-methylpropan-1-yl, imidazol-4-ylmethyl, 4-aminobutan-1-yl, 3-aminopropan-1-yl, 2-aminoethyl, aminomethyl or 3-guanidinopropan-1-yl,
R$^{12}$ represents hydrogen,
R$^{13}$ represents hydrogen or methyl,
R$^{14}$ represents hydrogen or methyl,
or
R$^{14}$ together with R$^{11}$ and the atoms, to which they are attached, forms a pyrrolidine ring,
R$^{15}$ represents hydrogen or methyl,
R$^{16}$ represents hydrogen or methyl,
R$^{17}$ represents hydrogen or methyl,
R$^{18}$ represents hydrogen or methyl,
R$^{19}$ represents hydrogen or methyl,
and the salts, solvates and solvates of the salts thereof.

In the context of the present invention, particular preference is given to compounds of the formula (I) in which
R$^1$ represents hydrogen, methyl or ethyl,
R$^2$ represents (C$_1$-C$_3$)-alkyl, cyclopropyl or cyclobutyl,
where (C$_1$-C$_3$)-alkyl may be substituted by 1 or 2 substituents selected independently of one another from the group consisting of fluorine, chlorine, trifluoromethyl, methoxy, ethoxy, cyclopropyl and cyclobutyl,
or
R$^1$ and R$^2$ together with the nitrogen atom to which they are attached form a 4- to 6-membered heterocycle which may contain a further heteroatom from the group consisting of N, O and S,
where the 4- to 6-membered heterocycle may be substituted by 1 or 2 substituents selected independently of one another from the group consisting of fluorine, trifluoromethyl, methyl, ethyl, methoxy and ethoxy,
R$^3$ represents hydrogen or a group of the formula where
# represents the point of attachment to the oxygen atom,
L$^1$ represents ethane-1,2-diyl,
L$^2$ represents ethane-1,2-diyl,
R$^4$ represents methyl or 3-aminopropan-1-yl,
R$^5$ represents hydrogen,
R$^6$ represents hydrogen,
R$^7$ represents hydrogen,
R$^8$ represents methyl or 2-methylpropan-1-yl,
R$^9$ represents hydrogen,
R$^{10}$ represents hydrogen,
R$^{11}$ represents methyl, 1-methylpropan-1-yl, imidazol-4-ylmethyl, 4-aminobutan-1-yl, 3-aminopropan-1-yl, 2-aminoethyl, aminomethyl or 3-guanidinopropan-1-yl,
R$^{12}$ represents hydrogen,
R$^{13}$ represents hydrogen,
R$^{14}$ represents hydrogen,
or
R$^{14}$ together with R$^{11}$ and the atoms, to which they are attached, forms a pyrrolidine ring,
R$^{15}$ represents hydrogen,
R$^{16}$ represents hydrogen,
R$^{17}$ represents hydrogen,
R$^{18}$ represents hydrogen,
R$^{19}$ represents hydrogen,
and the salts, solvates and solvates of the salts thereof.

In the context of the present invention, particular preference is also given to compounds of the formula (I) in which
R$^1$ and R$^2$ together with the nitrogen atom to which they are attached form an azetidinyl, pyrrolidinyl or piperidinyl ring, where the azetidinyl and piperidinyl ring may be substituted by a methoxy substituent, $R^3$ represents a group of the formula

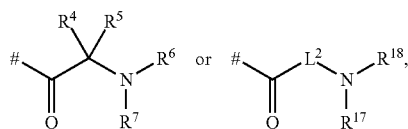

where
# represents the point of attachment to the oxygen atom,
$L^2$ represents ethane-1,2-diyl,
$R^4$ represents hydrogen, methyl, 1-methylpropan-1-yl, 4-aminobutan-1-yl or 3-guanidinopropan-1-yl,
$R^5$ represents hydrogen,
$R^6$ represents hydrogen,
$R^7$ represents hydrogen,
$R^{17}$ represents hydrogen,
and
$R^{18}$ represents hydrogen,
and the salts, solvates and solvates of the salts thereof.

In the context of the present invention, particular preference is also given to compounds of the formula (I) in which $R^1$ and $R^2$ together with the nitrogen atom to which they are attached form an azetidinyl, pyrrolidinyl or piperidinyl ring, where the azetidinyl and piperidinyl ring may be substituted by a methoxy substituent,
$R^3$ represents a group of the formula

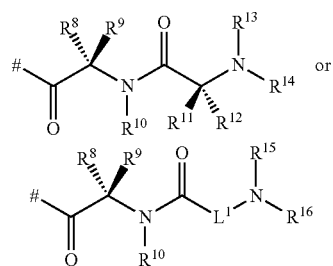

where
# represents the point of attachment to the oxygen atom,
$L^1$ represents ethane-1,2-diyl,
$R^9$ represents methyl or isobutyl,
$R^9$ represents hydrogen,
$R^{10}$ represents hydrogen,
$R^{11}$ represents hydrogen, methyl, 1-methylpropan-1-yl, imidazol-4-ylmethyl, 4-aminobutan-1-yl, 3-aminopropan-1-yl, 2-aminoethyl, aminomethyl, imidazol-4-ylmethyl or 3-guanidinopropan-1-yl,
$R^{12}$ represents hydrogen,
$R^{13}$ represents hydrogen,
$R^{14}$ represents hydrogen,
or
$R^{14}$ together with $R^{11}$ and the atoms, to which they are attached, forms a pyrrolidine ring,
$R^{15}$ represents hydrogen,
$R^{16}$ represents hydrogen,
and the salts, solvates and solvates of the salts thereof.

In the context of the present invention, particular preference is also given to compounds of the formula (I) in which $R^1$ and $R^2$ together with the nitrogen atom to which they are attached form an azetidinyl, pyrrolidinyl or piperidinyl ring, where the azetidinyl and piperidinyl ring may be substituted by a methoxy substituent, $R^3$ represents a group of the formula

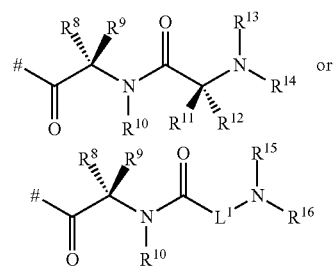

where
# represents the point of attachment to the oxygen atom,
$L^1$ represents ethane-1,2-diyl,
$R^8$ represents methyl or isobutyl,
$R^9$ represents hydrogen,
$R^{10}$ represents hydrogen,
$R^{11}$ represents hydrogen, methyl, 1-methylpropan-1-yl, 4-aminobutan-1-yl or 3-guanidinopropan-1-yl,
$R^{12}$ represents hydrogen,
$R^{13}$ represents hydrogen,
$R^{14}$ represents hydrogen,
or
$R^{14}$ together with $R^{11}$ and the atoms, to which they are attached, forms a pyrrolidine ring,
$R^{15}$ represents hydrogen,
$R^{16}$ represents hydrogen,
and the salts, solvates and solvates of the salts thereof.

In the context of the present invention, particular preference is also given to compounds of the formula (I) in which $R^1$ and $R^2$ together with the nitrogen atom to which they are attached form a pyrrolidinyl ring,
$R^3$ represents a group of the formula

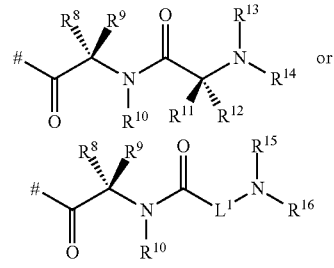

where
# represents the point of attachment to the oxygen atom,
$L^1$ represents ethane-1,2-diyl,
$R^8$ represents methyl or isobutyl,
$R^9$ represents hydrogen,
$R^{10}$ represents hydrogen,
$R^{11}$ represents hydrogen, methyl, 1-methylpropan-1-yl, 4-aminobutan-1-yl or 3-guanidinopropan-1-yl,
$R^{12}$ represents hydrogen,
$R^{13}$ represents hydrogen,
$R^{14}$ represents hydrogen,
or
$R^{14}$ together with $R^{11}$ and the atoms, to which they are attached, forms a pyrrolidine ring,
$R^{15}$ represents hydrogen,
$R^{16}$ represents hydrogen,
and the salts, solvates and solvates of the salts thereof.

In the context of the present invention, particular preference is also given to compounds of the formula (I) in which
$R^1$ represents hydrogen, methyl or ethyl,
$R^2$ represents $(C_1-C_3)$-alkyl, cyclopropyl or cyclobutyl,
where $(C_1-C_3)$-alkyl may be substituted by 1 or 2 substituents selected independently of one another from the group consisting of fluorine, chlorine, trifluoromethyl, methoxy, ethoxy, cyclopropyl and cyclobutyl,
$R^3$ represents hydrogen,
and the salts, solvates and solvates of the salts thereof.

In the context of the present invention, particular preference is also given to compounds of the formula (I) in which
$R^1$ represents hydrogen, methyl or ethyl,
$R^2$ represents methyl, ethyl or n-propyl,
where methyl, ethyl and n-propyl may be substituted by 1 or 2 substituents selected independently of one another from the group consisting of fluorine, trifluoromethyl and methoxy,
or
$R^1$ and $R^2$ together with the nitrogen atom to which they are attached form an azetidinyl, pyrrolidinyl or piperidinyl ring,
where the azetidinyl and piperidinyl ring may be substituted by a methoxy substituent,
$R^3$ represents hydrogen,
and the salts, solvates and solvates of the salts thereof.

In the context of the present invention, particular preference is also given to compounds of the formula (I) in which
$R^1$ represents hydrogen, methyl or ethyl,
$R^2$ represents $(C_1-C_3)$-alkyl, cyclopropyl or cyclobutyl,
where $(C_1-C_3)$-alkyl may be substituted by 1 or 2 substituents selected independently of one another from the group consisting of fluorine, chlorine, trifluoromethyl, methoxy, ethoxy, cyclopropyl and cyclobutyl,
$R^3$ represents a group of the formula

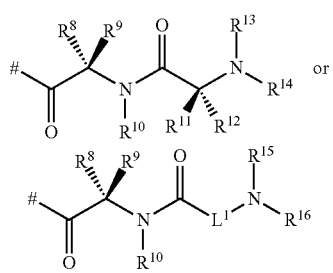

where
# represents the point of attachment to the oxygen atom,
$L^1$ represents ethane-1,2-diyl,
$R^8$ represents methyl or isobutyl,
$R^9$ represents hydrogen,
$R^{10}$ represents hydrogen,
$R^{11}$ represents hydrogen, methyl, 1-methylpropan-1-yl, 4-aminobutan-1-yl or 3-guanidinopropan-1-yl,
$R^{12}$ represents hydrogen,
$R^{13}$ represents hydrogen,
$R^{14}$ represents hydrogen,
or
$R^{14}$ together with $R^{11}$ and the atoms, to which they are attached, forms a pyrrolidine ring,
$R^{15}$ represents hydrogen,
$R^{16}$ represents hydrogen,
and the salts, solvates and solvates of the salts thereof.

In the context of the present invention, particular preference is also given to compounds of the formula (I) in which
$R^1$ and $R^2$ together with the nitrogen atom to which they are attached form an azetidinyl, pyrrolidinyl or piperidinyl ring,
where the azetidinyl, pyrrolidinyl or piperidinyl ring may be substituted by 1 or 2 substituents selected independently of one another from the group consisting of fluorine, trifluoromethyl, methyl, ethyl, methoxy and ethoxy,
and
$R^3$ represents hydrogen,
and the salts, solvates and solvates of the salts thereof.

In the context of the present invention, particular preference is also given to compounds of the formula (I) in which
$R^1$ and $R^2$ together with the nitrogen atom to which they are attached form a pyrrolidinyl ring,
$R^3$ represents a group of the formula

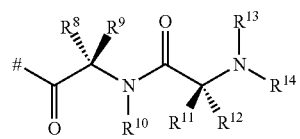

where
# represents the point of attachment to the oxygen atom,
$R^8$ represents methyl,
$R^9$ represents hydrogen,
$R^{10}$ represents hydrogen,
$R^{11}$ represents methyl or 1-methylpropan-1-yl,
$R^{12}$ represents hydrogen,
$R^{13}$ represents hydrogen,
$R^{14}$ represents hydrogen,
and the salts, solvates and solvates of the salts thereof.

In the context of the present invention, preference is also given to compounds of the formula (I) in which $R^3$ represents hydrogen, and the N-oxides, salts, solvates, salts of the N-oxides and solvates of the N-oxides and salts thereof.

In the context of the present invention, preference is also given to compounds of the formula (I) in which
$R^3$ represents hydrogen or a group of the formula

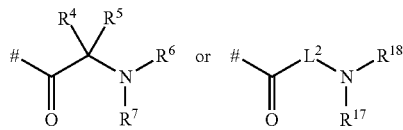

where
# represents the point of attachment to the oxygen atom,
$L^2$ represents ethane-1,2-diyl,
$R^4$ represents methyl or 3-aminopropan-1-yl,
$R^5$ represents hydrogen,
$R^6$ represents hydrogen,
$R^7$ represents hydrogen,
$R^{17}$ represents hydrogen,
$R^{18}$ represents hydrogen,
and the salts, solvates and solvates of the salts thereof.

In the context of the present invention, preference is also given to compounds of the formula (I) in which $R^3$ represents hydrogen or a group of the formula

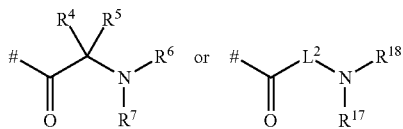

where
# represents the point of attachment to the oxygen atom,
$L^2$ represents ethane-1,2-diyl or propane-1,3-diyl,
$R^4$ represents hydrogen, methyl, 2-methylpropan-1-yl, hydroxymethyl, 1-hydroxyethyl, 4-aminobutan-1-yl or 3-aminopropan-1-yl,
$R^5$ represents hydrogen,
$R^6$ represents hydrogen or methyl,
$R^7$ represents hydrogen or methyl,
or
$R^7$ together with $R^4$ and the atoms, to which they are attached, forms a pyrrolidine ring,
$R^{17}$ represents hydrogen or methyl,
$R^{18}$ represents hydrogen or methyl,
and the salts, solvates and solvates of the salts thereof.

In the context of the present invention, preference is also given to compounds of the formula (I) in which
$R^3$ represents hydrogen or a group of the formula

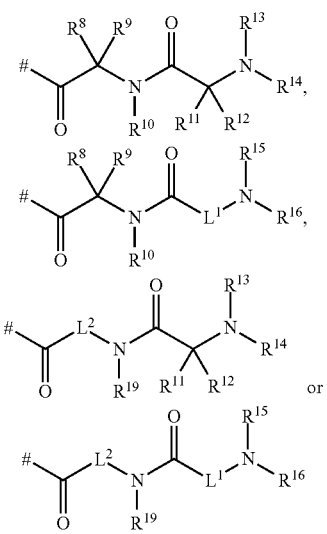

where
# represents the point of attachment to the oxygen atom,
$L^1$ represents ethane-1,2-diyl,
$L^2$ represents ethane-1,2-diyl,
$R^8$ represents hydrogen, methyl, propan-2-yl, 1-methylpropan-1-yl, 2-methylpropan-1-yl or 1-hydroxyethyl,
$R^9$ represents hydrogen,
$R^{10}$ represents hydrogen,
$R^{11}$ represents methyl, 1-methylpropan-1-yl, imidazol-4-yl-methyl, 4-aminobutan-1-yl, 3-aminopropan-1-yl, 2-aminoethyl, aminomethyl or 3-guanidinopropan-1-yl,
$R^{12}$ represents hydrogen,
$R^{13}$ represents hydrogen or methyl,
$R^{14}$ represents hydrogen or methyl,
or
$R^{14}$ together with $R^{11}$ and the atoms, to which they are attached, forms a pyrrolidine ring,
$R^{15}$ represents hydrogen or methyl,
$R^{16}$ represents hydrogen or methyl,
$R^{17}$ represents hydrogen or methyl,
$R^{18}$ represents hydrogen or methyl,
$R^{19}$ represents hydrogen or methyl,
and the salts, solvates and solvates of the salts thereof.

In the context of the present invention, preference is also given to compounds of the formula (I) in which
$R^3$ represents hydrogen or a group of the formula

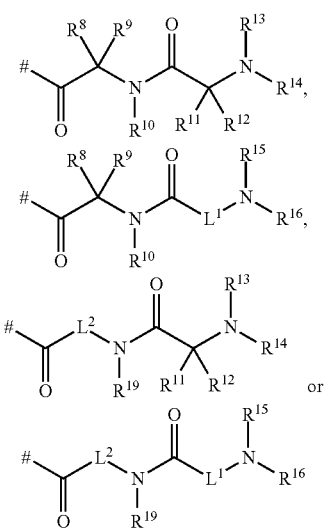

where
# represents the point of attachment to the oxygen atom,
$L^1$ represents ethane-1,2-diyl,
$L^2$ represents ethane-1,2-diyl or propane-1,3-diyl,
$R^8$ represents methyl or 2-methylpropan-1-yl,
$R^9$ represents hydrogen,
$R^{10}$ represents hydrogen,
$R^{11}$ represents methyl, 1-methylpropan-1-yl, imidazol-4-yl-methyl, 4-aminobutan-1-yl, 3-aminopropan-1-yl, 2-aminoethyl, aminomethyl or 3-guanidinopropan-1-yl,
$R^{12}$ represents hydrogen,
$R^{13}$ represents hydrogen,
$R^{14}$ represents hydrogen,
or
$R^{14}$ together with $R^{11}$ and the atoms, to which they are attached, forms a pyrrolidine ring,
$R^{15}$ represents hydrogen,
$R^{16}$ represents hydrogen,
$R^{17}$ represents hydrogen,
$R^{18}$ represents hydrogen,
$R^{19}$ represents hydrogen,
and the salts, solvates and solvates of the salts thereof.

In the context of the present invention, preference is also given to compounds of the formula (I) in which
$R^3$ represents hydrogen or a group of the formula

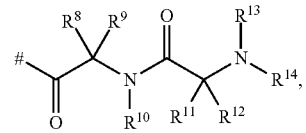

-continued

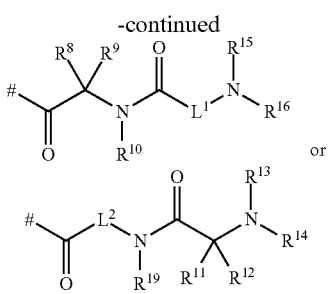

or where
# represents the point of attachment to the oxygen atom,
$L^1$ represents ethane-1,2-diyl,
$L^2$ represents ethane-1,2-diyl,
$R^9$ represents methyl,
$R^9$ represents hydrogen,
$R^{10}$ represents hydrogen,
$R^{11}$ represents methyl, 1-methylpropan-1-yl, 4-aminobutan-1-yl or 3-aminopropan-1-yl,
$R^{12}$ represents hydrogen,
$R^{13}$ represents hydrogen,
$R^{14}$ represents hydrogen,
or
$R^{14}$ together with $R^{11}$ and the atoms, to which they are attached, forms a pyrrolidine ring,
$R^{15}$ represents hydrogen,
$R^{16}$ represents hydrogen,
$R^{17}$ represents hydrogen,
$R^{18}$ represents hydrogen,
$R^{19}$ represents hydrogen,
and the salts, solvates and solvates of the salts thereof.

In the context of the present invention, preference is also given to compounds of the formula (I) in which
$R^1$ represents hydrogen, methyl or ethyl,
$R^2$ represents $(C_1-C_3)$-alkyl,
where $(C_1-C_3)$-alkyl may be substituted by 1 or 2 substituents selected independently of one another from the group consisting of fluorine, chlorine, trifluoromethyl, methoxy, ethoxy, cyclopropyl and cyclobutyl,
or
$R^1$ and $R^2$ together with the nitrogen atom to which they are attached form a 4- to 6-membered heterocycle which may contain a further heteroatom from the group consisting of N, O and S,
where the 4- to 6-membered heterocycle may be substituted by 1 or 2 substituents selected independently of one another from the group consisting of fluorine, trifluoromethyl, methyl, ethyl, methoxy and ethoxy,
and the salts, solvates and solvates of the salts thereof.

In the context of the present invention, preference is also given to compounds of the formula (I) in which
$R^1$ represents ethyl,
$R^2$ represents ethyl,
or
$R^1$ and $R^2$ together with the nitrogen atom to which they are attached form a 4- to 6-membered heterocycle which may contain a further heteroatom from the group consisting of N, O and S,
and the salts, solvates and solvates of the salts thereof.

In the context of the present invention, preference is also given to compounds of the formula (I) in which
$R^3$ represents a group of the formula

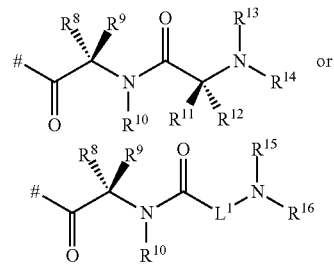

or where
# represents the point of attachment to the oxygen atom,
$L^1$ represents ethane-1,2-diyl,
$R^8$ represents methyl or isobutyl,
$R^9$ represents hydrogen,
$R^{10}$ represents hydrogen,
$R^{11}$ represents hydrogen, methyl, 1-methylpropan-1-yl or 3-guanidinopropan-1-yl,
$R^{12}$ represents hydrogen,
$R^{13}$ represents hydrogen,
$R^{14}$ represents hydrogen,
or
$R^{14}$ together with $R^{11}$ and the atoms, to which they are attached, forms a pyrrolidine ring,
$R^{15}$ represents hydrogen,
$R^{16}$ represents hydrogen,
and the salts, solvates and solvates of the salts thereof.

In the context of the present invention, preference is also given to compounds of the formula (I) in which
$R^3$ represents a group of the formula

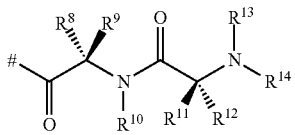

where
# represents the point of attachment to the oxygen atom,
$R^8$ represents methyl,
$R^9$ represents hydrogen,
$R^{10}$ represents hydrogen,
$R^{11}$ represents methyl or 1-methylpropan-1-yl,
$R^{12}$ represents hydrogen,
$R^{13}$ represents hydrogen,
$R^{14}$ represents hydrogen,
and the salts, solvates and solvates of the salts thereof.

In the context of the present invention, preference is also given to compounds of the formula (I) in which
$R^1$ and $R^2$ together with the nitrogen atom to which they are attached form an azetidinyl, pyrrolidinyl or piperidinyl ring, where the azetidinyl, pyrrolidinyl or piperidinyl ring may be substituted by 1 or 2 substituents selected independently of one another from the group consisting of fluorine, trifluoromethyl, methyl, ethyl, methoxy and ethoxy,
and the salts, solvates and solvates of the salts thereof.

In the context of the present invention, preference is also given to compounds of the formula (I) in which
$R^1$ and $R^2$ together with the nitrogen atom to which they are attached form an azetidinyl, pyrrolidinyl or piperidinyl ring,
and the salts, solvates and solvates of the salts thereof.

In the context of the present invention, preference is also given to compounds of the formula (I) in which R¹ and R² together with the nitrogen atom to which they are attached form a pyrrolidinyl ring, where the pyrrolidinyl ring may be substituted by 1 or 2 substituents selected independently of one another from the group consisting of fluorine, trifluoromethyl, methyl, ethyl, methoxy and ethoxy, and the salts, solvates and solvates of the salts thereof.

In the context of the present invention, particular preference is given to the following compounds:

2-({(2-(4-chlorophenyl)-1,3-thiazol-4-yl)methyl}sulfanyl)-4-(4-(2-hydroxyethoxy)phenyl)-6-(pyrrolidin-1-yl)pyridine-3,5-dicarbonitrile 2-({(2-(4-chlorophenyl)-1,3-thiazol-4-yl)methyl}sulfanyl)-4-(4-(2-hydroxyethoxy)phenyl)-6-(methylamino)pyridine-3,5-dicarbonitrile 2-({(2-(4-chlorophenyl)-1,3-thiazol-4-yl)methyl}thio)-6-(ethylamino)-4-(4-(2-hydroxy-ethoxy)phenyl)pyridine-3,5-dicarbonitrile 2-({(2-(4-chlorophenyl)-1,3-thiazol-4-yl)methyl}thio)-6-(dimethylamino)-4-(4-(2-hydroxy-ethoxy)phenyl)pyridine-3,5-dicarbonitrile 2-({(2-(4-chlorophenyl)-1,3-thiazol-4-yl)methyl}thio)-6-(ethyl(methyl)amino)-4-(4-(2-hydroxy-ethoxy)phenyl)pyridine-3,5-dicarbonitrile 2-({(2-(4-chlorophenyl)-1,3-thiazol-4-yl)methyl}thio)-6-(diethylamino)-4-(4-(2-hydroxy-ethoxy)phenyl)pyridine-3,5-dicarbonitrile 2-({(2-(4-chlorophenyl)-1,3-thiazol-4-yl)methyl}thio)-4-(4-(2-hydroxyethoxy)phenyl)-6-(isopropylamino)pyridine-3,5-dicarbonitrile 2-azetidin-1-yl-6-({(2-(4-chlorophenyl)-1,3-thiazol-4-yl)methyl}thio)-4-(4-(2-hydroxyethoxy)phenyl)pyridine-3,5-dicarbonitrile 2-({(2-(4-chlorophenyl)-1,3-thiazol-4-yl)methyl}sulfanyl)-6-(cyclopropylamino)-4-(4-(2-hydroxyethoxy)phenyl)pyridine-3,5-dicarbonitrile 2-({(2-(4-chlorophenyl)-1,3-thiazol-4-yl)methyl}sulfanyl)-6-(cyclobutylamino)-4-(4-(2-hydroxyethoxy)phenyl)pyridine-3,5-dicarbonitrile 2-({(2-(4-chlorophenyl)-1,3-thiazol-4-yl)methyl}sulfanyl)-4-(4-(2-hydroxyethoxy)phenyl)-6-((3,3,3-trifluoropropyl)amino)pyridine-3,5-dicarbonitrile 2-({(2-(4-chlorophenyl)-1,3-thiazol-4-yl)methyl}sulfanyl)-4-(4-(2-hydroxyethoxy)phenyl)-6-(propylamino)pyridine-3,5-dicarbonitrile 2-({(2-(4-chlorophenyl)-1,3-thiazol-4-yl)methyl}sulfanyl)-4-(4-(2-hydroxyethoxy)phenyl)-6-(piperidin-1-yl)pyridine-3,5-dicarbonitrile 2-({(2-(4-chlorophenyl)-1,3-thiazol-4-yl)methyl}sulfanyl)-4-(4-(2-hydroxyethoxy)phenyl)-6-((3-methylbutyl)amino)pyridine-3,5-dicarbonitrile 2-(azepan-1-yl)-6-({(2-(4-chlorophenyl)-1,3-thiazol-4-yl)methyl}sulfanyl)-4-(4-(2-hydroxyethoxy)phenyl)pyridine-3,5-dicarbonitrile 2-({(2-(4-chlorophenyl)-1,3-thiazol-4-yl)methyl}sulfanyl)-4-(4-(2-hydroxyethoxy)phenyl)-6-(4-methylpiperidin-1-yl)pyridine-3,5-dicarbonitrile 2-({(2-(4-chlorophenyl)-1,3-thiazol-4-yl)methyl}sulfanyl)-4-(4-(2-hydroxyethoxy)phenyl)-6-(morpholin-4-yl)pyridine-3,5-dicarbonitrile 2-({(2-(4-chlorophenyl)-1,3-thiazol-4-yl)methyl}sulfanyl)-6-(4,4-dimethylpiperidin-1-yl)-4-(4-(2-hydroxyethoxy)phenyl)pyridine-3,5-dicarbonitrile 2-({(2-(4-chlorophenyl)-1,3-thiazol-4-yl)methyl}sulfanyl)-6-((2,2-difluoroethyl)(methyl)amino)-4-(4-(2-hydroxyethoxy)phenyl)pyridine-3,5-dicarbonitrile 2-({(2-(4-chlorophenyl)-1,3-thiazol-4-yl)methyl}sulfanyl)-4-(4-(2-hydroxyethoxy)phenyl)-6-(methyl(propyl)amino)pyridine-3,5-dicarbonitrile 2-({(2-(4-chlorophenyl)-1,3-thiazol-4-yl)methyl}sulfanyl)-4-(4-(2-hydroxyethoxy)phenyl)-6-((2-methoxyethyl)(methyl)amino)pyridine-3,5-dicarbonitrile 2-({(2-(4-chlorophenyl)-1,3-thiazol-4-yl)methyl}sulfanyl)-4-(4-(2-hydroxyethoxy)phenyl)-6-((2-methoxyethyl)amino)pyridine-3,5-dicarbonitrile 2-({(2-(4-chlorophenyl)-1,3-thiazol-4-yl)methyl}sulfanyl)-6-((2-ethoxyethyl)amino)-4-(4-(2-hydroxyethoxy)phenyl)pyridine-3,5-dicarbonitrile 2-({(2-(4-chlorophenyl)-1,3-thiazol-4-yl)methyl}sulfanyl)-4-(4-(2-hydroxyethoxy)phenyl)-6-(4-methoxypiperidin-1-yl)pyridine-3,5-dicarbonitrile 2-({(2-(4-chlorophenyl)-1,3-thiazol-4-yl)methyl}sulfanyl)-6-((3R)-3-ethoxypyrrolidin-1-yl)-4-(4-(2-hydroxyethoxy)phenyl)pyridine-3,5-dicarbonitrile 2-({(2-(4-chlorophenyl)-1,3-thiazol-4-yl)methyl}sulfanyl)-6-(3,3-difluoropyrrolidin-1-yl)-4-(4-(2-hydroxyethoxy)phenyl)pyridine-3,5-dicarbonitrile 2-({(2-(4-chlorophenyl)-1,3-thiazol-4-yl)methyl}sulfanyl)-6-(4,4-difluoropiperidin-1-yl)-4-(4-(2-hydroxyethoxy)phenyl)pyridine-3,5-dicarbonitrile 2-({(2-(4-chlorophenyl)-1,3-thiazol-4-yl)methyl}sulfanyl)-4-(4-(2-hydroxyethoxy)phenyl)-6-(4-(trifluormethyl)piperidin-1-yl)pyridine-3,5-dicarbonitrile 2-({(2-(4-chlorophenyl)-1,3-thiazol-4-yl)methyl}sulfanyl)-6-(3,3-difluorazetidin-1-yl)-4-(4-(2-hydroxyethoxy)phenyl)pyridine-3,5-dicarbonitrile 2-({(2-(4-chlorophenyl)-1,3-thiazol-4-yl)methyl}sulfanyl)-4-(4-(2-hydroxyethoxy)phenyl)-6-(3-methoxyazetidin-1-yl)pyridine-3,5-dicarbonitrile 2-({(2-(4-chlorophenyl)-1,3-thiazol-4-yl)methyl}sulfanyl)-6-(3,3-difluoropiperidin-1-yl)-4-(4-(2-hydroxyethoxy)phenyl)pyridine-3,5-dicarbonitrile 2-({(2-(4-chlorophenyl)-1,3-thiazol-4-yl)methyl}sulfanyl)-4-(4-(2-hydroxyethoxy)phenyl)-6-((2,2,2-trifluoroethyl)amino)pyridine-3,5-dicarbonitrile 2-({(2-(4-chlorophenyl)-1,3-thiazol-4-yl)methyl}sulfanyl)-6-((2-fluoroethyl)amino)-4-(4-(2-hydroxyethoxy)phenyl)pyridine-3,5-dicarbonitrile 2-({(2-(4-chlorophenyl)-1,3-thiazol-4-yl)methyl}sulfanyl)-6-((2,2-difluoroethyl)amino)-4-(4-(2-hydroxyethoxy)phenyl)pyridine-3,5-dicarbonitrile 2-({(2-(4-chlorophenyl)-1,3-thiazol-4-yl)methyl}sulfanyl)-4-(4-(2-hydroxyethoxy)phenyl)-6-(methyl(2,2,2-trifluoroethyl)amino)pyridine-3,5-dicarbonitrile 2-({(2-(4-chlorophenyl)-1,3-thiazol-4-yl)methyl}sulfanyl)-6-(ethyl(2,2,2-trifluoroethyl)amino)-4-(4-(2-hydroxyethoxy)phenyl)pyridine-3,5-dicarbonitrile 2-{4-(2-(azetidin-1-yl)-6-({(2-(4-chlorophenyl)-1,3-thiazol-4-yl)methyl}sulfanyl)-3,5-dicyanopyridin-4-yl)phenoxy}ethyl eta-alanyl-L-alaninate 2-{4-(2-({(2-(4-chlorophenyl)-1,3-thiazol-4-yl)methyl}sulfanyl)-3,5-dicyano-6-(propyl-amino)pyridin-4-yl)phenoxy}ethyl L-alaninate trifluoroacetate 2-{4-(2-({(2-(4-chlorophenyl)-1,3-thiazol-4-yl)methyl}sulfanyl)-3,5-dicyano-6-(methyl-amino)pyridin-4-yl)phenoxy}ethyl L-alaninate trifluoroacetate 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-alaninate trifluoroacetate 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-lysyl-L-alaninate dihydrochloride 2-{4-(2-({(2-(4-chlorophenyl)-1,3-thiazol-4-yl)methyl}sulfanyl)-3,5-dicyano-6-(methylamino)pyridin-4-yl)phenoxy}ethyl L-lysyl-L-alaninate dihydrochloride 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-lysyl-beta-alaninate dihydrochloride 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-alanyl-L-alaninate hydrochloride 2-{4-(2-(azetidin-1-yl)-6-({(2-(4-chlorophenyl)-1,3-thiazol-4-yl)methyl}sulfanyl)-3,5-dicyanopyridin-4-yl)phenoxy}ethyl L-alaninate trifluoroacetate 2-{4-(2-(azetidin-1-yl)-6-({(2-(4-chlorophenyl)-1,3-thiazol-4-yl)methyl}sulfanyl)-3,5-dicyanopyridin-4-yl)phenoxy}ethyl L-lysyl-L-alaninate bistrifluoroacetate 2-{4-(2-({(2-(4-chlorophenyl)-1,3-thiazol-4-yl)methyl}sulfanyl)-3,5-dicyano-6-(propylamino)pyridin-4-yl)phenoxy}ethyl L-ornithinate bistrifluoroacetate 2-{4-(2-(azetidin-1-yl)-6-({(2-(4-chlorophenyl)-1,3-thiazol-4-yl)methyl}sulfanyl)-3,5-dicyanopyridin-4-yl)phenoxy}ethyl L-ornithinate bistrifluoroacetate 2-{4-(2-(azetidin-1-yl)-6-({(2-(4-chlorophenyl)-1,3-thiazol-4-yl)methyl}sulfanyl)-3,5-dicyanopyridin-4-yl)phenoxy}ethyl beta-alaninate trifluoroacetate 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl beta-alaninate trifluoroacetate 2-{4-(2-({(2-(4-chlorophenyl)-1,3-thiazol-4-yl)methyl}sulfanyl)-3,5-dicyano-6-(propylamino)pyridin-4-yl)phenoxy}ethyl L-alanyl-L-alaninate trifluoroacetate 2-{4-(2-({(2-(4-chlorophenyl)-1,3-thiazol-4-yl)methyl}sulfanyl)-3,5-dicyano-6-(methylamino)pyridin-4-yl)phenoxy}ethyl L-ornithinate bistrifluoroacetate 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-alanyl-beta-alaninate trifluoroacetate 2-{4-(2-({(2-(4-chlorophenyl)-1,3-thiazol-4-yl)methyl}sulfanyl)-3,5-dicyano-6-(propylamino)pyridin-4-yl)phenoxy}ethyl L-lysyl-L-alaninate bistrifluoroacetate 2-{4-(2-({(2-(4-chlorophenyl)-1,3-thiazol-4-yl)methyl}sulfanyl)-3,5-dicyano-6-(propylamino)pyridin-4-yl)phenoxy}ethyl beta-alanyl-L-alaninate trifluoroacetate 2-{4-(2-({(2-(4-chlorophenyl)-1,3-thiazol-4-yl)methyl}sulfanyl)-3,5-dicyano-6-(methylamino)pyridin-4-yl)phenoxy}ethyl beta-alaninate trifluoroacetate 2-{4-(2-({(2-(4-chlorophenyl)-1,3-thiazol-4-yl)methyl}sulfanyl)-3,5-dicyano-6-(methylamino)pyridin-4-yl)phenoxy}ethyl L-alanyl-L-alaninate trifluoroacetate 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-ornithyl-L-alaninate bistrifluoroacetate 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-ornithinate bistrifluoroacetate 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl beta-alanyl-L-alaninate trifluoroacetate 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl beta-alanyl-L-alaninate hydrochloride 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-prolyl-L-alaninate hydrochloride 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-isoleucyl-L-alaninate hydrochloride 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl N-((2S)-2,4-diaminobutanoyl)-L-alaninate dihydrochloride 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-histidyl-L-alaninate dihydrochloride 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-arginyl-L-alaninate dihydrochloride 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl 3-amino-L-alanyl-L-alaninate bistrifluoroacetate 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-alanyl-L-leucinate hydrochloride 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl beta-alanyl-L-leucinate hydrochloride 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl glycyl-L-leucinate hydrochloride, and the N-oxides, salts, solvates, salts of the N-oxides and solvates of the N-oxides and salts thereof.

The present invention furthermore provides a process for preparing the compounds of the formula (I) according to the invention in which $R^3$ represents hydrogen, characterized in that the compound of the formula (II)

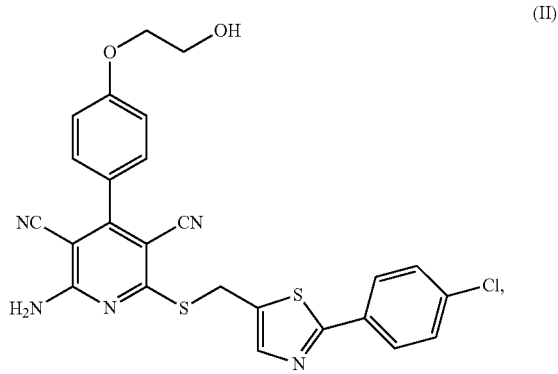 [SMILES: N#Cc1c(N)nc(SCc2cnc(-c3ccc(Cl)cc3)s2)c(C#N)c1-c1ccc(OCCO)cc1]

is initially converted with copper(II) chloride and isoamyl nitrite in a suitable solvent into the compound of the formula (III)

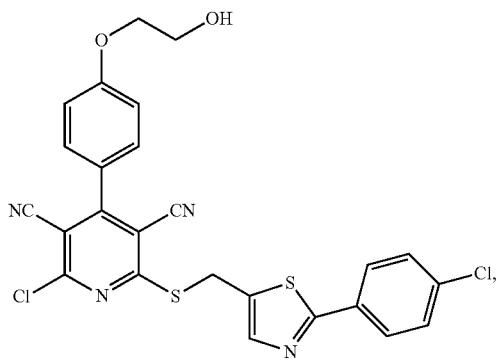

and this is then, in an inert solvent, if appropriate in the presence of a suitable base, reacted with a compound of the formula (IV)

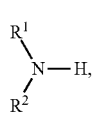

in which $R^1$ and $R^2$ each have the meanings given above, to give a compound of the formula (I-A)

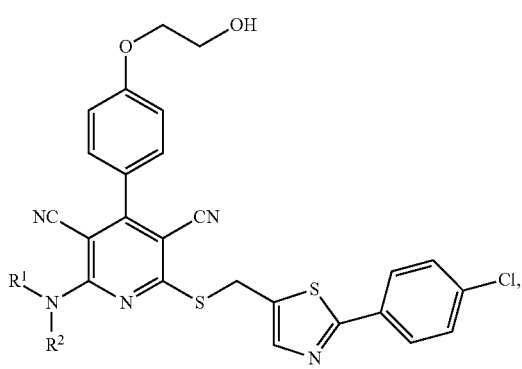

in which $R^1$ and $R^2$ each have the meanings given above, any protective groups present are then removed and the resulting compounds of the formula (I) are, if appropriate, converted with the appropriate (i) solvents and/or (ii) bases or acids into their solvates, salts and/or solvates of the salts.

The process described above can be illustrated in an exemplary manner by reaction scheme 1 as shown in FIG. 1.

Suitable solvents for the reaction (III)+(IV) are all organic solvents which are inert under the reaction conditions. These include ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulfoxide (DMSO), N-methylpyrrolidinone (NMP), acetonitrile or pyridine. It is also possible to use mixtures of the solvents mentioned above. Preference is given to using tetrahydrofuran and dimethylformamide.

Suitable bases for this reaction are the customary inorganic or organic bases. These preferably include alkali metal carbonates, such as lithium carbonate, sodium carbonate, potassium carbonate or cesium carbonate, alkali metal bicarbonates, such as sodium bicarbonate or potassium bicarbonate, or organic amines, such as triethylamine, diisopropylethylamine, pyridine, 1,8-diazabicyclo(5.4.0)undec-7-ene (DBU) or 1,5-diazabicyclo(4.3.0)non-5-ene (DBN), and also phosphazene bases ("Schwesinger bases"), such as, for example, P2-t-Bu or P4-t-Bu. Preference is given to cesium carbonate, triethylamine and diisopropylethylamine.

The reaction (III)+(IV) is generally carried out in a temperature range of from −78° C. to +140° C., preferably in the range from −20° C. to +100° C., if appropriate in a microwave. The reaction can take place under atmospheric, elevated or reduced pressure (for example in the range from 0.5 to 5 bar). In general, the reaction is carried out at atmospheric pressure.

The process step (II)→(III) is generally carried out using a molar ratio of from 2 to 12 mol of copper(II) chloride and from 2 to 12 mol of isoamyl nitrite per mole of the compound of the formula (II-A).

Suitable solvents for this process step are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichlorethane and chlorobenzene, or other solvents, such as dimethylformamide, acetonitrile or pyridine. It is also possible to use mixtures of these solvents. Preferred solvents are acetonitrile and dimethylformamide.

The reaction is generally carried out in a temperature range of from −78° C. to +180° C., preferably in the range from +20° C. to +100° C., in particular at from +20° C. to +60° C., if appropriate in a microwave. The reaction can take place under atmospheric, elevated or reduced pressure (for example in the range from 0.5 to 5 bar). In general, the reaction is carried out under atmospheric pressure.

The compound of the formula (II) can be prepared as described in WO 03/053441 for Example 6.

The compounds of the formula (IV) are commercially available or known from the literature or can be prepared by methods known from the literature.

The present invention furthermore provides a process for preparing the compounds of the formula (I) according to the invention in which $R^3$ represents a group of the formula

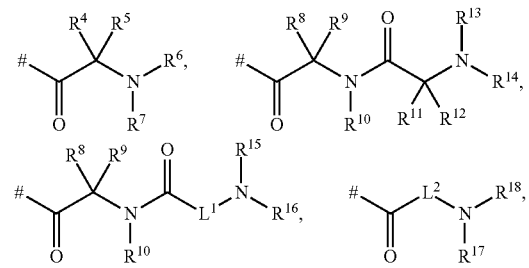

-continued

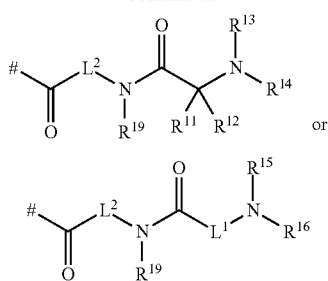

where $L^1$, $L^2$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ each have the meanings given above, characterized in that (A) a compound of the formula (I-A)

(I-A)

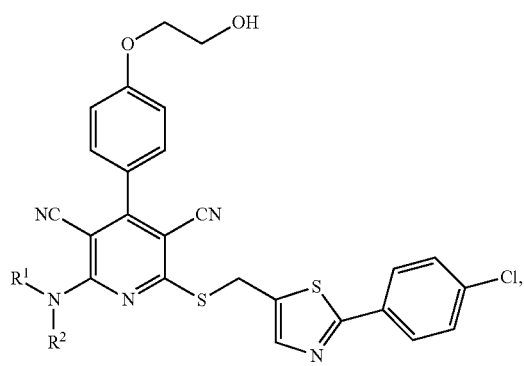

in which $R^1$ and $R^2$ each have the meanings given above, is initially coupled in an inert solvent in the presence of a condensing agent with a carboxylic acid of the formula (V) or (VI)

(V)

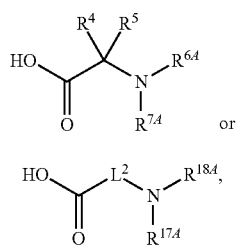

(VI)

in which $L^2$, $R^4$ and $R^5$ each have the meanings given above and $R^{6A}$, $R^{7A}$, $R^{17A}$ and $R^{18A}$ each have the meanings mentioned for $R^6$, $R^7$, $R^{17}$ and $R^{18}$, respectively, or represent an amino protective group, such as, for example, tert-butoxycarbonyl, to give a compound of the formula (VII) or (VIII)

(VII)

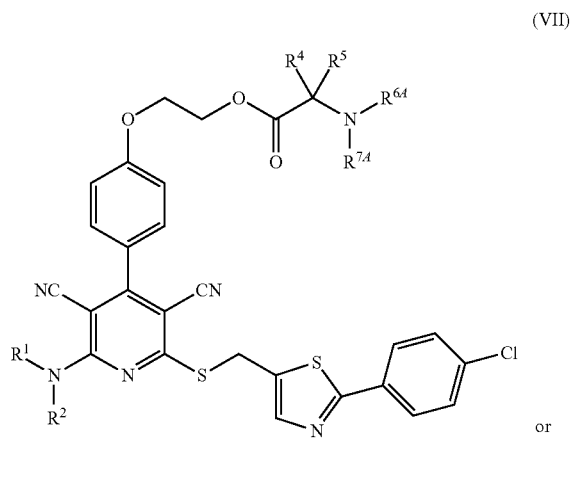

or (VIII)

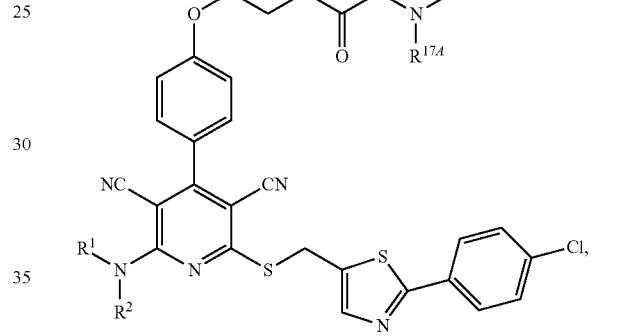

in which $L^2$, $R^1$, $R^2$, $R^4$, $R^5$, $R^{6A}$, $R^{7A}$, $R^{17A}$ and $R^{18A}$ each have the meanings given above, and any protective groups present are then removed to give a compound of the formula (I-B) or (I-C)

(I-B)

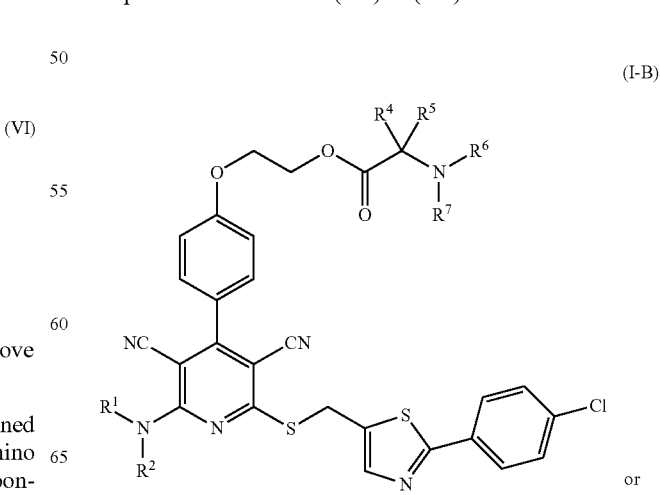

or

-continued

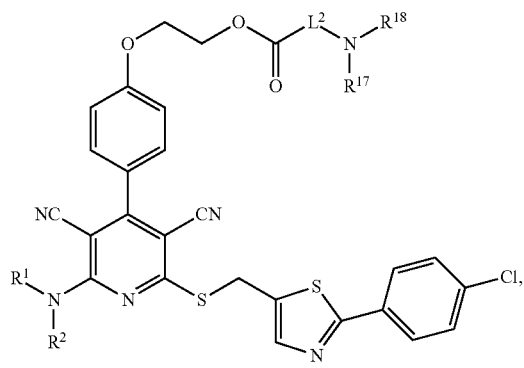
(I-C)

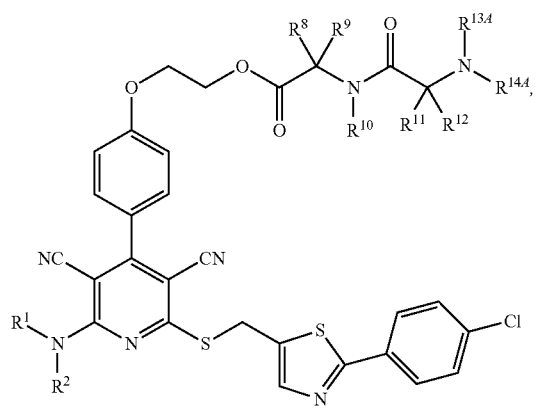
(XIII)

in which $L^2$, $R^1$, $R^2$, $R^4$, $R^5$, $R^6$, $R^7$, $R^{17}$ and $R^{18}$ each have the meanings given above, or (B) a compound of the formula (I-A) is initially coupled in an inert solvent in the presence of a condensing agent with a carboxylic acid of the formula (IX), (X), (XI) or (XII)

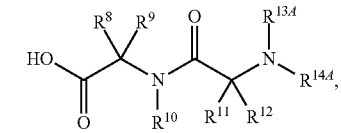
(IX)

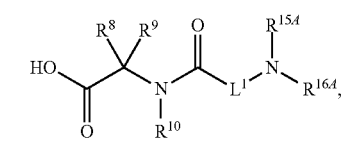
(X)

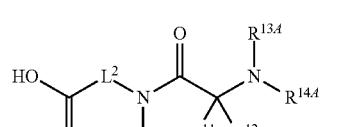
(XI)

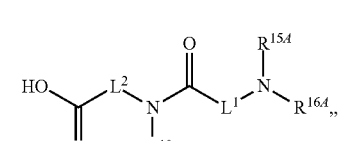
or

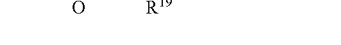
(XII)

in which $L^1$, $L^2$, $R^8$, $R^9$, $R^{10}$, $R^{11}$, $R^{12}$ and $R^{19}$ each have the meanings given above and $R^{13A}$, $R^{14A}$, $R^{15A}$ and $R^{16A}$ each have the meanings mentioned for $R^{13}$, $R^{14}$, $R^{15}$ and $R^{16}$, respectively, or represent an amino protective group, such as, for example, tert-butoxycarbonyl, to give a compound of the formula (XIII), (XIV), (XV) or (XVI)

(XIV)

(XV)

(XVI)

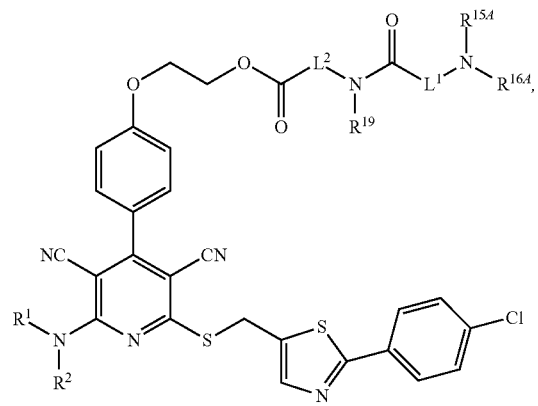

in which $L^1$, $L^2$, $R^1$, $R^2$, $R^8$, $R^9$, $R^{10}$, $R^{11}$, $R^{12}$, $R^{13A}$, $R^{14A}$, $R^{15A}$, $R^{16A}$ and $R^{19}$ each have the meanings given above, and any protective groups present are then removed to give a compound of the formula (I-D), (I-E), (I-F) or (I-G)

(I-D)

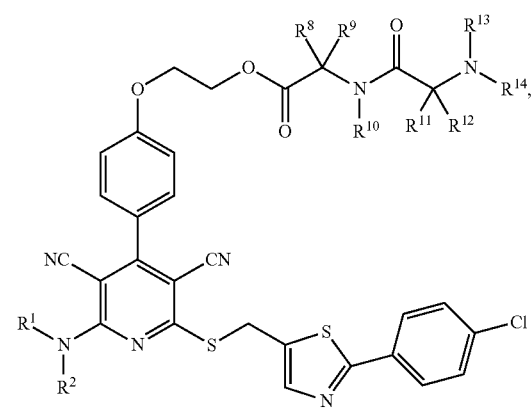

(I-E)

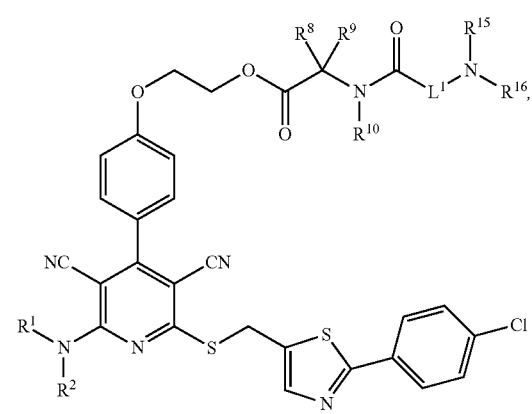

(I-F)

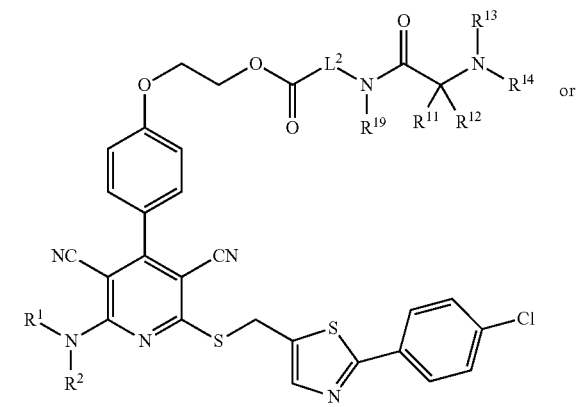

or (I-G)

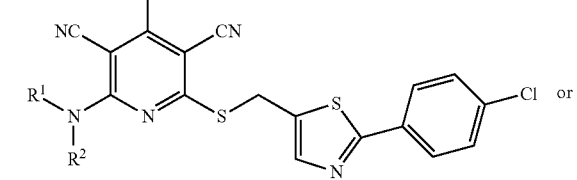

in which $L^1$, $L^2$, $R^1$, $R^2$, $R^8$, $R^9$, $R^{10}$, $R^{11}$, $R^{12}$, $R^{13}$, $R^{14}$, $R^{15}$, $R^{16}$ and $R^{19}$ each have the meanings given above, or (C) the amino protective group is removed from a compound of the formula (VII-1) or (VIII-1)

(VII-1)

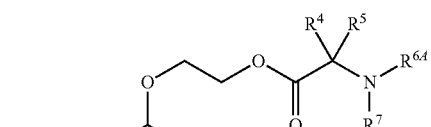 or (VIII-1)

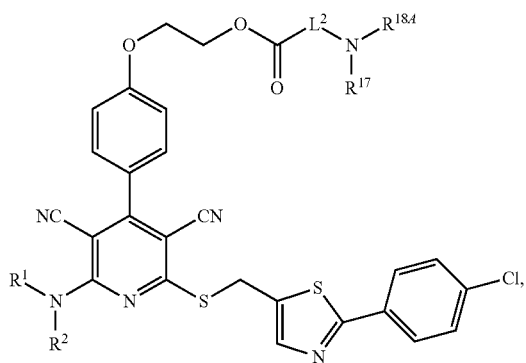

in which $L^2$, $R^1$, $R^2$, $R^4$, $R^5$, $R^7$ and $R^{17}$ each have the meanings given above,
and
$R^{6A}$ and $R^{18A}$ represent an amino protective group, for example tert-butoxycarbonyl,
by standard methods to give a compound of the formula (I-B-1) or (I-C-1)

(I-B-1)

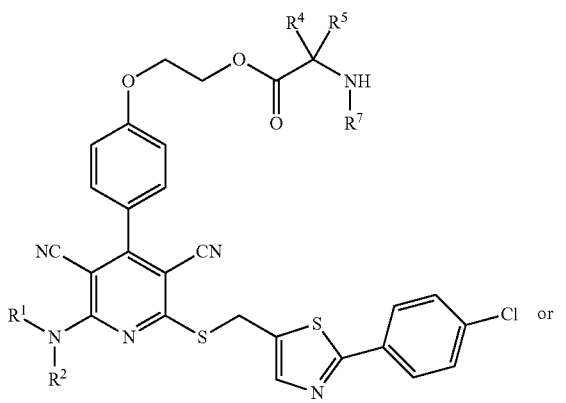

or (I-C-1)

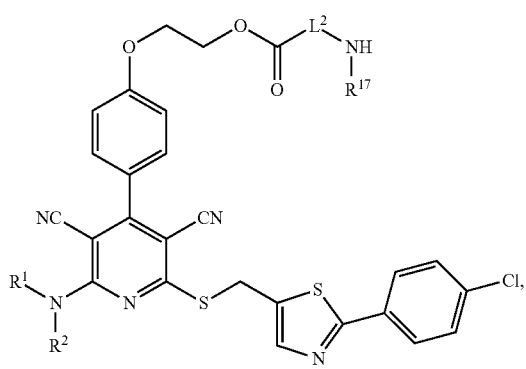

in which $L^2$, $R^1$, $R^2$, $R^4$, $R^5$, $R^7$ and $R^{17}$ each have the meanings given above,
and these are initially coupled in an inert solvent in the presence of a condensing agent with a carboxylic acid of the formula (XVII) or (XVIII)

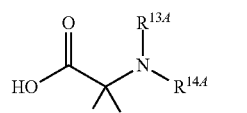
(XVII)

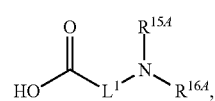
(XVIII)

in which $L^1$, $R^{11}$ and $R^{12}$ each have the meanings given above and
$R^{13A}$, $R^{14A}$, $R^{15A}$ and $R^{16A}$ each have the meanings mentioned for $R^{13}$, $R^{14}$, $R^{15}$ and $R^{16}$, respectively, or represent an amino protective group, such as, for example, tert-butoxycarbonyl, to give compounds of the formula (XIII), (XIV), (XV) or (XVI), and any protective groups present are then removed again to give the resulting compounds (I-D), (I-E), (I-F) or (I-G), and the resulting compounds of the formula (I-B), (I-C), (I-D), (I-E), (I-F) and (I-G) are, if appropriate, converted with the appropriate (I) solvents and/or (ii) bases or acids into their solvates, salts and/or solvates of the salts.

The transformation (I-A)→(I-B), (I-C), (I-D), (I-E), (I-F) or (I-G) thus takes place either by direct acylation with a suitably protected dipeptoid derivative (process variant (B)) or by sequential coupling of the individual, if appropriate suitable protected, amino acid components (process variant (C)). The coupling reactions (ester or amide formation) are in this case carried out by known methods of peptide chemistry (cf., for example, M. Bodanszky, *Principles of Peptide Synthesis*, Springer-Verlag, Berlin, 1993; H.-D. Jakubke and H. Jeschkeit, *Aminosäuren, Peptide, Proteine* (Amino Acids, Peptides, Proteins), Verlag Chemie, Weinheim, 1982).

Examples of inert solvents for the coupling reactions are ethers such as diethyl ether, tert-butyl methyl ether, dioxane, tetrahydrofuran, glycol dimethyl ether or diethylene glycol dimethyl ether, hydrocarbons such as benzene, toluene, xylene, hexane, cyclohexane or petroleum fractions, halohydrocarbons such as dichloromethane, trichloromethane, tetrachloromethane, 1,2-dichloroethane, trichloroethylene or chlorobenzene, or other solvents such as acetone, ethyl acetate, pyridine, dimethyl sulfoxide, dimethylformamide, N,N'-dimethylpropyleneurea (DMPU), N-methylpyrrolidone (NMP) or acetonitrile. It is likewise possible to use mixtures of the solvents mentioned. Dichloromethane, dimethylformamide or mixtures of these two solvents are preferred.

Examples of suitable condensing agents in these coupling reactions are carbodiimides such as N,N'-diethyl-N,N'-dipropyl-N,N'-diisopropyl-N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride, diethyl cyanophosphonate, bis-(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzothiazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2'-1)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), where appropriate in combination with further auxiliaries such as 1-hydroxybenzotriazole (HOBt) or N-hydroxysuccinimide (HOSu), and as bases are alkali metal carbonates, e.g. sodium or potassium carbonate, or organic amine bases such as triethylamine, N-methylmorpholine, N-methylpiperidine, N,N-diisopropylethylamine or 4-N,N-dimethylaminopyridine. N-(3-Dimethylaminoisopropyl)-N'-ethylcarbodiimide hydrochloride (EDC) in combination with 4-N,N-dimethylaminopyridine is preferably employed for ester formation. N-(3-Dimethylaminoisopropyl)-N'-ethylcarbodiimide hydrochloride (EDC) in combination with 1-hydroxybenzotriazole (HOBt) or N-hydroxysuccinimide (HOSu) and, where appropriate, a base such as N,N-diisopropylethylamine is preferably used for amide formation.

The couplings are generally carried out in a temperature range of from 0° C. to +60° C., preferably from +10° C. to +30° C. The reactions can take place under atmospheric, under elevated or under reduced pressure (for example from 0.5 to 5 bar). They are generally carried out under atmospheric pressure.

The compounds of the formula (I) may also result directly in the form of salts in the preparation by the processes described above. These salts can be converted where appropriate by treatment with a base or acid in an inert solvent, by chromatographic methods or by ion exchanger resins, into the respective free bases or acids. Further salts of the compounds according to the invention can also be prepared where appropriate by exchange of counterions by means of ion exchange chromatography, for example with Amberlite® resins.

In the reaction sequences described above, any functional groups which may be present in the compounds of the formulae (V), (VI), (IX), (X), (XI), (XII), (XVII) and (XVIII) or in the radicals $R^4$, $R^6$, $R^7$, $R^{13}$, $R^{14}$, $R^{15}$, $R^{16}$, $R^{17}$ and/or $R^{18}$—such as, in particular, amino, guanidino, hydroxyl, mercapto and carboxyl groups—may, if expedient or required, also be present in temporarily protected form. The introduction and removal of such protective groups takes place in this connection by conventional methods known from peptide chemistry (see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984).

The amino and guanidine protective group which is preferably used is tert-butoxycarbonyl (Boc) or benzyloxycarbonyl (Z). The protective group preferably employed for a hydroxyl or carboxyl function is preferably tert-butyl or benzyl. Elimination of these protective groups is carried out by conventional methods, preferably by reaction with a strong acid such as hydrogen chloride, hydrogen bromide or trifluoroacetic acid in an inert solvent such as dioxane, diethyl ether, dichloromethane or acetic acid; the elimination can where appropriate also take place without an additional inert solvent. In the case of benzyl and benzyloxycarbonyl as protective group, these can also be removed by hydrogenolysis in the presence of a palladium catalyst. Elimination of the protective groups mentioned may where appropriate be carried out simultaneously in a one-pot reaction or in separate reaction steps.

To produce defined salt stoichiometries and for removing solvent residues, the compounds according to the invention can be stirred as a suspension in organic solvents at room temperature. Stirring at room temperature in isopropanol or diethyl ether for several days is preferred. Particular preference is given to stirring at room temperature in isopropanol for 7 days. The compounds according to the invention are subsequently filtered off and dried.

The compounds of the formulae (V), (VI), (IX), (X), (XI), (XII), (XVII) and (XVIII) are commercially available or known from the literature, or they can be prepared by methods customary in the literature.

The compounds of the formulae (VII), (VII-1), (VIII), (VIII-1), (XIII), (XIV), (XV) and (XVI) are novel and thus also form part of the subject matter of the present invention, the substituents having the meanings given above.

Figure 2:
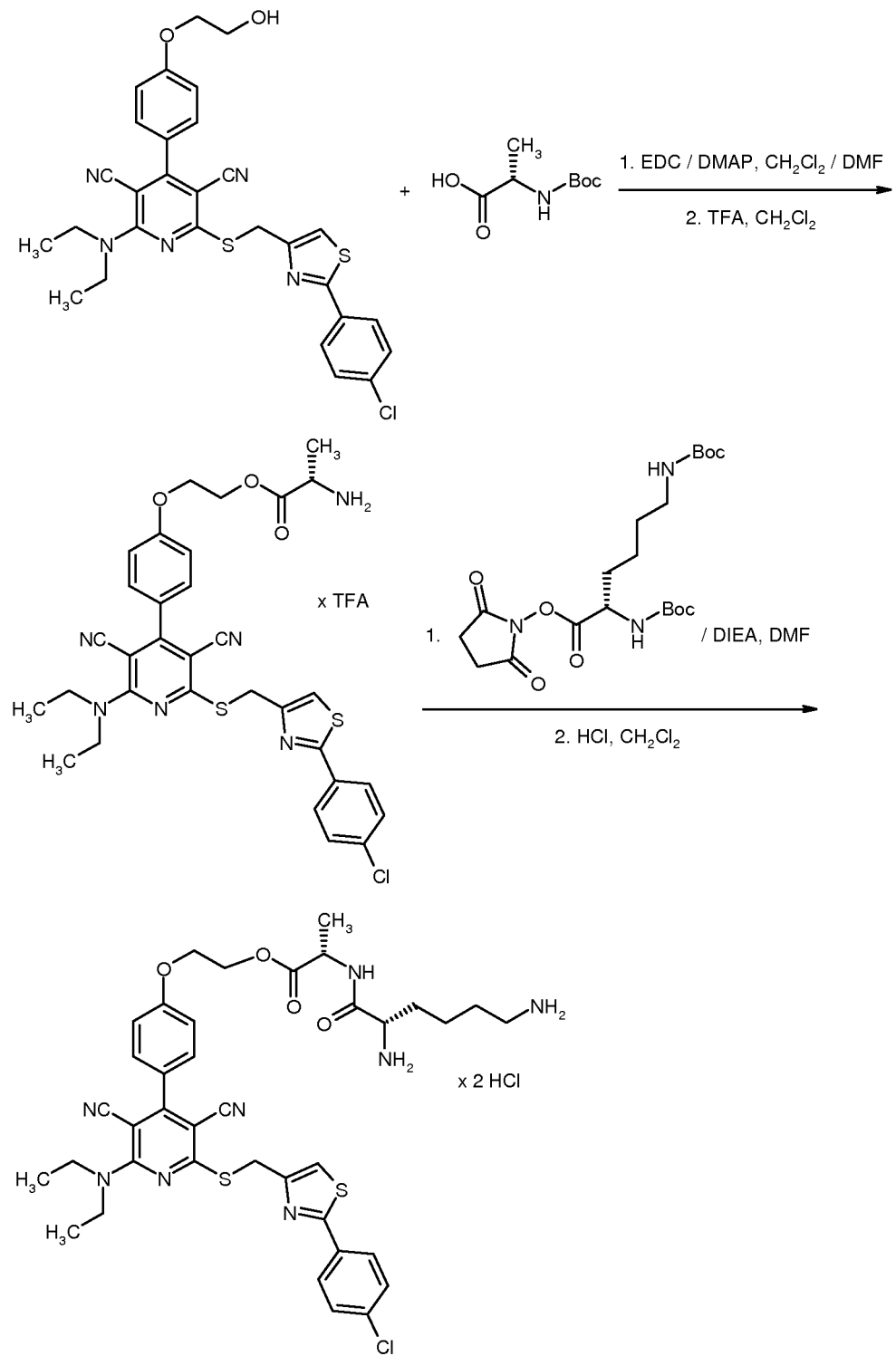
FIG. 2 is Scheme 2 for preparing the compounds of the formula (I).
Figure 3:
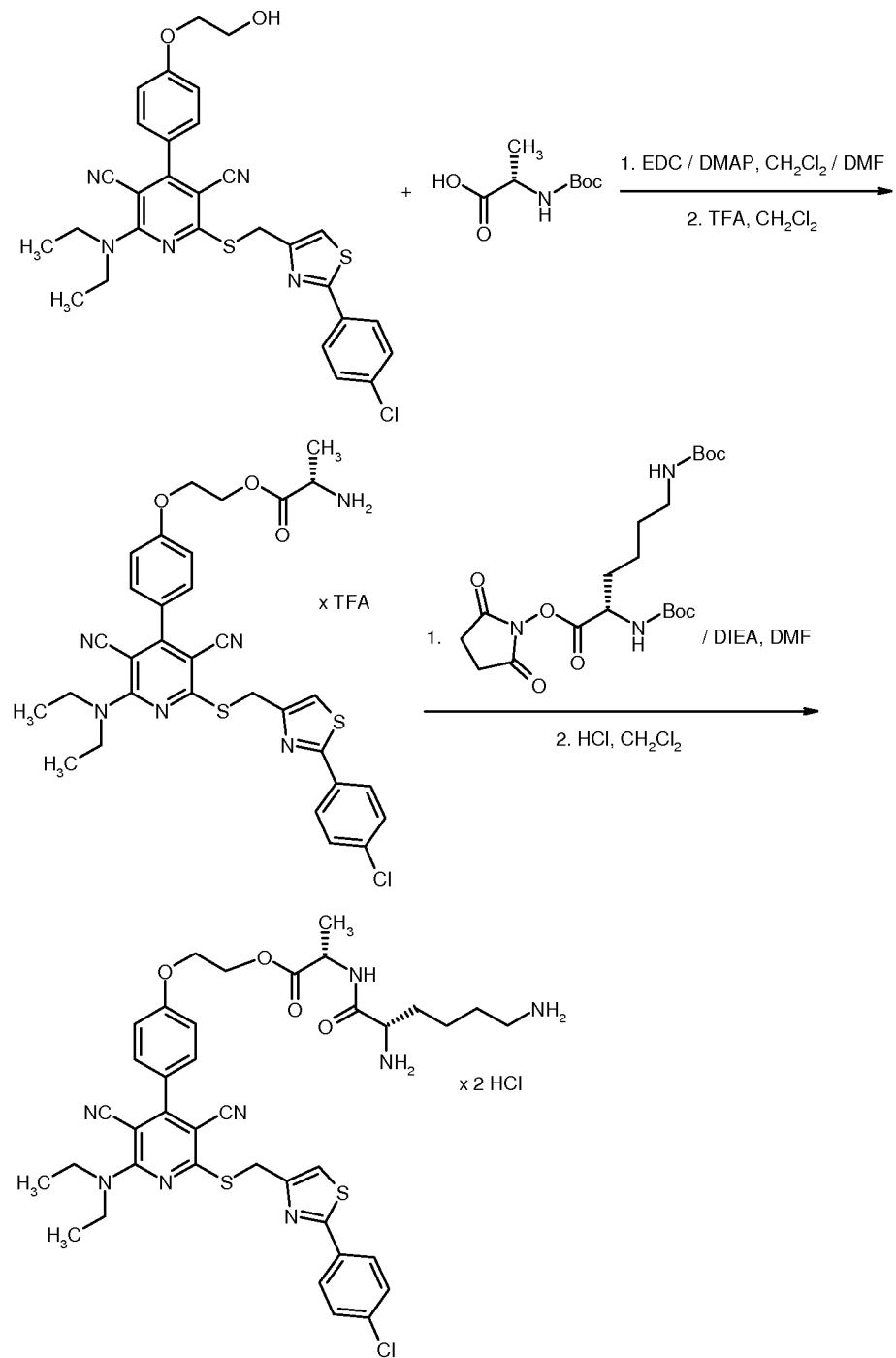
FIG. 3 is Scheme 3 for preparing the compounds of the formula (I).

The preparation of the compounds according to the invention can be illustrated by the synthesis schemes 2 and 3, as respectively shown in FIGS. 2 and 3.

Surprisingly, the compounds according to the invention have an unforeseeable useful pharmacological activity spectrum and are therefore particularly suitable for the prophylaxis and/or treatment of disorders.

The pharmaceutical activity of the compounds according to the invention can be explained by their action as potent, selective ligands at adenosine A1 and/or A2b receptors. Here, they act as selective A1 agonists or as selective dual A1/A2b agonists. The compounds according to the invention have an advantageous therapeutic and/or pharmacological activity profile.

In the context of the present invention, "selective ligands at adenosine A1 and/or A2b receptors" are adenosine receptor ligands where firstly a marked activity at A1 and/or A2b adenosine receptor subtypes and secondly no or a considerably weaker activity (by a factor of 10 or more) at A2a and A3 adenosine receptor subtypes can be observed, where with respect to the test methods for activity/selectivity, reference is made to the tests described in section B-1.

Depending on their particular structure, the compounds according to the invention can act as full or as partial adenosine receptor agonists. Partial adenosine receptor agonists are defined here as receptor ligands which trigger a functional response at adenosine receptors which is less than that of full agonists (such as, for example, adenosine itself). Accordingly, partial agonists have lower activity with respect to receptor activation than full agonists.

The compounds according to the invention and their salts of the formula (I) in which $R^3$ is not hydrogen represent useful prodrugs of the active ingredient compounds of the formula (I) in which $R^3$ represents hydrogen. Firstly, they have good stability at various pH values, and secondly they are, at a physiological pH and in particular in vivo, efficiently converted into the active ingredient compound of the formula (I) in which $R^3$ represents hydrogen. The prodrugs according to the invention moreover have improved solubilities in aqueous or other physiologically tolerated media, making them suitable for therapeutic use, in particular on intravenous administration. In addition, the bioavailability from suspension after oral administration is improved by comparison with the active ingredient compounds of the formula (I) in which $R^3$ represents hydrogen.

The compounds of the formula (I) are suitable alone or in combination with one or more other active ingredients for the prophylaxis and/or treatment of various disorders, for example disorders of the cardiovascular system (cardiovascular disorders), for cardio protection following lesions of the heart, and of metabolic disorders and kidney disorders.

Disorders of the cardiovascular system, or cardiovascular disorders, mean in the context of the present invention for example the following disorders: hypertension (high blood pressure), peripheral and cardiac vascular disorders, coronary heart disease, coronary restenosis such as, for example, restenosis following balloon dilatation of peripheral blood vessels, myocardial infarction, acute coronary syndrome, acute coronary syndrome with ST elevation, acute coronary syndrome without ST elevation, stable and unstable angina pectoris, myocardial insufficiency, princemetal angina, persistent ischemic dysfunction ("hibernating myocardium"), temporary postischemic dysfunction ("stunned myocardium"), heart failure, tachycardia, atrial tachycardia, arrhythmias, atrial and ventricular fibrillation, persistent atrial fibrillation, permanent atrial fibrillation, atrial fibrillation with normal left ventricular function, atrial fibrillation with impaired left ventricular function, Wolff-Parkinson-White syndrome, disturbances of peripheral blood flow, elevated levels of fibrinogen and of low density LDL, and elevated concentrations of plasminogen activator inhibitor 1 (PAI-1), especially coronary heart disease, acute coronary syndrome, angina pectoris, heart failure, myocardial infarction and atrial fibrillation.

In the context of the present invention, the term heart failure includes both acute and chronic manifestations of heart failure, as well as more specific or related types of disease, such as acute decompensated heart failure, right heart failure, left heart failure, global failure, ischemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure and acute phases of worsening heart failure.

The compounds according to the invention are further also suitable for reducing the area of myocardium affected by an infarction, and for the prophylaxis of secondary infarctions.

The compounds according to the invention are furthermore suitable for the prophylaxis and/or treatment of thromboembolic disorders, reperfusion damage following ischemia, micro- and macrovascular lesions (vasculitis), arterial and venous thromboses, edemas, ischemias such as myocardial infarction, stroke and transient ischemic attacks, for cardio protection in connection with coronary artery bypass operations (CABG), primary percutaneous transluminal coronary angioplasties (PTCAs), PTCAs after thrombolysis, rescue PTCA, heart transplants and open-heart operations, and for organ protection in connection with transplants, bypass operations, catheter examinations and other surgical procedures.

Other areas of indication for which the compounds according to the invention can be employed are, for example, the prevention and/or treatment of disorders of the urogenital tract, such as, for example, irritable bladder, erectile dysfunction and female sexual dysfunction, but in addition also the prevention and/or treatment of inflammatory disorders, such as, for example, inflammatory dermatoses (psoriasis, acne, eczema, neurodermitis, dermatitis, keratitis, formation of scars, formation of warts, frostbites), of disorders of the central nervous system and neurodegenerative disorders (strokes, Alzheimer's disease, Parkinson's disease, dementia, epilepsy, depression, multiple sclerosis), of states of pain, cancerous diseases (skin cancer, liposarcomas, carcinomas of the gastrointestinal tract, the liver, pancreas, lung, kidney, ureter, prostate and the genital tract), and also of nausea and emesis associated with cancer therapies.

Other areas of indication are, for example, the prevention and/or treatment of inflammatory and immune disorders (Crohn's disease, ulcerative colitis, lupus erythematodes, rheumatoid arthritis) and respiratory disorders, such as, for example, chronic obstructive pulmonary disease (chronic bronchitis, COPD), asthma, pulmonary emphysema, bronchiectases, cystic fibrosis (mucoviscidosis) and pulmonary hypertension, in particular pulmonary arterial hypertension.

Finally, the compounds according to the invention are also suitable for the prevention and/or treatment of diabetes, in particular diabetes mellitus, gestation diabetes, insulin-dependent diabetes and non-insulin-dependent diabetes, of diabetic sequelae such as, for example, retino-pathy, nephropathy and neuropathy, of metabolic disorders (metabolic syndrome, hyperglycemia, gestation diabetes, hyperinsulinemia, insulin resistance, glucose intolerance, obesity (adipositas)) and also of arteriosclerosis and dyslipidemias (hypercholesterolemia, hypertriglyceridemia, elevated concentrations of postprandial plasma triglycerides, hypoalphalipoproteinemia, combined hyperlipidemias), in particular of diabetes, metabolic syndrome and dyslipidemias.

In addition, the compounds according to the invention can also be used for the treatment and/or prevention of disorders of the thyroid gland (hyperthyreosis), disorders of the pancreas (pancreatitis), fibrosis of the liver, viral diseases (HPV, HCMV, HIV), cachexia, osteoporosis, gout, incontinence, and also for wound healing and angiogenesis.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides a method for the treatment and/or prevention of disorders, in particular the disorders mentioned above, using an effective amount of at least one compound according to the invention.

The present invention furthermore provides the compounds according to the invention for use in a method for the treatment and/or prophylaxis of coronary heart disease, acute coronary syndrome, angina pectoris, heart failure, myocardial infarction and atrial fibrillation.

The present invention furthermore provides the compounds according to the invention for methods for the treatment and/or prophylaxis of diabetes, metabolic syndrome and dyslipidemias.

The compounds according to the invention can be used alone or, if required, in combination with other active compounds. The present invention furthermore provides medicaments comprising at least one compound according to the invention and one or more further active ingredients, in particular for the treatment and/or prevention of the disorders mentioned above.

Suitable active ingredients for combination are, by way of example and by way of preference: active ingredients which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, LTB4-receptor antagonists), analgesics for example aspirin, antidepressants and other psychopharmaceuticals.

The present invention relates in particular to combinations of at least one of the compounds according to the invention with at least one lipid metabolism-altering active ingredient, antidiabetic, blood pressure reducing active ingredient and/or agent having antithrombotic effects.

The compounds according to the invention can preferably be combined with one or more lipid metabolism-modulating active ingredients, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers;

antidiabetics mentioned in the Rote Liste 2004/II, chapter 12, and also, by way of example and by way of preference, those from the group of the sulfonylureas, biguanides, meglitinide derivatives, glucosidase inhibitors, inhibitors of dipeptidyl-peptidase IV (DPP-IV inhibitors), oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861;

hypotensive active ingredients, by way of example and by way of preference from the group of the calcium antagonists, angiotensin AII antagonists, ACE inhibitors, renin inhibitors, beta-receptor blockers, alpha-receptor blockers, aldosterone antagonists, mineralocorticoid receptor antagonists, ECE inhibitors, ACE/NEP inhibitors and the vasopeptidase inhibitors; and/or antithrombotic agents, by way of example and by way of preference from the group of the platelet aggregation inhibitors or the anticoagulants;

diuretics;

vasopressin receptor antagonists;

organic nitrates and NO donors;

compounds with positive inotropic activity;

compounds which inhibit the degradation of cyclic guanosine monophosphate (cGMP) and/or cyclic adenosine monophosphat (cAMP), such as, for example, inhibitors of phos-phodiesterases (PDE) 1, 2, 3, 4 and/or 5, in particular PDE 5 inhibitors, such as sildena-fil, vardena-fil and tadalafil, and also PDE 3 inhibitors, such as milrinone;

natriuretic peptides, such as, for example, "atrial natriuretic peptide" (ANP, anaritide), "B-type natriuretic peptide" or "brain natriuretic peptide" (BNP, nesiritide), "C-type natriuretic peptide" (CNP) and also urodilatin;

agonists of the prostacyclin receptor (IP receptor), such as, by way of example, iloprost, beraprost, cicaprost;

inhibitors of the $I_f$(funny channel) channel, such as, by way of example, ivabradine;

calcium sensitizers, such as, by way of example and by way of preference, levosimendan;

potassium supplements;

NO-independent, but heme-dependent stimulators of guanylate cyclase, such as, in particular, the compounds described in WO 00/06568, WO 00/06569, WO 02/42301 and WO 03/095451;

NO- and heme-independent activators of guanylate cyclase, such as, in particular, the compounds described in WO 01/19355, WO 01/19776, WO 01/19778, WO 01/19780, WO 02/070462 and WO 02/070510;

inhibitors of human neutrophil elastase (HNE), such as, for example, sivelestat and DX-890 (Reltran);

compounds which inhibit the signal transduction cascade, such as, for example, tyrosine-kinase inhibitors, in particular sorafenib, imatinib, gefitinib and erlotinib; and/or compounds which modulate the energy metabolism of the heart, such as, for example, etomoxir, dichloroacetate, ranolazine and trimetazidine.

Lipid metabolism-modifying active ingredients are to be understood as meaning, preferably, compounds from the group of the HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists PPAR-γ agonists, PPAR-δ agonists, polymeric bile acid adsorbers, bile acid reabsorption inhibitors, antioxidants/radical scavengers and also the cannabinoid receptor 1 antagonists.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, such as, by way of example and by way of preference, BMS-188494 or TAK-475.

In a preferred embodiment of the invention, the compounds according to the invention are administered in combination with an ACAT inhibitor, such as, by way of example and by way of preference, avasimibe, melinamide, pactimibe, eflucimibe or SMP-797.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with an MTP inhibitor, such as, by way of example and by way of preference, implitapide, BMS-201038, R-103757 or JTT-130.

In a preferred embodiment of the invention, the compounds according to the invention are administered in combination with a lipase inhibitor, such as, by way of example and by way of preference, orlistat.

In a preferred embodiment of the invention, the compounds according to the invention are administered in combination with a thyroid hormone and/or thyroid mimetic, such as, by way of example and by way of preference, D-thyroxine or 3,5,3'-triiodothyronine (T3).

In a preferred embodiment of the invention, the compounds according to the invention are administered in combination with an agonist of the niacin receptor, such as, by way of example and by way of preference, niacin, acipimox, acifran or radecol.

In a preferred embodiment of the invention, the compounds according to the invention are administered in combination with a CETP inhibitor, such as, by way of example and by way of preference, dalcetrapib, BAY 60-5521, anacetrapib or CETP vaccine (CETi-1).

In a preferred embodiment of the invention, the compounds according to the invention are administered in combination with a PPAR-γ agonist, for example from the class of the thiazolidinediones, such as, by way of example and by way of preference, pioglitazone or rosiglitazone.

In a preferred embodiment of the invention, the compounds according to the invention are administered in combination with a PPAR-δ agonist, such as, by way of example and by way of preference, GW-501516 or BAY 68-5042.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as, by way of example and by way of preference, probucol, AGI-1067, BO-653 or AEOL-10150.

In a preferred embodiment of the invention, the compounds according to the invention are administered in combination with a cannabinoid receptor 1 antagonist, such as, by way of example and by way of preference, rimonabant or SR-147778.

Antidiabetics are to be understood as meaning, preferably, insulin and insulin derivatives, and also orally effective hypoglycemic active ingredients. Here, insulin and insulin derivatives include both insulins of animal, human or biotechnological origin and also mixtures thereof. The orally effective hypoglycemic active ingredients preferably include sulfonylureas, biguanides, meglitinide derivatives, glucosidase inhibitors and PPAR-gamma agonists.

In a preferred embodiment of the invention, the compounds according to the invention are administered in combination with insulin.

In a preferred embodiment of the invention, the compounds according to the invention are administered in combination with a sulfonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin.

In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a glucosidase inhibitor, such as, by way of example and by way of preference, miglitol or acarbose.

In a preferred embodiment of the invention, the compounds according to the invention are administered in combination with a DPP-IV inhibitor, such as, by way of example and by way of preference, sitagliptin and vildagliptin.

In a preferred embodiment of the invention, the compounds according to the invention are administered in combination with a PPAR-gamma agonist, for example from the class of the thiazolinediones, such as, by way of example and by way of preference, pioglitazone or rosiglitazone.

The hypotensive agents are preferably understood as meaning compounds from the group of the calcium antagonists, angiotensin AII antagonists, ACE inhibitors, beta-receptor blockers, alpha-receptor blockers and diuretics.

In a preferred embodiment of the invention, the compounds according to the invention are administered in combination with a calcium antagonist, such as, by way of example and by way of preference, nifedipine, amlodipine, verapamil or diltiazem.

In a preferred embodiment of the invention, the compounds according to the invention are administered in combination with an angiotensin AII antagonist, such as, by way of example and by way of preference, losartan, valsartan, candesartan, embusartan, olmesartan or telmisartan.

In a preferred embodiment of the invention, the compounds according to the invention are administered in combination with an ACE inhibitor, such as, by way of example and by way of preference, enalapril, captopril, lisinopril, ramipril, delapril, fosinopril, quinopril, perindopril or trandopril.

In a preferred embodiment of the invention, the compounds according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-receptor blocker, such as, by way of example and by way of preference, prazosin.

In a preferred embodiment of the invention, the compounds according to the invention are administered in combination with a diuretic, such as, by way of example and by way of preference, furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride or triamteren.

In a preferred embodiment of the invention, the compounds according to the invention are administered in combination with an aldosterone or mineralocorticoid receptor antagonist, such as, by way of example and by way of preference, spironolactone or eplerenone.

In a preferred embodiment of the invention, the compounds according to the invention are administered in combination with a vasopressin receptor antagonist, such as, by way of example and by way of preference, conivaptan, tolvaptan, lixivaptan or SR-121463.

In a preferred embodiment of the invention, the compounds according to the invention are administered in combination with an organic nitrate or NO donor, such as, by way of example and by way of preference, sodium nitroprusside, nitroglycerol, isosorbide mononitrate, isosorbide dinitrate, molsidomin or SIN-1, or in combination with inhalative NO.

In a preferred embodiment of the invention, the compounds according to the invention are administered in combination with a positive-inotropic compound, such as, by way of example and by way of preference, cardiac glycosides (digoxin), beta-adrenergic and dopaminergic agonists, such as isoproterenol, adrenaline, noradrenaline, dopamine or dobutamine.

In a preferred embodiment of the invention, the compounds according to the invention are administered in combination with antisympathotonics, such as reserpine, clonidine or alpha-methyldopa, or in combination with potassium channel agonists, such as minoxidil, diazoxide, dihydralazine or hydralazine, or with substances which release nitrogen oxide, such as glycerol nitrate or sodium nitroprusside.

Antithrombotics are to be understood as meaning, preferably, compounds from the group of the platelet aggregation inhibitors or the anticoagulants.

In a preferred embodiment of the invention, the compounds according to the invention are administered in combination with a platelet aggregation inhibitor, such as, by way of example and by way of preference, aspirin, clopidogrel, ticlopidine or dipyridamol.

In a preferred embodiment of the invention, the compounds according to the invention are administered in combination with a thrombin inhibitor, such as, by way of example and by way of preference, ximelagatran, melagatran, dabigatran, bivalirudin or clexane.

In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as, by way of example and by way of preference, coumarin.

In the context of the present invention, particular preference is given to combinations comprising at least one of the compounds according to the invention and also one or more further active ingredients selected from the group consisting of HMG-CoA reductase inhibitors (statins), diuretics, beta-receptor blockers, organic nitrates and NO donors, ACE inhibitors, angiotensin AII antagonists, aldosterone and mineralocorticoid receptor antagonists, vasopressin receptor antagonists, platelet aggregation inhibitors and anticoagulants, and also their use for the treatment and/or prevention of the disorders mentioned above.

The present invention furthermore provides medicaments comprising at least one compound according to the invention, usually together with one or more inert nontoxic pharmaceutically suitable auxiliaries, and also their use for the purposes mentioned above.

The compounds according to the invention can act systemically and/or locally. For this purpose, they can be administered in a suitable manner, such as, for example, orally, parenterally, pulmonally, nasally, sublingually, lingually, buccally, rectally, dermally, transdermally, conjunctivally, otically or as an implant or stent.

For these administration routes, the compounds according to the invention can be administered in suitable administration forms.

Suitable for oral administration are administration forms which work in accordance with the prior art and release the compounds according to the invention rapidly and/or in modified form and which comprise the compounds according to the invention in crystalline and/or amorphicized and/or dissolved form, such as, for example, tablets (uncoated or coated tablets, for example with enteric coats or coats which dissolve in a delayed manner or are insoluble and which control the release of the compound according to the invention), films/wafers or tablets which dissolve rapidly in the oral cavity, films/lyophilizates, capsules (for example hard or soft gelatin capsules), sugar-coated tablets, granules, pellets, powders, emulsions, suspensions, aerosols or solutions.

Parenteral administration may take place by circumventing a bioabsorption step (for example intravenously, intraarterially, intracardially, intraspinally or intralumbarly), or with bioabsorption (for example intramuscularly, subcutaneously, intracutaneously, percutaneously or intraperitoneally). Administration forms suitable for parenteral administration are inter alia preparations for injection or infusion in the form of solutions, suspensions, emulsions, lyophilizates or sterile powders.

Suitable for other administration routes are, for example, medicaments suitable for inhalation (inter alia powder inhalers, nebulizers), nose drops, solutions or sprays, tablets to be administered lingually, sublingually or buccally, films/wafers or capsules, suppositories, preparations to be administered to ears or eyes, vaginal capsules, aqueous suspensions (lotions, shaking mixtures), lipophilic suspensions, ointments, creams, transdermal therapeutic systems (for example plasters), milk, pastes, foams, powders for pouring, implants or stents.

Preference is given to oral or parenteral administration, in particular to oral and intravenous administration.

The compounds according to the invention can be converted into the administration forms mentioned. This can be carried out in a manner known per se by mixing with inert non-toxic pharmaceutically suitable auxiliaries. These auxiliaries include inter alia carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides), and flavor and/or odor corrigents.

In general, it has been found to be advantageous in the case of parenteral administration to administer amounts of about 0.001 to 1 mg/kg, preferably about 0.01 to 0.5 mg/kg of body weight to obtain effective results. In the case of oral administration, the dosage is from about 0.01 to 100 mg/kg, preferably from about 0.01 to 20 mg/kg and very particularly preferably from 0.1 to 10 mg/kg of body weight.

In spite of this, it may be necessary to deviate from the amounts mentioned, namely depending on body weight, administration route, individual response to the active ingredient, the type of preparation and the time or the interval at which administration takes place. Thus, in some cases it may be sufficient to administer less than the abovementioned minimum amount, whereas in other cases the upper limit mentioned has to be exceeded. In the case of the administration of relatively large amounts, it may be expedient to divide these into a plurality of individual doses which are administered over the course of the day.

The working examples below illustrate the invention. The invention is not limited to the examples.

The percentages in the tests and examples below are, unless indicated otherwise, percentages by weight; parts are parts by weight. Solvent ratios, dilution ratios and concentrations of liquid/liquid solutions are in each case based on volume.

A. EXAMPLES

Abbreviations Used aq. aqueous
Ex. Example
c concentration
d doublett (in NMR)
dd doublet of doublets (in NMR)
DBU 1,8-diazabicyclo(5.4.0)undec-7-ene
TLC thin-layer chromatography
DCI direct chemical ionization (in MS)
DMF N,N-dimethylformamide
DMSO dimethyl sulfoxide
ee enantiomeric excess
EI electron impact ionization (in MS)
ESI electrospray ionization (in MS)
Et ethyl
m.p. melting point
h hour(s)
HPLC high-pressure, high-performance liquid chromatography
cat. catalytic
conc. concentrated
LC-MS liquid chromatography-coupled mass spectrometry
lit. literature (reference)
Me methyl
MeCN acetonitrile
min minute(s)
MS mass spectrometry
NMM N-methylmorpholine
NMR nuclear magnetic resonance spectrometry
q quartet (in NMR)
rac. racemic
RP-HPLC reversed-phase HPLC
RT room temperature
$R_t$ retention time (in HPLC)
singlet (in NMR)
br broad singlet (in NMR)
triplet (in NMR)
t-Bu tert-butyl
TFA trifluoroacetic acid
THF tetrahydrofuran
dil. dilute
HPLC, LC-MS and GC-MS Methods:
Method 1 (LC-MS):
Instrument: Micromass Quattro Micro MS with HPLC Agilent Series 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 2 (LC-MS):
Instrument: Waters ACQUITY SQD UPLC System; column: Waters Acquity UPLC HSS T3 1.8μ 50×1 mm; mobile phase A: 1 l of water+0.25 ml 99% strength formic acid, mobile phase B: 1 l of acetonitrile+0.25 ml 99% strength formic acid; gradient: 0.0 min 90% A→1.2 min 5% A→2.0 min 5% A; oven: 50° C.; flow rate: 0.40 ml/min; UV detection: 210-400 nm.

Method 3 (LC-MS):
MS instrument type: Micromass Quattro LCZ; HPLC instrument type: HP 1100 Series; UV DAD; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 4 (LC-MS):
Instrument: Micromass QuattroPremier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 5 (LC-MS):
MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 6 (LC-MS):
MS instrument type: Micromass ZQ; HPLC instrument type: HP 1100 Series; UV DAD; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 7 (LC-MS):
MS instrument type: Micromass ZQ; HPLC instrument type: Waters Alliance 2795; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 8 (LC-MS):
MS instrument type: Micromass ZQ; HPLC instrument type: Waters Alliance 2795; column: Merck Chromolith SpeedROD RP-18e 100×4.6 mm; mobile phase A: 1 l of water+0.5 ml of 50% strength formic acid; mobile phase B: 1 l of acetonitrile+0.5 ml of 50% strength formic acid; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm Starting Materials and Intermediates:

Example 1A

2-Amino-6-({(2-(4-chlorophenyl)-1,3-thiazol-4-ylmethyl}sulfanyl)-4-(4-(2-hydroxyethoxy)phenyl)pyridine-3,5-dicarbonitrile

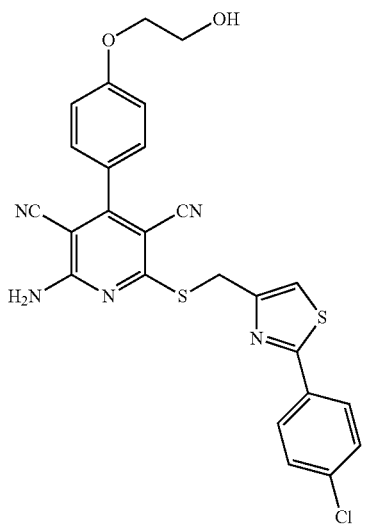 [SMILES: N#Cc1c(N)nc(SCc2csc(-c3ccc(Cl)cc3)n2)c(C#N)c1-c1ccc(OCCO)cc1]

The preparation was described in WO 03/053441, Example 6.
LC-MS (Method 8): $R_t$=5.69 min; MS (ESIpos): m/z=520 (M+H)$^+$.

Example 2A

2-Chloro-6-({(2-(4-chlorophenyl)-1,3-thiazol-4-ylmethyl}sulfanyl)-4-(4-(2-hydroxyethoxy)phenyl)pyridine-3,5-dicarbonitrile

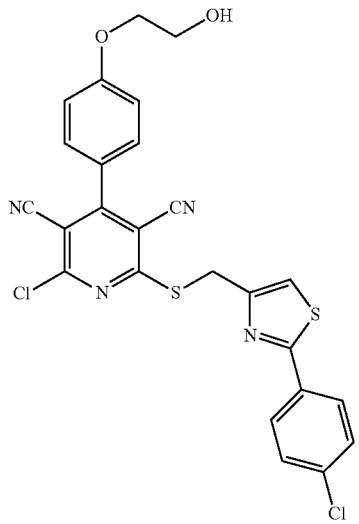 [SMILES: N#Cc1c(Cl)nc(SCc2csc(-c3ccc(Cl)cc3)n2)c(C#N)c1-c1ccc(OCCO)cc1]

15.00 g (28.84 mmol) of 2-amino-6-({(2-(4-chlorophenyl)-1,3-thiazol-4-yl)methyl}sulfanyl)-4-(4-(2-hydroxyethoxy)phenyl)pyridine-3,5-dicarbonitrile (Example 1A) were initially charged in 200 ml of acetonitrile, and 6.76 g (57.69 mmol) of isopentyl nitrite and 7.76 g (57.69 mmol) of copper(II) chloride were added. The mixture was stirred at 70° C. for 6 h. After cooling to RT, 750 ml of 1N hydrochloric acid were added and the mixture was stirred for 30 min. The aqueous phase was extracted three times with ethyl acetate. The combined organic phases were dried over sodium sulfate. After removal of the solvent, the crude product was purified by column chromatography on silica gel (mobile phase: toluene/ethyl acetate 4:1). This gave 10.8 g (69% of theory, purity 90%) of the desired target compound. For further purification, the product may, if appropriate, be triturated with diethyl ether.
LC-MS (Method 2): $R_t$=1.36 min; MS (ESIpos): m/z=539 (M+H)$^+$.
$^1$H-NMR (400 MHz, DMSO-d$_6$): δ=7.95 (d, 2H), 7.75 (s, 1H), 7.61 (d, 2H), 7.57 (d, 2H), 7.18 (d, 2H), 4.77 (s, 2H), 4.10 (t, 2H), 3.75 (t, 2H).

Example 3A

2-{4-(2-(Azetidin-1-yl)-6-({(2-(4-chlorophenyl)-1,3-thiazol-4-yl)methyl}sulfanyl)-3,5-dicyanopyridin-4-yl)phenoxy}ethyl N$^2$,N$^6$-bis(tert-butoxycarbonyl)-L-lysyl-L-alaninate

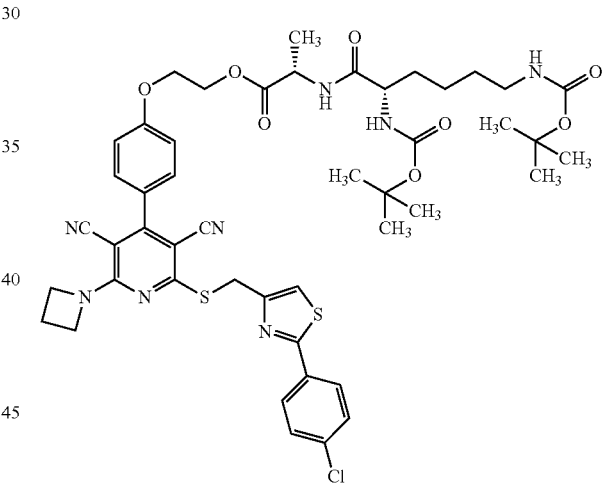

32.73 mg (0.094 mmol) of N$^2$,N$^6$-bis(tert-butoxycarbonyl)-L-lysine were initially charged in 1.5 ml of DMF. 19.8 mg (0.103 mmol) of 1-(3-dimethylaminopropyl)-3-ethylcarbodiimide hydrochloride, 17.4 mg (0.129 mmol) of 1-hydroxy-1H-benzotriazole hydrate and 55.5 mg (0.429 mmol) of N,N-diisopropylethylamine were added, and the mixture was then stirred at RT for 15 min, 64 mg (0.086 mmol) of 2-{4-(2-(azetidin-1-yl)-6-({(2-(4-chlorophenyl)-1,3-thiazol-4-ylmethyl}sulfanyl)-3,5-dicyanopyridin-4-yl)phenoxy}ethyl L-alaninate trifluoroacetate (Example 45) were then added and the mixture was stirred at RT overnight. The crude product was purified by preparative HPLC (acetonitrile/water+0.1% TFA). This gave 76 mg (92% of theory) of the target compound.
LC-MS (Method 6): $R_t$=3.30 min; MS (ESIpos): m/z=959 (M+H)$^+$.
The examples listed in Table 1 were prepared analogously to Example 3A from the appropriate starting materials.

TABLE 1

| Example No. | Structure | LC-MS: R$_t$ (min) (Method); MS (ESI): m/z (M + H)$^+$ |
|---|---|---|
| 4A | (structure) (49% of theory) *1 | 1.62 min (Method 4); m/z = 802 |
| 5A | (structure) (94% of theory) *1 | 1.68 min (Method 4); m/z = 804 |

TABLE 1-continued

| Example No. | Structure | LC-MS: $R_t$ (min) (Method); MS (ESI): m/z $(M + H)^+$ |
|---|---|---|
| 6A | 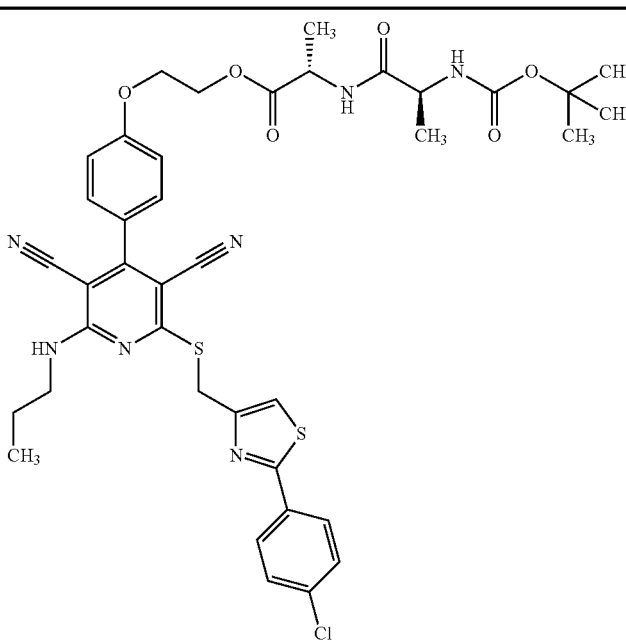 (97% of theory) *1 | 1.70 min (Method 4); m/z = 704 $(M + H—Boc)^+$ |

*1 purification; before the reaction solution was applied to preparative HPLC, a little water/THF or water/acetonitrile was added to the reaction solution such that a clear solution was obtained.

Example 7A

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl N-(tert-butoxycarbonyl)-L-alanyl-L-alaninate

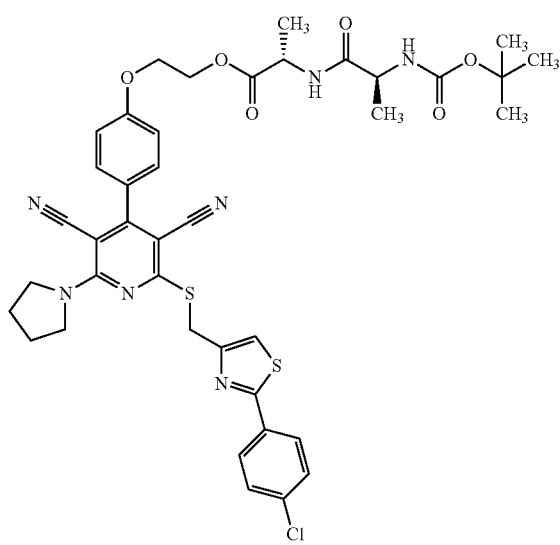 [SMILES: C[C@H](NC(=O)OC(C)(C)C)C(=O)N[C@@H](C)C(=O)OCCOc1ccc(-c2c(C#N)c(SCc3csc(-c4ccc(Cl)cc4)n3)nc(N3CCCC3)c2C#N)cc1]

26.756 g (141.406 mmol) of N-(tert-butoxycarbonyl)-L-alanine together with 29.572 g (154.261 mmol) of 1-(3-dimethylaminopropyl)-3-ethylcarbodiimide hydrochloride, 29.529 g (192.827 mmol) of 1-hydroxy-1H-benzotriazole hydrate and 55.979 ml (321.378 mmol) of N,N-diisopropylethylamine were dissolved in 10 l DMF. 97.60 g (128.551 mmol) of trifluoroacetic acid-2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl L-alaninate (1:1) were then added, and the mixture was stirred at room temperature for 3 h. The reaction mixture was stirred into water and extracted with dichloromethane. The organic phase was washed with water, dried over sodium sulfate, filtered and concentrated. The residue was triturated with diethyl ether, and the solid was filtered off with suction and air-dried. This gave 95 g (91% of theory) of the desired target compound.

LC-MS (Method 2): $R_t$=1.49 min; MS (ESIpos): m/z=816 $(M+H)^+$.

$^1$H-NMR (400 MHz, DMSO-$d_6$): δ=8.21 (d, 1H), 7.95 (d, 2H), 7.70 (s, 1H), 7.58 (d, 2H), 7.48 (d, 2H), 7.11 (d, 2H), 6.84 (d, 1H), 4.70 (s, 2H), 4.46-4.32 (m, 2H), 4.31-4.24 (m, 3H), 4.03-3.93 (m, 1H), 3.97-3.79 (m, 4H), 2.01-1.88 (m, 4H) 1.36 (s, 9H), 1.29 (d, 3H), 1.16 (d, 3H).

The examples listed in Table 6 were prepared analogously to Example 3A from the appropriate starting materials.

TABLE 6
| Example No. | Structure | LC-MS: R$_t$ (min) (Method); MS (ESI): m/z (M + H)$^+$ |
|---|---|---|
| 8A | 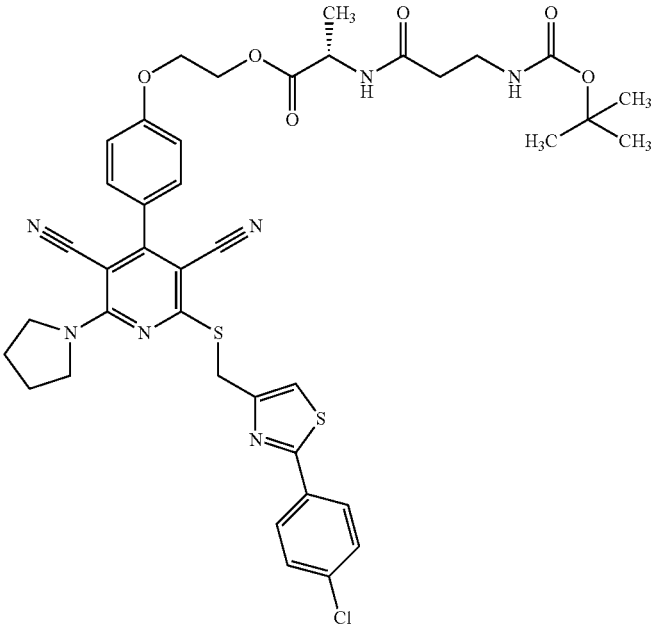 [SMILES: C[C@H](NC(=O)CCNC(=O)OC(C)(C)C)C(=O)OCCOc1ccc(-c2c(C#N)c(SCc3csc(-c4ccc(Cl)cc4)n3)nc(N3CCCC3)c2C#N)cc1]<br>(53% of theory)<br>*1 | 1.69 min (Method 4); m/z = 816 |
| 9A | 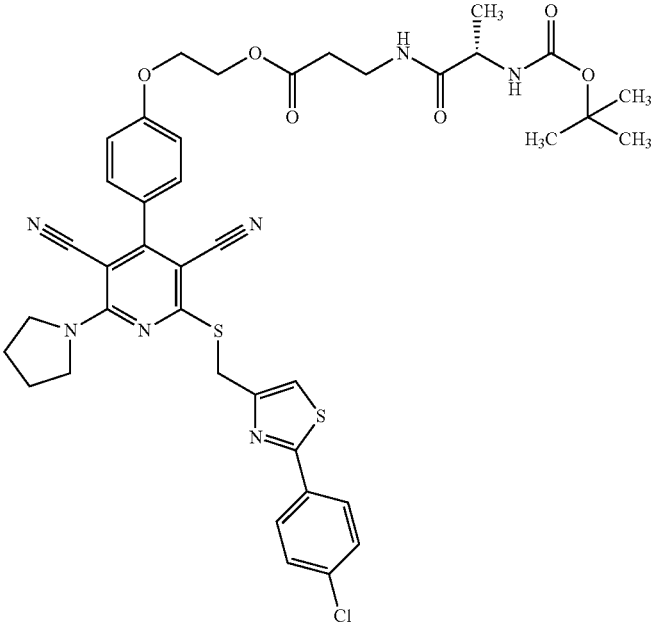 [SMILES: C[C@H](NC(=O)OC(C)(C)C)C(=O)NCCC(=O)OCCOc1ccc(-c2c(C#N)c(SCc3csc(-c4ccc(Cl)cc4)n3)nc(N3CCCC3)c2C#N)cc1]<br>(88% of theory)<br>*1 | 1.68 min (Method 4); m/z = 716 (M + H—Boc)$^+$ |

TABLE 6-continued

| Example No. | Structure | LC-MS: $R_t$ (min) (Method); MS (ESI): m/z $(M + H)^+$ |
|---|---|---|
| 10A | 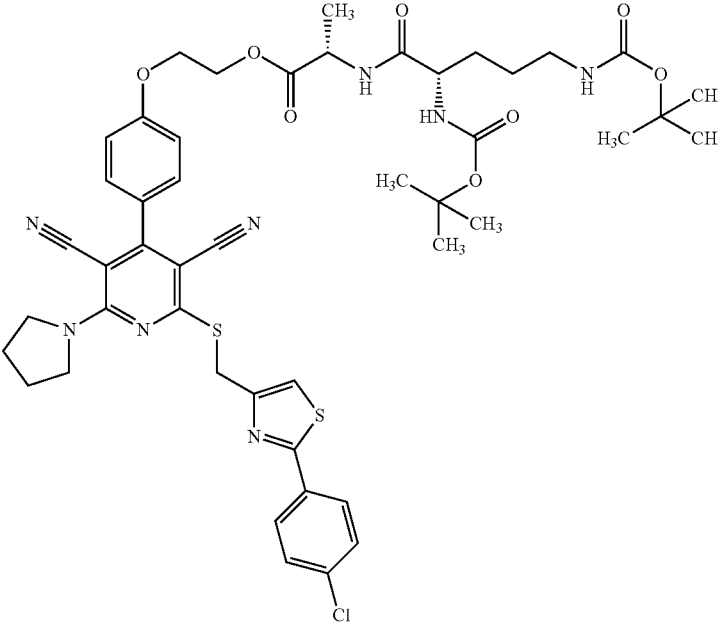 [SMILES: C[C@H](NC(=O)[C@H](CCCNC(=O)OC(C)(C)C)NC(=O)OC(C)(C)C)C(=O)OCCOc1ccc(-c2c(C#N)c(SCc3csc(-c4ccc(Cl)cc4)n3)nc(N3CCCC3)c2C#N)cc1]<br>(68% of theory)<br>*1 | 1.77 min (Method 4); m/z = 859 $(M + H—Boc)^+$ |

*1 purification; before the reaction solution was applied to preparative HPLC, a little water/THF or water/acetonitrile was added to the reaction solution such that a clear solution was obtained.

Example 11A

2-{4-(2-(Azetidin-1-yl)-6-({(2-(4-chlorophenyl)-1,3-thiazol-4-yl)methyl}sulfanyl)-3,5-dicyanopyridin-4-yl)phenoxy}ethyl N-(tert-butoxycarbonyl)-beta-alaninate

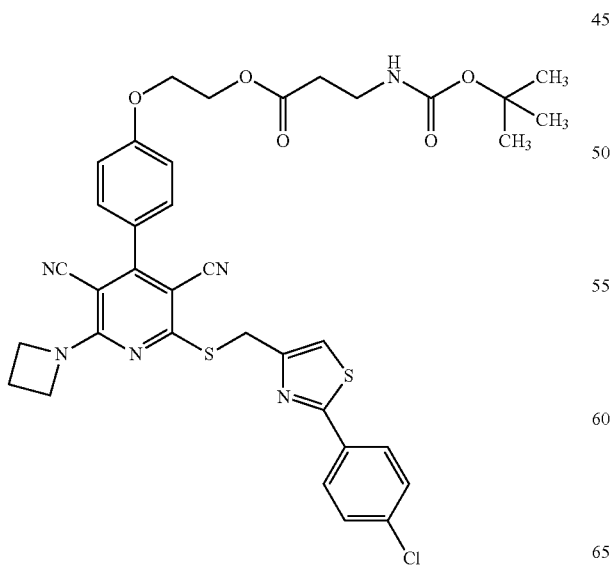

101 mg (0.536 mmol) of N-(tert-butoxycarbonyl)-beta-alanine were initially charged in 2 ml of DMF/dichloromethane (1:1). 44.5 mg (0.232 mmol) of 1-(3-dimethylaminopropyl)-3-ethylcarbodiimide hydrochloride, 10.9 mg (0.89 mmol) of 4-dimethylaminopyridine and 100 mg (0.179 mmol) of 2-(azetidin-1-yl)-6-({(2-(4-chlorophenyl)-1,3-thiazol-4-yl}methyl}sulfanyl)-4-(4-(2-hydroxyethoxy)phenyl)pyridine-3,5-dicarbonitrile (Example 8) were added, and the mixture was then stirred at RT overnight. The crude product was purified by preparative HPLC (acetonitrile/water+0.1% TFA). This gave 118 mg (90% of theory) of the target compound.

LC-MS (Method 5): $R_t$=2.90 min; MS (ESIpos): m/z=731 $(M+H)^+$.

Example 12A

2-{4-(2-(Azetidin-1-yl)-6-({(2-(4-chlorophenyl)-1,3-thiazol-4-yl)methyl}sulfanyl)-3,5-dicyanopyridin-4-yl)phenoxy}ethyl $N^2,N^5$-bis(tert-butoxycarbonyl)-L-ornithinate

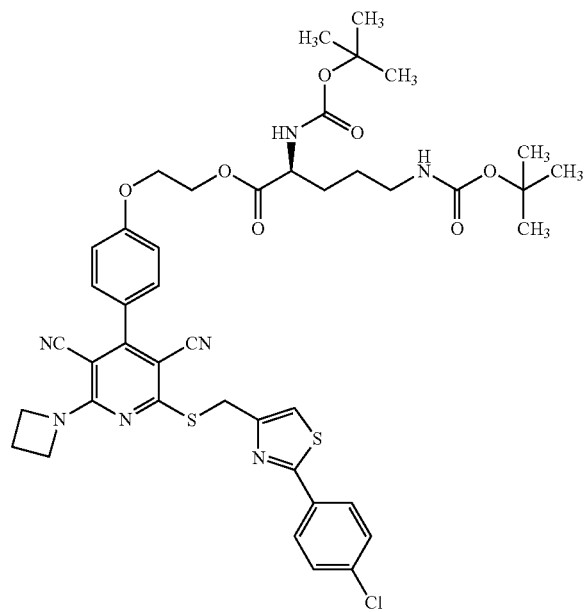 [SMILES: CC(C)(C)OC(=O)NCCC[C@H](NC(=O)OC(C)(C)C)C(=O)OCCOc1ccc(-c2c(C#N)c(SCc3csc(-c4ccc(Cl)cc4)n3)nc(N3CCC3)c2C#N)cc1]

75 mg (0.134 mmol) of 2-(azetidin-1-O-6-({(2-(4-chlorophenyl)-1,3-thiazol-4-ylmethyl}sulfanyl)-4-(4-(2-hydroxyethoxy)phenyl)pyridine-3,5-dicarbonitrile (Example 8), 133.53 mg (0.402 mmol) of $N^2,N^5$-bis(tert-butoxycarbonyl)-L-ornithine and 8.18 mg (0.067 mmol) of 4-dimethylaminopyridine were initially charged in 1 ml of DMF. 1 ml of dichloromethane and 33.37 mg (0.174 mmol) of 1-(3-dimethylaminopropyl)-3-ethylcarbodiimide hydrochloride were added, and the reaction solution was then stirred at 40° C. overnight. After cooling, water/THF was added to the reaction solution in such an amount that a clear solution was formed, and the product was purified by preparative HPLC (acetonitrile/water+0.1% TFA). This gave 104 mg (89% of theory) of the target compound.

LC-MS (Method 6): $R_t$=3.35 min; MS (ESIpos): m/z=874 $(M+H)^+$.

Example 13A

2-{4-(2-(Azetidin-1-yl)-6-({(2-(4-chlorophenyl)-1,3-thiazol-4-ylmethyl}sulfanyl)-3,5-dicyanopyridin-4-yl)phenoxy}ethyl N-(tert-butoxycarbonyl)-L-alaninate

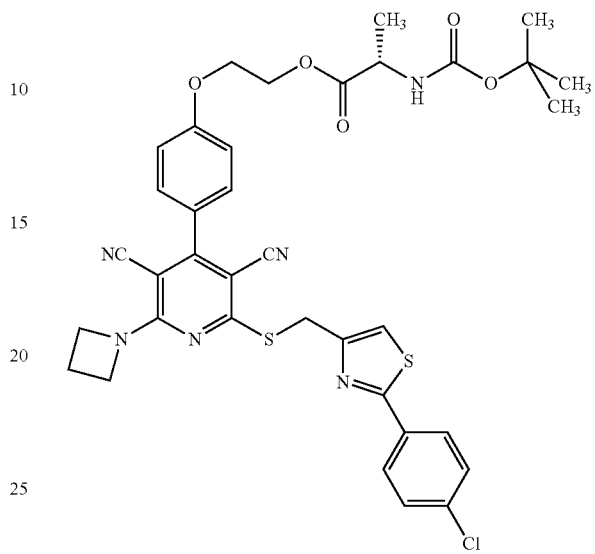

350 mg (0.625 mmol) of 2-(azetidin-1-yl)-6-({(2-(4-chlorophenyl)-1,3-thiazol-4-ylmethyl}sulfanyl)-4-(4-(2-hydroxyethoxy)phenyl)pyridine-3,5-dicarbonitrile (Example 8), 354.7 mg (1.875 mmol) of N-(tert-butoxycarbonyl)-L-alanine and 38.17 mg (0.312 mmol) of 4-dimethylaminopyridine were initially charged in 3.3 ml of DMF. 3.3 ml of THF and 155.7 mg (0.812 mmol) of 1-(3-dimethylaminopropyl)-3-ethylcarbodiimide hydrochloride were added, and the reaction solution was then stirred at 40° C. overnight. After cooling, the reaction solution was purified by preparative HPLC (acetonitrile/water+0.1% TFA). This gave 377 mg (83% of theory) of the target compound.

LC-MS (Method 6): $R_t$=3.26 min; MS (ESIpos): m/z=731 $(M+H)^+$.

Example 14A

2-{4-(2-({(2-(4-Chlorophenyl)-1,3-thiazol-4-ylmethyl}sulfanyl)-3,5-dicyano-6-(propylamino)pyridin-4-yl)phenoxy}ethyl N-(tert-butoxycarbonyl)-L-alaninate

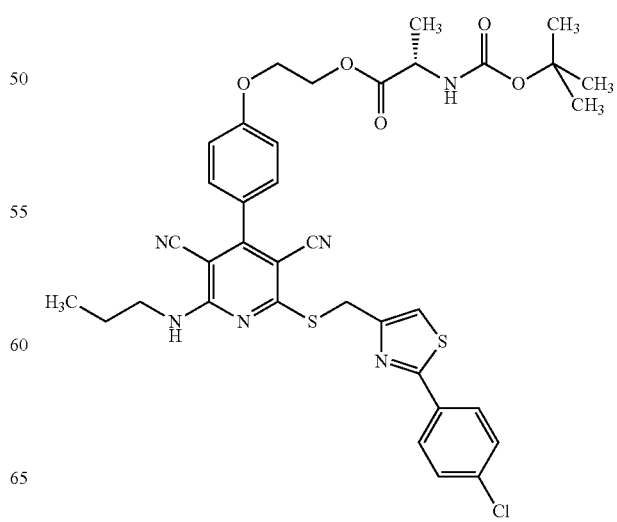

758 mg (1.348 mmol) of 2-({(2-(4-chlorophenyl)-1,3-thiazol-4-ylmethyl}sulfanyl)-4-(4-(2-hydroxyethoxy)phenyl)-6-(propylamino)pyridine-3,5-dicarbonitrile (Example 12), 765 mg (4.043 mmol) of N-(tert-butoxycarbonyl)-L-alanine and 82 mg (0.674 mmol) of 4-dimethylaminopyridine were initially charged in 10.3 ml of DMF/dichloromethane (1:1). 336 mg (1.752 mmol) of 1-(3-dimethylaminopropyl)-3-ethylcarbodiimide hydrochloride were added, and the reaction solution was then stirred at RT overnight. The reaction solution was freed from dichloromethane and the residue was purified by preparative HPLC (acetonitrile/water+0.1% TFA). This gave 929 mg (94% of theory) of the target compound.

LC-MS (Method 2): $R_t$=1.54 min; MS (ESIneg): m/z=731 (M−H)$^-$.

The examples listed in Table 2 were prepared analogously to Example 14A from the appropriate starting materials.

TABLE 2

| Example No. | Structure | LC-MS: $R_t$ (min) (Method); MS (ESI): m/z (M + H)$^+$ |
|---|---|---|
| 15A | 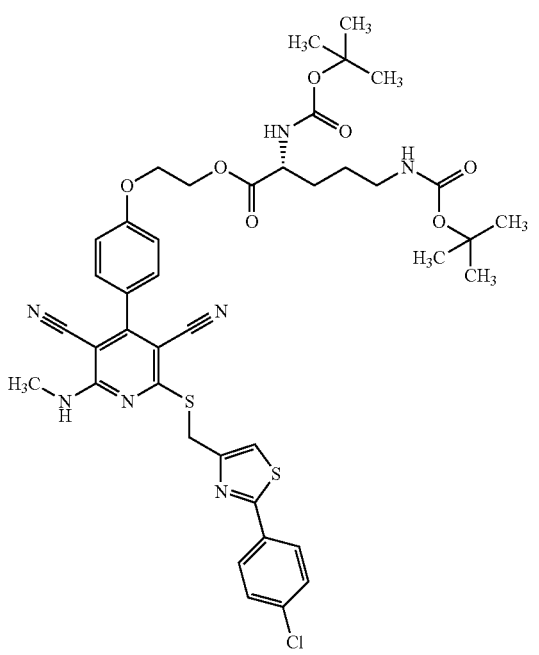 [SMILES: CNc1nc(SCc2csc(-c3ccc(Cl)cc3)n2)c(C#N)c(-c2ccc(OCCOC(=O)[C@@H](CCCNC(=O)OC(C)(C)C)NC(=O)OC(C)(C)C)cc2)c1C#N]<br>(68% of theory) | 1.51 min (Method 2); m/z = 848 |

TABLE 2-continued
| Example No. | Structure | LC-MS: R_t (min) (Method); MS (ESI): m/z (M + H)+ |
|---|---|---|
| 16A | 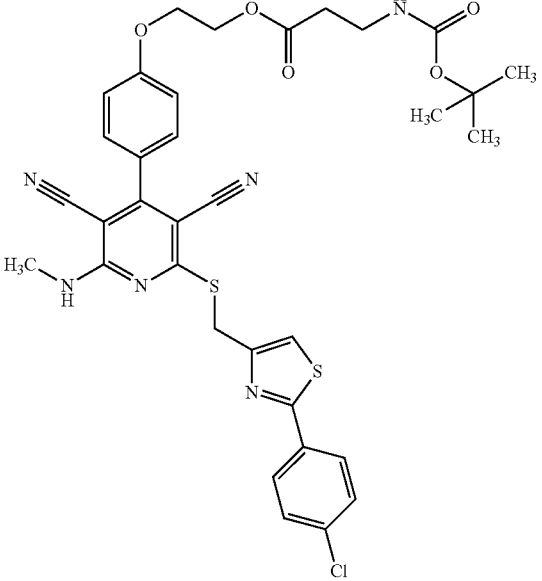 (88% of theory) | 1.66 min (Method 4); m/z = 605 (M + H—BOC)+ |
| 17A | 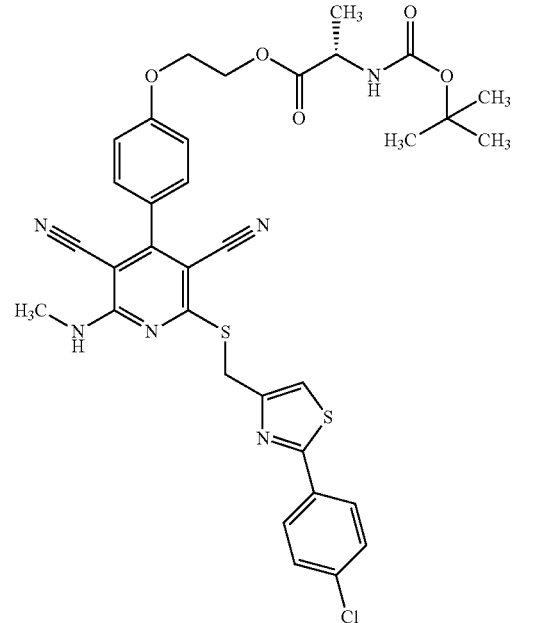 [SMILES: CNc1nc(SCc2csc(-c3ccc(Cl)cc3)n2)c(C#N)c(-c2ccc(OCCOC(=O)[C@H](C)NC(=O)OC(C)(C)C)cc2)c1C#N] (66% of theory) *2 | 1.47 min (Method 2); m/z = 705 |

TABLE 2-continued
| Example No. | Structure | LC-MS: R$_t$ (min) (Method); MS (ESI): m/z (M + H)$^+$ |
|---|---|---|
| 18A | 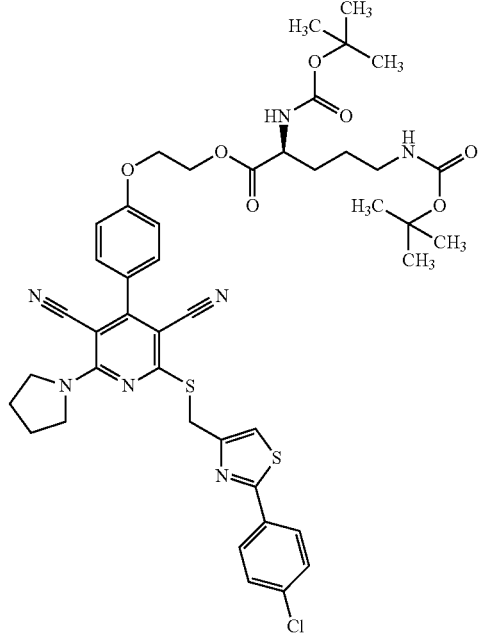 [SMILES: CC(C)(C)OC(=O)NCCC[C@H](NC(=O)OC(C)(C)C)C(=O)OCCOc1ccc(-c2c(C#N)c(SCc3csc(-c4ccc(Cl)cc4)n3)nc(N3CCCC3)c2C#N)cc1]<br>(94% of theory) | 3.38 min (Method 6); m/z = 888 |
| 19A | 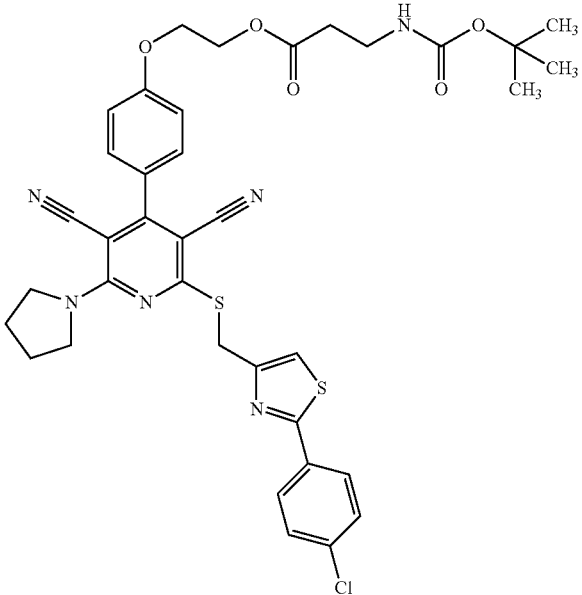 [SMILES: CC(C)(C)OC(=O)NCCC(=O)OCCOc1ccc(-c2c(C#N)c(SCc3csc(-c4ccc(Cl)cc4)n3)nc(N3CCCC3)c2C#N)cc1]<br>(95% of theory) | 1.51 min (Method 2); m/z = 745 |

TABLE 2-continued

| Example No. | Structure | LC-MS: $R_t$ (min) (Method); MS (ESI): m/z $(M + H)^+$ |
|---|---|---|
| 20A | 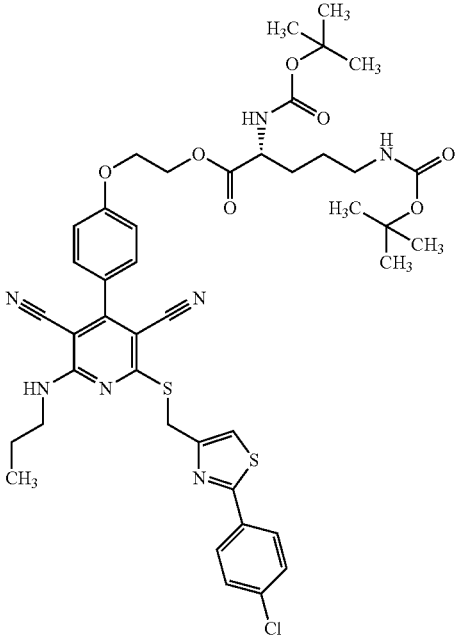 [SMILES: CCCNc1nc(SCc2csc(-c3ccc(Cl)cc3)n2)c(C#N)c(-c2ccc(OCCOC(=O)[C@@H](CCCNC(=O)OC(C)(C)C)NC(=O)OC(C)(C)C)cc2)c1C#N]<br>(39% of theory) | 1.57 min (Method 2); m/z = 876 |

*2 different purification; the crude product was purified by preparative HPLC (acetonitrile/water + 0.1% TFA). The product was then purified by column chromatography on silicia gel 60 (mobile phase: toluene/acetonitrile 10:1).

Example 21A

2-{4-(2-({(2-(4-Chlorophenyl)-1,3-thiazol-4-yl)methyl}sulfanyl)-3,5-dicyano-6-(propylamino)pyridin-4-yl)phenoxy}ethyl $N^2,N^6$-bis(tert-butoxycarbonyl)-L-lysyl-L-alaninate 445 mg (1.284 mmol) of $N^2,N^6$-bis(tert-butoxycarbonyl)-L-lysine were initially charged in 12.3 ml of DMF. 268 mg (1.400 mmol) of 1-hydroxy-1H-benzotriazole hydrate, 237 mg (1.750 mmol) of 1-(3-dimethylaminopropyl)-3-ethylcarbodiimide hydrochloride and 0.51 ml (2.917 mmol) of N,N-diisopropylethylamine were added, and 872 mg (1.167

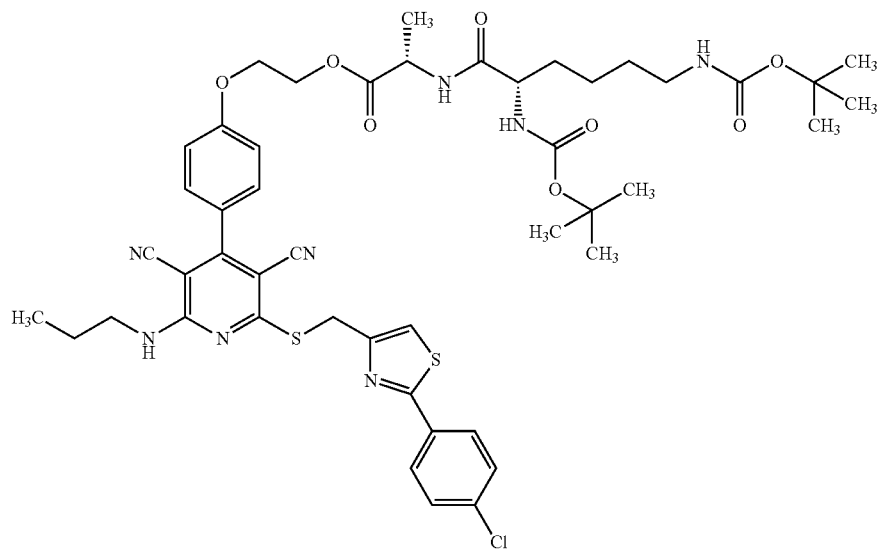 [SMILES: CCCNc1nc(SCc2csc(-c3ccc(Cl)cc3)n2)c(C#N)c(-c2ccc(OCCOC(=O)[C@H](C)NC(=O)[C@H](CCCCNC(=O)OC(C)(C)C)NC(=O)OC(C)(C)C)cc2)c1C#N]

mmol) of 2-{4-(2-({(2-(4-chlorophenyl)-1,3-thiazol-4-yl)methyl}sulfanyl)-3,5-dicyano-6-(propylamino)pyridin-4-yl)phenoxy}ethyl L-alaninate trifluoroacetate (Example 38) were then added and the mixture was stirred at RT overnight. Water was added, and the reaction solution was extracted three times with ethyl acetate. The combined organic phases were dried over sodium sulfate, filtered and concentrated by evaporation. The residue was purified by preparative HPLC (acetonitrile/water+0.1% TFA). For further purification, the product obtained was subjected to column chromatography on silica gel 60 (mobile phase: cyclohexane/ethyl acetate 1/1). This gave 698 mg (62% of theory) of the target compound.

LC-MS (Method 2): $R_t$=1.55 min; MS (ESIpos): m/z=961 $(M+H)^+$.

The examples listed in Table 3 were prepared analogously to Example 21A from the appropriate starting materials.

TABLE 3

| Example No. | Structure | LC-MS: $R_t$ (min) (Method); MS (ESI): m/z $(M + H)^+$ |
|---|---|---|
| 22A | 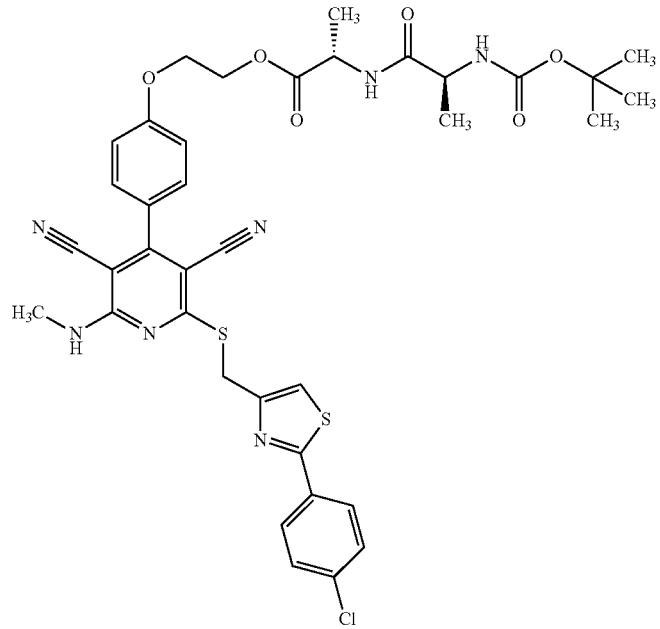 [SMILES: CNc1nc(SCc2csc(-c3ccc(Cl)cc3)n2)c(C#N)c(-c2ccc(OCCOC(=O)[C@H](C)NC(=O)[C@H](C)NC(=O)OC(C)(C)C)cc2)c1C#N]<br>(79% of theory)<br>*3 | 1.60 min (Method 4); m/z = 776 |

TABLE 3-continued

| Example No. | Structure | LC-MS: $R_t$ (min) (Method); MS (ESI): m/z $(M + H)^+$ |
|---|---|---|
| 23A | (structure) (81% of theory) *4 | 1.65 min (Method 4); m/z = 933 |
| 24A | (structure) (58% of theory) *5 | 1.54 min (Method 2); m/z = 973 |

*3 different work-up; the reaction solution was purified by preparative HPLC (acetonitrile/water + 0.1% TFA).

*4 different work-up; the reaction solution was concentrated by evaporation. The crude product was purified by column chromatography on silica gel 60 (mobile phase: dichloromethane/methanol 20:1). The product was purified further by preparative HPLC (acetonitrile/water + 0.1% TFA).

*5 different work-up; water/acetonitrile was added and the reaction solution was extracted three times with dichloromethane. The combined organic phases were washed once with water, dried over sodium sulfate, filtered and concentrated by evaporation. The residue was purified by column chromatography (column: Waters Sunfire C 18, 5 μm, 250 × 30 mm, mobile phase: water/methanol/THF = 15/70/15).

Example 25A

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl N-(tert-butoxycarbonyl)-L-alaninate

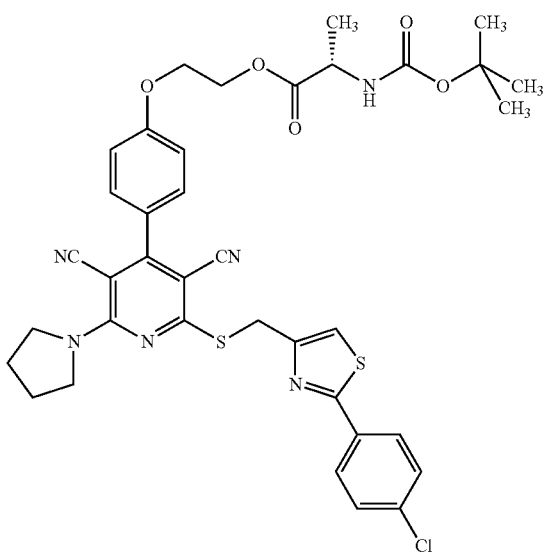 [SMILES: C[C@H](NC(=O)OC(C)(C)C)C(=O)OCCOc1ccc(-c2c(C#N)c(SCc3csc(-c4ccc(Cl)cc4)n3)nc(N3CCCC3)c2C#N)cc1]

218 mg (1.15 mmol) of N-(tert-butoxycarbonyl)-L-alanine were initially charged in 5 ml of DMF. 240 mg (1.254 mmol) of 1-(3-dimethylaminopropyl)-3-ethylcarbodiimide hydrochloride, 240 mg (1.568 mmol) of 1-hydroxy-1H-benzotriazole hydrate and 0.455 ml (2.613 mmol) of N,N-diisopropylethylamine were added, 300 mg (0.523 mmol) of 2-({(2-(4-chlorophenyl)-1,3-thiazol-4-ylmethyl}sulfanyl)-4-(4-(2-hydroxyethoxy)phenyl)-6-(pyrrolidin-1-yl)pyridine-3,5-dicarbonitrile (Example 1) were then added and the mixture was stirred at RT overnight. The reaction mixture was purified by preparative HPLC (acetonitrile/water+0.1% TFA). This gave 382 mg (98% of theory) of the target compound.

LC-MS (Method 2): $R_t$=1.52 min; MS (ESIpos): m/z=745 $(M+H)^+$.

$^1$H-NMR (400 MHz, DMSO-$d_6$): δ=7.95 (d, 2H), 7.70 (s, 1H), 7.58 (d, 2H), 7.48 (d, 2H), 7.31 (d, 1H), 7.11 (d, 2H), 4.70 (s, 2H), 4.48-4.33 (m, 2H), 4.30-4.23 (m, 2H), 4.07-3.99 (m, 1H), 3.89-3.78 (m, 4H), 1.98-1.87 (m, 4H), 1.35 (s, 9H) 1.24 (d, 3H).

Example 26A

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl $N^2,N^6$-bis(tert-butoxycarbonyl)-L-lysyl-L-alaninate

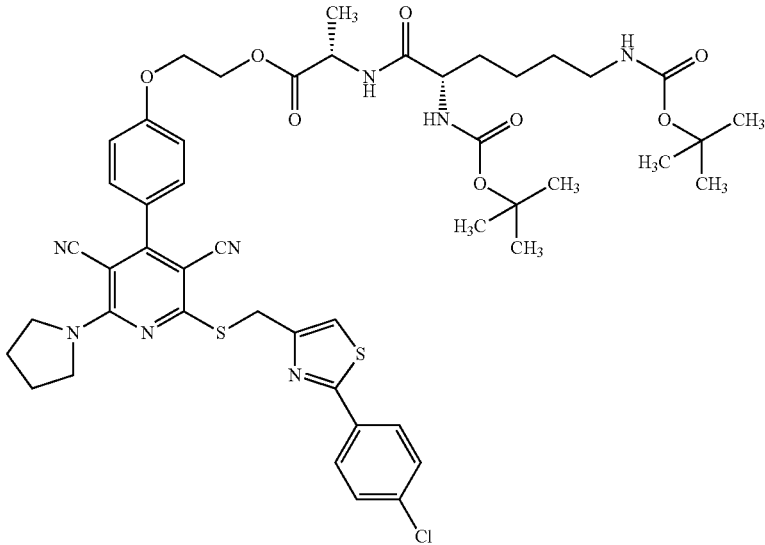 [SMILES: C[C@H](NC(=O)[C@H](CCCCNC(=O)OC(C)(C)C)NC(=O)OC(C)(C)C)C(=O)OCCOc1ccc(-c2c(C#N)c(SCc3csc(-c4ccc(Cl)cc4)n3)nc(N3CCCC3)c2C#N)cc1]

166 mg (0.478 mmol) of $N^2,N^6$-bis(tert-butoxycarbonyl)-L-lysine were initially charged in 6.4 ml of DMF. 88 mg (0.652 mmol) of 1-hydroxy-1H-benzotriazole hydrate, 100 mg (0.522 mmol) of 1-(3-dimethylaminopropyl)-3-ethylcarbodiimide hydrochloride and 0.379 ml (2.173 mmol) of N,N-diisopropylethylamine were added, 330 mg (0.435 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-alaninate trifluoroacetate (Example 40) were then added and the mixture was stirred at RT overnight.

Water/acetonitrile was added to the reaction solution in such an amount that a clear solution was formed. This was purified by preparative HPLC (acetonitrile/water+0.1% TFA). This gave 216 mg (44% of theory) of the target compound.

LC-MS (Method 4): R$_t$=1.79 min; MS (ESIpos): m/z=973 (M+H)$^+$.

Example 27A

2-{4-(2-({2-(4-Chlorophenyl)-1,3-thiazol-4-yl)methyl}sulfanyl)-3,5-dicyano-6-(pyrrolidin-1-yl)pyridin-4-yl)phenoxy}ethyl 1-(tert-butoxycarbonyl)-L-prolyl-L-alaninate

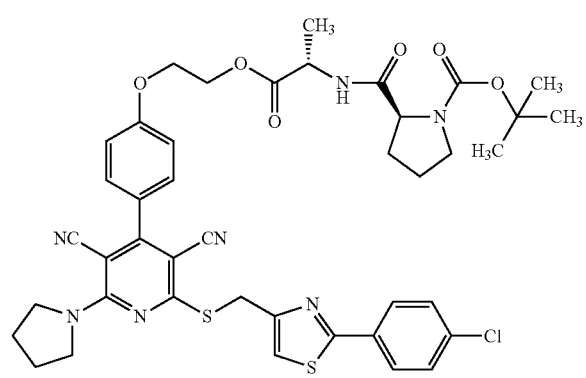 [SMILES: C[C@H](NC(=O)[C@@H]1CCCN1C(=O)OC(C)(C)C)C(=O)OCCOc1ccc(-c2c(C#N)c(SCc3csc(-c4ccc(Cl)cc4)n3)nc(N3CCCC3)c2C#N)cc1]

202 mg (0.942 mmol) of 1-(tert-butoxycarbonyl)-L-proline together with 246 mg (1.284 mmol) of 1-(3-dimethylaminopropyl)-3-ethylcarbodiimide hydrochloride, 157 mg (1.027 mmol) of 1-hydroxy-1H-benzotriazole hydrate and 0.746 ml (4.281 mmol) of N,N-diisopropylethylamine were dissolved in 7.5 ml of DMF, after which 650 mg (0.856 mmol) of 2-{4-(2-({2-(4-chlorophenyl)-1,3-thiazol-4-yl)methyl}sulfanyl)-3,5-dicyano-6-(pyrrolidin-1-yl)pyridin-4-yl)phenoxy}ethyl L-alaninate trifluoroacetate were added. After stirring at room temperature overnight, the reaction mixture was purified by preparative HPLC (acetonitrile/water). This gave 495 mg (69% of theory) of the target compound.

LC-MS (Method 6): R$_t$=3.29 min; MS (ESIpos): m/z=842 (M+H)$^+$.

Example 28A

2-{4-(2-({2-(4-Chlorophenyl)-1,3-thiazol-4-yl)methyl}sulfanyl)-3,5-dicyano-6-(pyrrolidin-1-yl)pyridin-4-yl)phenoxy}ethyl N-(tert-butoxycarbonyl)-L-isoleucyl-L-alaninate

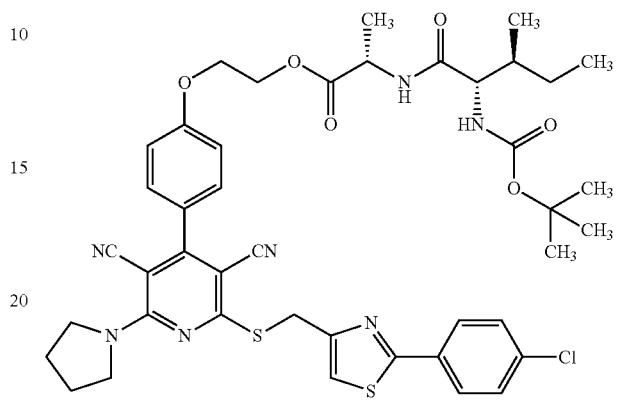

217 mg (0.942 mmol) of N-(tert-butoxycarbonyl)-L-isoleucine together with 246 mg (1.284 mmol) of 1-(3-dimethylaminopropyl)-3-ethylcarbodiimide hydrochloride, 157 mg (1.027 mmol) of 1-hydroxy-1H-benzotriazole hydrate and 0.746 ml (4.281 mmol) of N,N-diisopropylethylamine were dissolved in 7.5 ml of DMF, after which 650 mg (0.856 mmol) of 2-{4-(2-({2-(4-chlorophenyl)-1,3-thiazol-4-ylmethyl}sulfanyl)-3,5-dicyano-6-(pyrrolidin-1-yl)pyridin-4-yl)phenoxy}ethyl L-alaninate trifluoroacetate were added. After stirring at room temperature overnight, the reaction mixture was purified by preparative HPLC (acetonitrile/water). This gave 414 mg (56% of theory) of the target compound.

LC-MS (Method 2): R$_t$=1.54 min; MS (ESIpos): m/z=858 (M+H)$^+$.

$^1$H-NMR (400 MHz, DMSO-d$_6$): δ=8.31 (d, 1H), 7.95 (d, 2H), 7.70 (s, 1H), 7.58 (d, 2H), 7.48 (d, 2H), 7.11 (d, 2H), 6.61 (d, 1H), 4.70 (s, 2H), 4.46-4.23 (m, 5H), 3.89-3.78 (m, 5H), 1.99-1.89 (m, 4H), 1.71-1.59 (m, 1H), 1.46-1.39 (m, 1H) 1.36 (s, 9H), 1.29 (d, 3H), 1.13-1.00 (m, 1H), 0.83-0.76 (m, 6H).

Example 29A

2-{4-(2-({2-(4-Chlorophenyl)-1,3-thiazol-4-ylmethyl}sulfanyl)-3,5-dicyano-6-(pyrrolidin-1-yl)pyridin-4-yl)phenoxy}ethyl N-{(2S)-2,4-bis((tert-butoxycarbonyl)amino)butanoyl}-L-alaninate

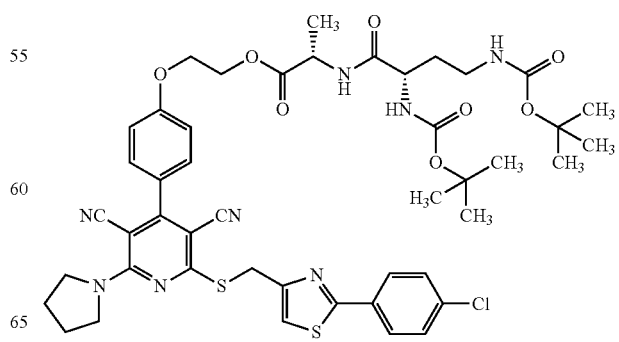

361 mg (0.724 mmol) of (2S)-2,4-bis((tert-butoxycarbonyl)amino)butanoic acid N,N-dicyclohexylamine salt together with 151 mg (0.790 mmol) of 1-(3-dimethylaminopropyl)-3-ethylcarbodiimide hydrochloride, 151 mg (0.988 mmol) of 1-hydroxy-1H-benzotriazole hydrate and 0.574 ml (3.293 mmol) of N,N-diisopropylethylamine were dissolved in 10 ml of DMF, after which 500 mg (0.659 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-alaninate trifluoroacetate were added. The reaction mixture was stirred at room temperature overnight and then purified twice by preparative HPLC (acetonitrile/water). This gave 420 mg (67% of theory) of the target compound.

LC-MS (Method 1): $R_t$=3.19 min; MS (ESIpos): m/z=945 (M+H)$^+$.

Example 30A

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl N-(tert-butoxycarbonyl)-3-((tert-butoxycarbonyl)amino)-L-alanyl-L-alaninate

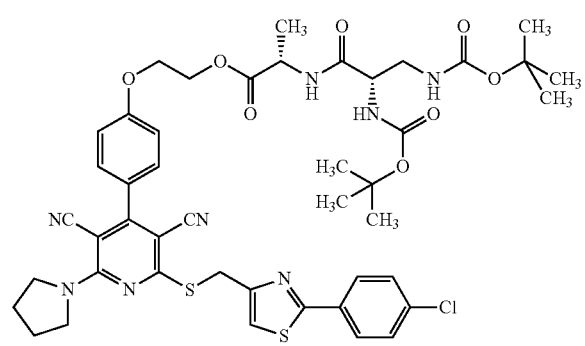 [SMILES: C[C@H](NC(=O)[C@H](CNC(=O)OC(C)(C)C)NC(=O)OC(C)(C)C)C(=O)OCCOc1ccc(-c2c(C#N)c(SCc3csc(-c4ccc(Cl)cc4)n3)nc(N3CCCC3)c2C#N)cc1]

351 mg (0.724 mmol) of N-(tert-butoxycarbonyl)-3-((tert-butoxycarbonyl)amino)-L-alanine N,N-dicyclohexylamine salt together with 151 mg (0.790 mmol) of 1-(3-dimethylaminopropyl)-3-ethylcarbodiimide hydrochloride, 151 mg (0.988 mmol) of 1-hydroxy-1H-benzotriazole hydrate and 0.574 ml (3.293 mmol) of N,N-diisopropylethylamine were dissolved in 10 ml of DMF, after which 500 mg (0.659 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-alaninate trifluoroacetate were added. The reaction mixture was stirred at room temperature overnight and then purified twice by preparative HPLC (acetonitrile/water). This gave 290 mg (47% of theory) of the target compound.

LC-MS (Method 1): $R_t$=3.18 min; MS (ESIpos): m/z=931 (M+H)$^+$.

Example 31A

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl N-(tert-butoxycarbonyl)-L-histidyl-L-alaninate

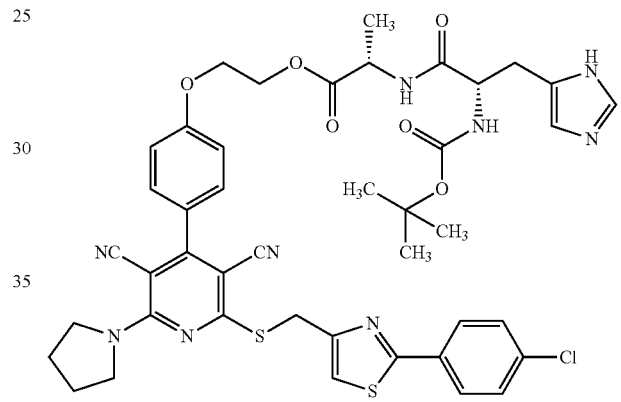

257 mg (0.724 mmol) of N-(tert-butoxycarbonyl)-L-histidyl-L-alanine together with 151 mg (0.790 mmol) of 1-(3-dimethylaminopropyl)-3-ethylcarbodiimide hydrochloride, 151 mg (0.988 mmol) of 1-hydroxy-1H-benzotriazole hydrate and 0.574 ml (3.293 mmol) of N,N-diisopropylethylamine were dissolved in 10 ml of DMF, after which 500 mg (0.659 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl L-alaninate trifluoroacetate were added. The reaction mixture was stirred at room temperature overnight and then purified twice by preparative HPLC (acetonitrile/water). This gave 169 mg (28% of theory) of the target compound.

LC-MS (Method 4): $R_t$=1.42 min; MS (ESIpos): m/z=882 (M+H)$^+$.

Example 32A

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl $N^5$—(N,N'-bis(tert-butoxycarbonyl)carbamimidoyl)-$N^2$-(tert-butoxycarbonyl)-L-ornithyl-L-alaninate

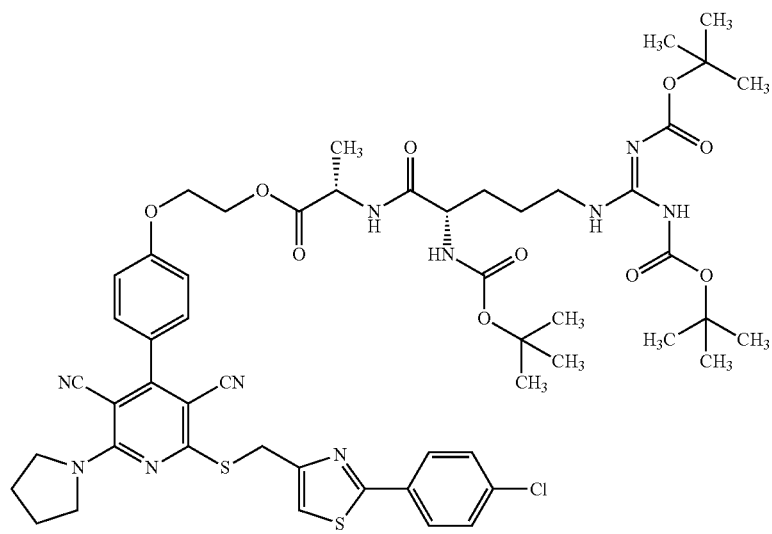 [SMILES: C[C@H](NC(=O)[C@H](CCCN/C(=N/C(=O)OC(C)(C)C)NC(=O)OC(C)(C)C)NC(=O)OC(C)(C)C)C(=O)OCCOc1ccc(-c2c(C#N)c(SCc3csc(-c4ccc(Cl)cc4)n3)nc(N3CCCC3)c2C#N)cc1]

344 mg (0.724 mmol) of $N^5$—(N,N'-bis(tert-butoxycarbonyl)carbamimidoyl)-$N^2$-(tert-butoxycarbonyl)-L-ornithine together with 151 mg (0.790 mmol) of 1-(3-dimethylaminopropyl)-3-ethylcarbodiimide hydrochloride, 151 mg (0.988 mmol) of 1-hydroxy-1H-benzotriazole hydrate and 0.574 ml (3.293 mmol) of N,N-diisopropylethylamine were dissolved in 10 ml of DMF, after which 500 mg (0.659 mmol) of 2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl L-alaninate trifluoroacetate were added. The reaction mixture was stirred at room temperature overnight and then purified twice by preparative HPLC (acetonitrile/water). This gave 341 mg (47% of theory) of the target compound.

LC-MS (Method 4): $R_t$=1.88 min; MS (ESIpos): m/z=1101 (M+H)$^+$.

Example 33A

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl N-(tert-butoxycarbonyl)-L-leucinate

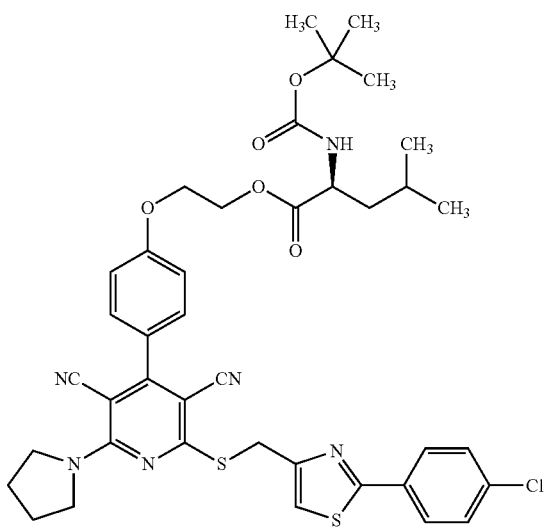 [SMILES: CC(C)C[C@H](NC(=O)OC(C)(C)C)C(=O)OCCOc1ccc(-c2c(C#N)c(SCc3csc(-c4ccc(Cl)cc4)n3)nc(N3CCCC3)c2C#N)cc1]

0.89 g (3.82 mmol) of N-(tert-butoxycarbonyl)-L-leucine were initially charged in 10 ml of DMF, and 0.81 g (4.18 mmol) of 1-(3-dimethylaminopropyl)-3-ethylcarbodiimide hydrochloride, 0.80 g (5.23 mmol) of 1-hydroxy-1H-benzotriazole hydrate and 1.13 g (8.71 mmol) of N,N-diisopropylethylamine were added. The mixture was stirred until a clear solution had been obtained. 1.00 g (1.74 mmol) of 2-({(2-(4-chlorophenyl)-1,3-thiazol-4-yl)methyl}sulfanyl)-4-(4-(2-hydroxyethoxy)phenyl)-6-(pyrrolidin-1-yl)pyridine-3,5-dicarbonitrile was then added, and the mixture was stirred at room temperature for 18 h. The mixture was added to 300 ml of water. The residue formed was filtered off with suction and washed with 50 ml of water. The crude product was dissolved in 50 ml of dichloromethane. The aqueous phase was separated off and the organic phase was dried over sodium sulfate. Removal of the solvent under reduced pressure gave 1.37 g (100% of theory) of the desired target compound.

LC/MS (Method 2): $R_t$=1.64 min; MS (ESIpos): m/z=787 (M+H)$^+$.

Example 34A

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl L-leucinate trifluoroacetate

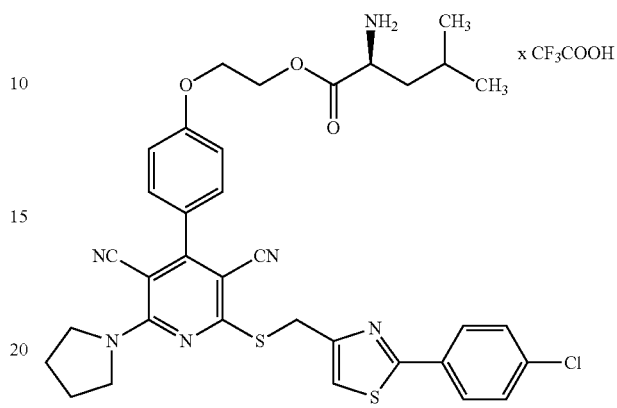

1.37 g (1.74 mmol) of 2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl N-(tert-butoxycarbonyl)-L-leucinate were initially charged in 15 ml of dichloromethane, and 15.00 ml (194.70 mmol) of trifluoroacetic acid were added. The mixture was stirred at room temperature for 1 h. After removal of the solvent under reduced pressure, the residue was dissolved in 5.00 ml of dichloromethane and 10.00 ml of diethyl ether were added. The residue formed was filtered off with suction. Drying gave 1.09 g (76.1% of theory) of the desired target compound.

LC/MS (Method 2): $R_t$=1.16 min; MS (ESIpos): m/z=687 (M-TFA+H)$^+$.

Example 35A

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl N-(tert-butoxycarbonyl)-L-alanyl-L-leucinate

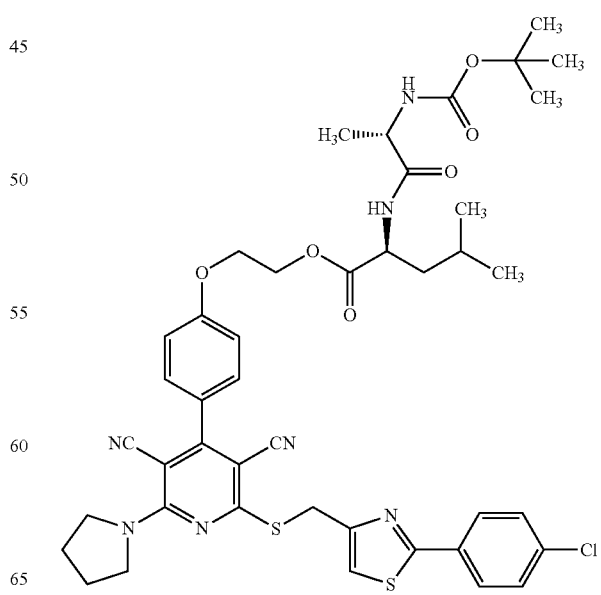

86 mg (0.45 mmol) of N-(tert-butoxycarbonyl)-L-alanine were initially charged in 5.0 ml of DMF, and 95 mg (0.49 mmol) of 1-(3-dimethylaminopropyl)-3-ethylcarbodiimide hydrochloride, 95 mg (0.62 mmol) of 1-hydroxy-1H-benzotriazole hydrate and 266.13 g (2.06 mmol) of N,N-diisopropylethylamine were added. The mixture was stirred until a clear solution had been obtained. 330 mg (0.41 mmol) of 2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl L-leucinate trifluoroacetate were then added, and the mixture was stirred at room temperature for 18 h. The reaction mixture was added to 300 ml of water. The residue formed was filtered off with suction and washed with 20 ml of water. The crude product was suspended in 15 ml of methanol and sonicated in an ultrasonic bath for 5 min. The residue was filtered off with suction and washed with 10 ml of diethyl ether. This gave 0.15 g (43% of theory) of the desired target compound.

LC/MS (Method 2): $R_t$=1.58 min; MS (ESIpos): m/z=858 (M+H)$^+$.

Example 36A

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl N-(tert-butoxycarbonyl)-beta-alanyl-L-leucinate

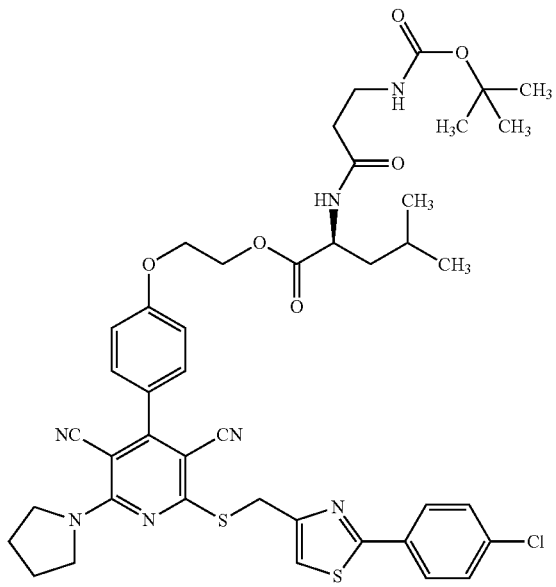 [SMILES: CC(C)C[C@H](NC(=O)CCNC(=O)OC(C)(C)C)C(=O)OCCOc1ccc(-c2c(C#N)c(SCc3csc(-c4ccc(Cl)cc4)n3)nc(N3CCCC3)c2C#N)cc1]

86 mg (0.45 mmol) of N-(tert-butoxycarbonyl)-beta-alanine were initially charged in 5.0 ml of DMF, and 95 mg (0.49 mmol) of 1-(3-dimethylaminopropyl)-3-ethylcarbodiimide hydrochloride, 95 mg (0.62 mmol) of 1-hydroxy-1H-benzotriazole hydrate and 266.13 g (2.06 mmol) of N,N-diisopropylethylamine were added. The mixture was stirred until a clear solution had been obtained. 330 mg (0.41 mmol) of 2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl L-leucinate trifluoroacetate were then added, and the mixture was stirred at room temperature for 18 h. The reaction mixture was added to 300 ml of water. The residue formed was filtered off with suction and washed with 20 ml of water. The crude product was suspended in 15 ml of methanol and sonicated in an ultrasonic bath for 5 min. The residue was filtered off with suction and washed with 10 ml of diethyl ether. This gave 0.13 g (37% of theory) of the desired target compound.

LC/MS (Method 2): $R_t$=1.56 min; MS (ESIpos): m/z=858 (M+H)$^+$.

Example 37A

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl N-(tert-butoxycarbonyl)glycyl-L-leucinate

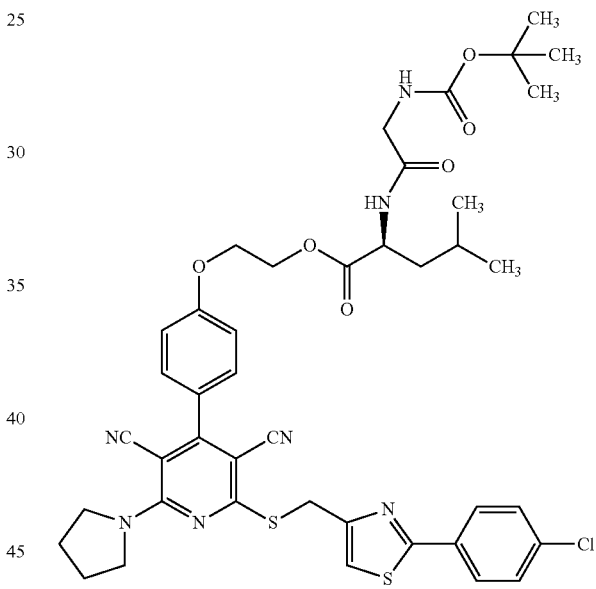

80 mg (0.45 mmol) of N-(tert-butoxycarbonyl)glycine were initially charged in 5.0 ml of DMF, and 95 mg (0.49 mmol) of 1-(3-dimethylaminopropyl)-3-ethylcarbodiimide hydrochloride, 95 mg (0.62 mmol) of 1-hydroxy-1H-benzotriazole hydrate and 267 mg (2.06 mmol) of N,N-diisopropylethylamine were added. The mixture was stirred until a clear solution had been obtained. 330 mg (0.41 mmol) of 2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl L-leucinate trifluoroacetate were then added, and the mixture was stirred at room temperature for 18 h. The reaction mixture was added to 300 ml of water. The residue formed was filtered off with suction and washed with 20 ml of water. The crude product was suspended in 15 ml of methanol and sonicated in an ultrasonic bath for 5 min. The residue was filtered off with suction and washed with 10 ml of diethyl ether. This gave 0.17 g (47% of theory) of the desired target compound.

LC/MS (Method 2): $R_t$=1.56 min; MS (ESIpos): m/z=844 (M+H)$^+$.

EXEMPLARY EMBODIMENTS

Example 1

2-({(2-(4-Chlorophenyl)-1,3-thiazol-4-ylmethyl}sulfanyl)-4-(4-(2-hydroxyethoxy)phenyl)-6-(pyrrolidin-1-yl)pyridine-3,5-dicarbonitrile

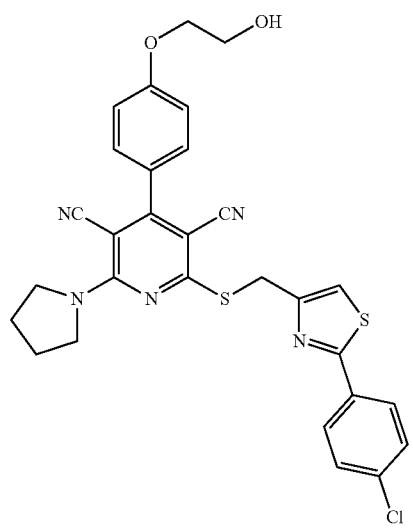 [SMILES: N#Cc1c(SCc2csc(-c3ccc(Cl)cc3)n2)nc(N2CCCC2)c(C#N)c1-c1ccc(OCCO)cc1]

At RT, 90 mg (0.17 mmol) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A) and 30 µl (0.37 mmol) of pyrrolidine were stirred in 2.3 ml of THF for 30 min. About 12 ml of water were added to the reaction mixture, the suspension formed was freed from THF on a rotary evaporator, and the precipitate formed was filtered off and washed with water and dried under high vacuum. This gave 78 mg (81% of theory) of the desired target compound.

$^1$H-NMR (400 MHz, DMSO-d$_6$): δ=7.95 (d, 2H), 7.70 (s, 1H), 7.58 (d, 2H), 7.47 (d, 2H), 7.10 (d, 2H), 4.90 (t, 1H), 4.70 (s, 2H), 4.07 (t, 2H), 3.83 (br s, 4H), 3.74 (q, 2H), 1.94 (br s, 4H).

LC-MS (Method 5): R$_t$=2.63 min; MS (ESIpos): m/z=574 (M+H)$^+$.

Example 2

2-({(2-(4-Chlorophenyl)-1,3-thiazol-4-yl)methyl}sulfanyl)-4-(4-(2-hydroxyethoxy)phenyl)-6-(methylamino)pyridine-3,5-dicarbonitrile

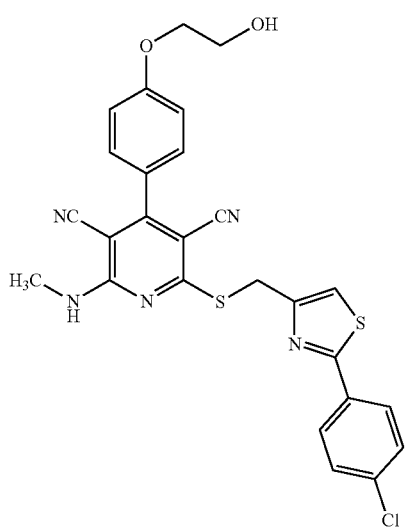 [SMILES: CNc1nc(SCc2csc(-c3ccc(Cl)cc3)n2)c(C#N)c(-c2ccc(OCCO)cc2)c1C#N]

At RT, 3.0 g (5.56 mmol) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A) and 11.12 ml (22.24 mmol) of methylamine were stirred in 75 ml of THF overnight. About 300 ml of water were added to the reaction mixture, and the precipitate formed was filtered off and washed with water and dried under high vacuum. This gave 2.69 g (91% of theory) of the desired target compound.

$^1$H-NMR (400 MHz, DMSO-d$_6$): δ=8.12 (q, 1H), 7.96 (d, 2H), 7.69 (s, 1H), 7.59 (d, 2H), 7.48 (d, 2H), 7.11 (d, 2H), 4.91 (t, 1H), 4.72 (s, 2H), 4.09 (t, 2H), 3.74 (q, 2H), 3.01 (d, 3H).

LC-MS (Method 5): R$_t$=2.41 min; MS (ESIpos): m/z=534 (M+H)$^+$.

Example 3

2-({(2-(4-Chlorophenyl)-1,3-thiazol-4-yl)methyl}sulfanyl)-6-(ethylamino)-4-(4-(2-hydroxyethoxy)phenyl)pyridine-3,5-dicarbonitrile

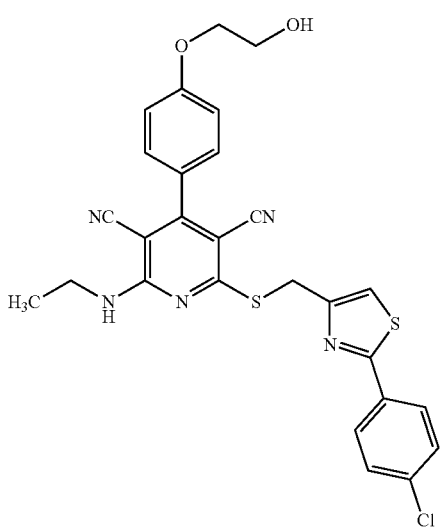 [SMILES: CCNc1nc(SCc2csc(-c3ccc(Cl)cc3)n2)c(C#N)c(-c2ccc(OCCO)cc2)c1C#N]

At RT, 100 mg (0.17 mmol) of 2-chloro-6-({(2-(4-chlorophenyl)-1,3-thiazol-4-ylmethyl}sulfanyl)-4-(4-(2-hydroxyethoxy)phenyl)pyridine-3,5-dicarbonitrile (Example 2A) and 0.17 ml (0.33 mmol) of ethylamine (2M solution in THF) were stirred in 2 ml of THF for 30 min. Another 0.17 ml (0.33 mmol) of ethylamine (2M solution in THF) was then added, and the mixture was stirred at RT for 2 h. About 15 ml of water were added to the reaction mixture, and the precipitate formed was filtered off, washed with water and dried under high vacuum. This gave 81 mg (89% of theory) of the desired target compound.

$^1$H-NMR (400 MHz, DMSO-$d_6$): δ=8.19 (q, 1H), 7.95 (d, 2H), 7.67 (s, 1H), 7.58 (d, 2H), 7.48 (d, 2H), 7.10 (d, 2H), 4.90 (t, 1H), 4.70 (s, 2H), 4.09 (t, 2H), 3.74 (q, 2H), 3.50 (Quintett, 2H), 1.09 (t, 3H).

LC-MS (Method 7): $R_t$=2.87 min; MS (ESIpos): m/z=548 (M+H)$^+$.

Example 4

2-({(2-(4-Chlorophenyl)-1,3-thiazol-4-ylmethyl}sulfanyl)-6-(dimethylamino)-4-(4-(2-hydroxyethoxy)phenyl)pyridine-3,5-dicarbonitrile

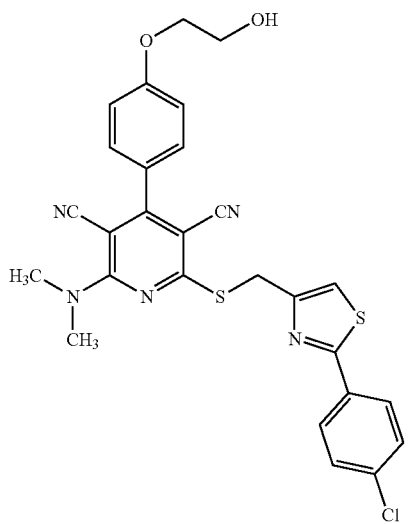 [SMILES: CN(C)c1nc(SCc2csc(-c3ccc(Cl)cc3)n2)c(C#N)c(-c2ccc(OCCO)cc2)c1C#N]

At 100° C., 80 mg (0.15 mmol) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A) and 28 mg (0.30 mmol) of methanesulfonamide were stirred in 1.5 ml of DMF overnight. After cooling, the crude product was purified by preparative HPLC (acetonitrile/water). This gave 41 mg (50% of theory) of the target compound.

$^1$H-NMR (400 MHz, DMSO-$d_6$): δ=7.96 (d, 2H), 7.70 (s, 1H), 7.59 (d, 2H), 7.51 (d, 2H), 7.10 (d, 2H), 4.90 (t, 1H), 4.70 (s, 2H), 4.09 (t, 2H), 3.74 (q, 2H), 3.34 (s, 6H).

LC-MS (Method 7): $R_t$=2.81 min; MS (ESIpos): m/z=548 (M+H)$^+$.

Example 5

2-({(2-(4-Chlorophenyl)-1,3-thiazol-4-yl)methyl}sulfanyl)-6-(ethyl(methyl)amino)-4-(4-(2-hydroxyethoxy)phenyl)pyridine-3,5-dicarbonitrile

Example 6

2-({(2-(4-Chlorophenyl)-1,3-thiazol-4-ylmethyl}sulfanyl)-6-(diethylamino)-4-(4-(2-hydroxyethoxy)phenyl)pyridine-3,5-dicarbonitrile

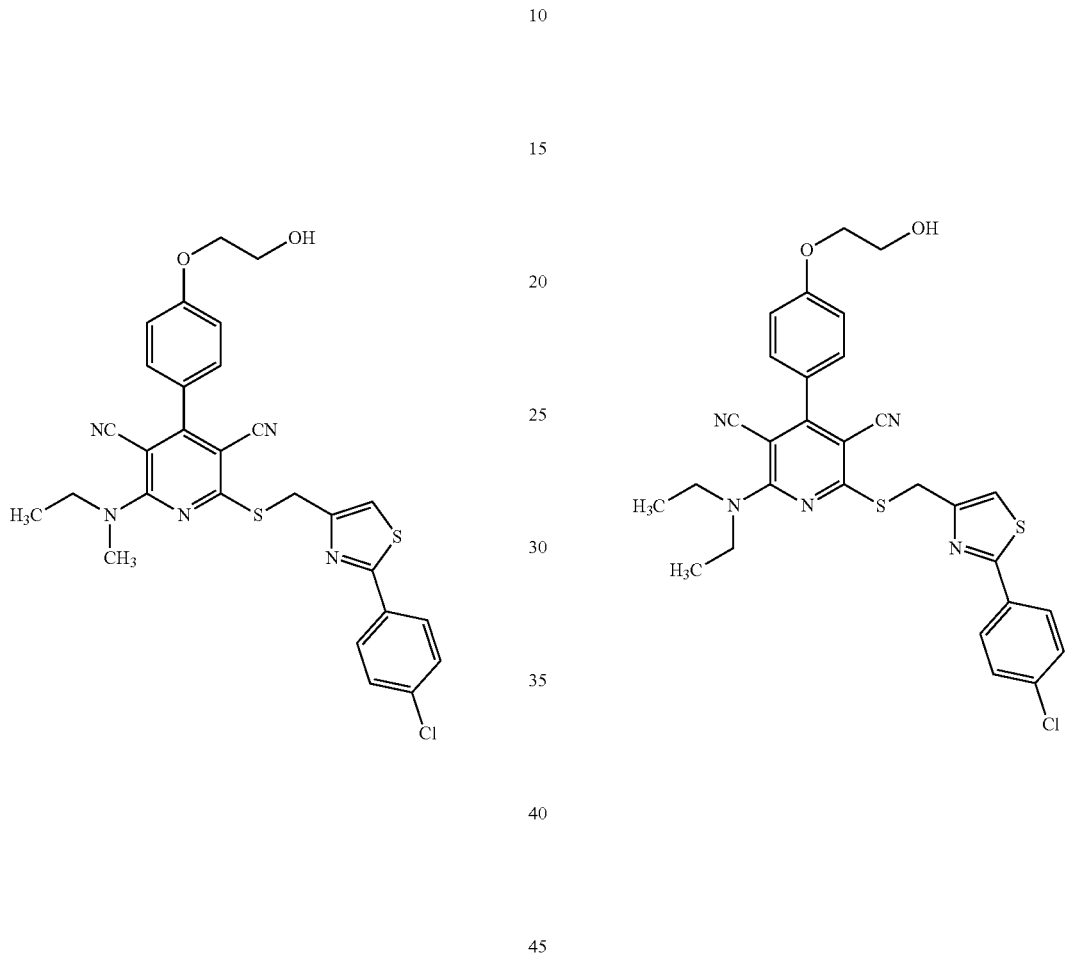

At RT, 60 mg (0.11 mmol) of 2-chloro-6-({(2-(4-chlorophenyl)-1,3-thiazol-4-ylmethyl}sulfanyl)-4-(4-(2-hydroxyethoxy)phenyl)pyridine-3,5-dicarbonitrile (Example 2A) and 0.019 ml (0.22 mmol) of N-ethylmethylamine were stirred in 1.5 ml of THF for 30 min. About 15 ml of water were added to the reaction mixture, and the aqueous phase was extracted 3× with ethyl acetate. The combined organic phases were washed once with sodium chloride solution, dried over sodium sulfate, concentrated by evaporation and dried under high vacuum. This gave 63 mg (99% of theory) of the desired target compound.

$^1$H-NMR (400 MHz, DMSO-$d_6$): δ=7.95 (d, 2H), 7.69 (s, 1H), 7.58 (d, 2H), 7.51 (d, 2H), 7.10 (d, 2H), 4.90 (t, 1H), 4.70 (s, 2H), 4.09 (t, 2H), 3.80-3.70 (m, 4H), 3.31 (s, 3H), 1.19 (t, 3H).

LC-MS (Method 3): $R_t$=3.02 min; MS (ESIpos): m/z=562 (M+H)$^+$.

At RT, 60 mg (0.11 mmol) of 2-chloro-6-({(2-(4-chlorophenyl)-1,3-thiazol-4-ylmethyl}sulfanyl)-4-(4-(2-hydroxyethoxy)phenyl)pyridine-3,5-dicarbonitrile (Example 2A) and 0.023 ml (0.22 mmol) of diethylamine were stirred in 1.5 ml of THF for 30 min. About 15 ml of water were added to the reaction mixture, and the aqueous phase was extracted 3× with ethyl acetate. The combined organic phases were washed once with saturated aqueous sodium chloride solution, dried over sodium sulfate, concentrated by evaporation and dried under high vacuum. This gave 67 mg (99% of theory, purity 95%) of the desired target compound.

$^1$H-NMR (400 MHz, DMSO-$d_6$): δ=7.95 (d, 2H), 7.70 (s, 1H), 7.59 (d, 2H), 7.49 (d, 2H), 7.10 (d, 2H), 4.91 (t, 1H), 4.70 (s, 2H), 4.09 (t, 2H), 3.80-3.70 (m, 6H), 3.31 (s, 3H), 1.20 (t, 6H).

LC-MS (Method 3): $R_t$=3.11 min; MS (ESIpos): m/z=576 (M+H)$^+$.

Example 7

2-({(2-(4-Chlorophenyl)-1,3-thiazol-4-ylmethyl}sulfanyl)-4-(4-(2-hydroxyethoxy)phenyl)-6-(propan-2-ylamino)pyridine-3,5-dicarbonitrile

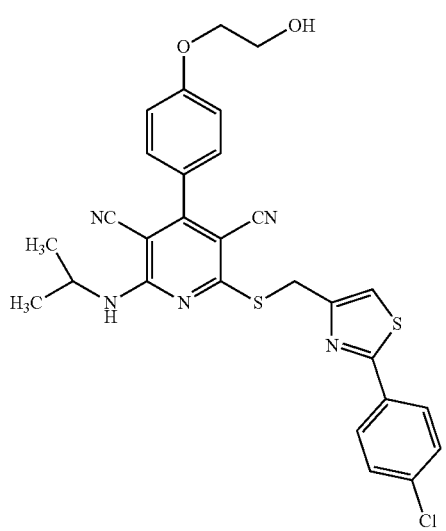 [SMILES: CC(C)Nc1nc(SCc2csc(-c3ccc(Cl)cc3)n2)c(C#N)c(-c2ccc(OCCO)cc2)c1C#N]

At RT, 60 mg (0.11 mmol) of 2-chloro-6-({(2-(4-chlorophenyl)-1,3-thiazol-4-ylmethyl}sulfanyl)-4-(4-(2-hydroxyethoxy)phenyl)pyridine-3,5-dicarbonitrile (Example 2A) and 0.011 ml (0.13 mmol) of isopropylamine were stirred in 1.5 ml of THF for 60 min. Another 11 µl (0.13 mmol) of isopropylamine were then added, and the mixture was stirred at RT for another 60 min. About 10 ml of water were added to the reaction mixture, and the precipitate formed was filtered off, washed with water and dried under high vacuum. This gave 35 mg (56% of theory) of the desired target compound.

$^1$H-NMR (400 MHz, DMSO-$d_6$): δ=7.96 (d, 2H), 7.80 (d, 1H), 7.67 (s, 1H), 7.58 (d, 2H), 7.48 (d, 2H), 7.10 (d, 2H), 4.90 (t, 1H), 4.68 (s, 2H), 4.50-4.39 (m, 1H), 4.09 (t, 2H), 3.74 (q, 2H), 1.13 (d, 6H).

LC-MS (Method 7): $R_t$=2.98 min; MS (ESIpos): m/z=562 (M+H)$^+$.

Example 8

2-(Azetidin-1-yl)-6-({(2-(4-chlorophenyl)-1,3-thiazol-4-ylmethyl}sulfanyl)-4-(4-(2-hydroxyethoxy)phenyl)pyridine-3,5-dicarbonitrile

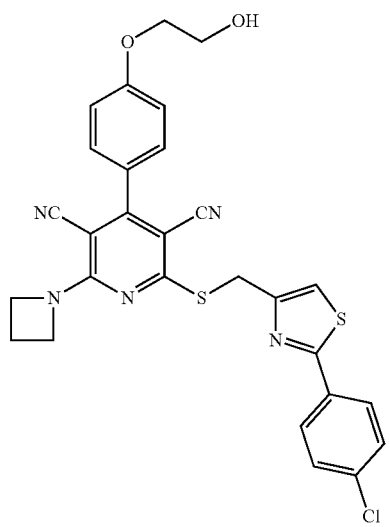 [SMILES: N#Cc1c(SCc2csc(-c3ccc(Cl)cc3)n2)nc(N2CCC2)c(C#N)c1-c1ccc(OCCO)cc1]

At RT, 100 mg (0.19 mmol) of 2-chloro-6-({(2-(4-chlorophenyl)-1,3-thiazol-4-ylmethyl}sulfanyl)-4-(4-(2-hydroxyethoxy)phenyl)pyridine-3,5-dicarbonitrile (Example 2A) and 0.015 ml (0.22 mmol) of azetidine were stirred in 2.5 ml of THF overnight. Another 0.025 ml (0.36 mmol) of azetidine was then added, and the mixture was once more stirred at RT overnight. About 10 ml of water were added to the reaction mixture, and the precipitate formed was filtered off, washed with water and dried under high vacuum. This gave 85 mg (82% of theory) of the desired target compound.

$^1$H-NMR (400 MHz, DMSO-$d_6$): δ=7.95 (d, 2H), 7.68 (s, 1H), 7.59 (d, 2H), 7.47 (d, 2H), 7.10 (d, 2H), 4.90 (t, 1H), 4.68 (s, 2H), 4.48 (br s, 4H), 4.08 (t, 2H), 3.73 (q, 2H), 2.38 (Quintett, 2H).

LC-MS (Method 4): $R_t$=1.52 min; MS (ESIpos): m/z=560 (M+H)$^+$.

Example 9

2-({(2-(4-Chlorophenyl)-1,3-thiazol-4-ylmethyl}sulfanyl)-6-(cyclopropylamino)-4-(4-(2-hydroxyethoxy)phenyl)pyridine-3,5-dicarbonitrile

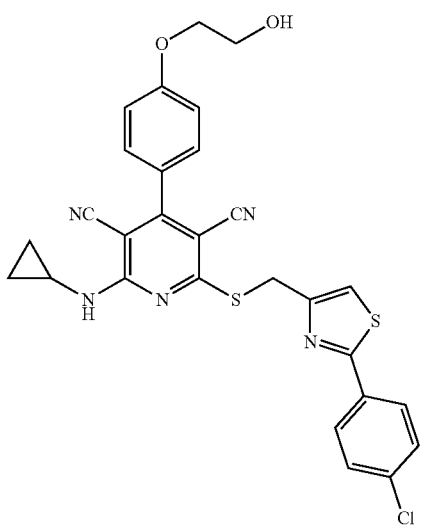 [SMILES: N#Cc1c(NC2CC2)nc(SCc2csc(-c3ccc(Cl)cc3)n2)c(C#N)c1-c1ccc(OCCO)cc1]

At RT, 50 mg (0.09 mmol) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A) and 0.013 ml (0.19 mmol) of cyclopropanamine were stirred in 1.3 ml of DMF overnight. The crude product was purified directly by preparative HPLC (acetonitrile/water). The collected product fractions were once more dissolved in 2 ml of DMF, 0.013 ml (0.19 mmol) of cyclopropanamine was added and the mixture was stirred at RT overnight. The crude product was then once more purified by preparative HPLC (acetonitrile/water). This gave 20 mg (39% of theory) of the desired target compound.

$^1$H-NMR (400 MHz, DMSO-$d_6$): δ=8.30 (br s, 1H), 7.94 (d, 2H), 7.68 (s, 1H), 7.59 (d, 2H), 7.48 (d, 2H), 7.10 (d, 2H), 4.90 (t, 1H), 4.78 (s, 2H), 4.09 (t, 2H), 3.74 (q, 2H), 3.01-2.94 (m, 1H), 0.78-0.65 (m, 4H).

LC-MS (Method 6): R$_t$=3.05 min; MS (ESIpos): m/z=560 (M+H)$^+$.

Example 10

2-({(2-(4-Chlorophenyl)-1,3-thiazol-4-yl)methyl}sulfanyl)-6-(cyclobutylamino)-4-(4-(2-hydroxyethoxy)phenyl)pyridine-3,5-dicarbonitrile

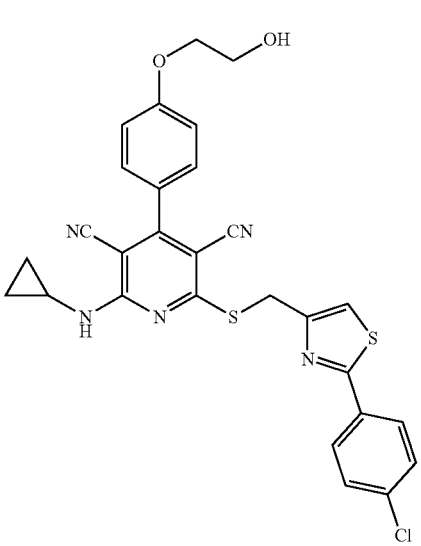 [SMILES: N#Cc1c(NC2CC2)nc(SCc2csc(-c3ccc(Cl)cc3)n2)c(C#N)c1-c1ccc(OCCO)cc1]

At RT, 80 mg (0.15 mmol) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A) and 26 μl (0.30 mmol) of cyclobutanamine were stirred in 1.5 ml of DMF overnight. The reaction mixture was then purified by preparative HPLC (acetonitrile/water). This gave 56 mg (65% of theory) of the target compound.

$^1$H-NMR (400 MHz, DMSO-$d_6$): δ=8.28 (d, 1H), 7.97 (d, 2H), 7.68 (s, 1H), 7.59 (d, 2H), 7.48 (d, 2H), 7.11 (d, 2H), 4.90 (t, 1H), 4.70 (s, 2H), 4.59 (Quintett, 1H), 4.09 (t, 2H), 3.74 (q, 2H), 2.20-2.10 (m, 4H), 1.68-1.49 (m, 2H).

LC-MS (Method 6): R$_t$=3.18 min; MS (ESIpos): m/z=574 (M+H)$^+$.

Example 11

2-({(2-(4-Chlorophenyl)-1,3-thiazol-4-yl)methyl}sulfanyl)-4-(4-(2-hydroxyethoxy)phenyl)-6-((3,3,3-trifluoropropyl)amino)pyridine-3,5-dicarbonitrile

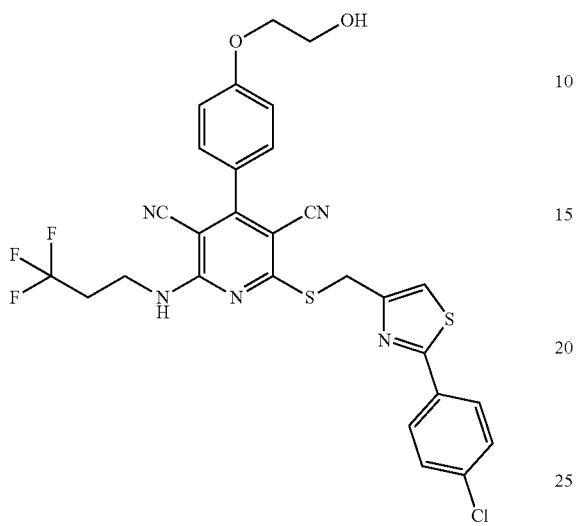

At 100° C., 150 mg (0.21 mmol, purity about 74%) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A) and 93 mg (0.82 mmol) of 3,3,3-trifluoropropan-1-amine were stirred in 2.0 ml of DMF for 2 h. The reaction mixture was then diluted with about 1 ml of water and about 3 ml of THF and purified by preparative HPLC (acetonitrile/water+0.1% TFA). This gave 105 mg (83% of theory) of the target compound.

$^1$H-NMR (400 MHz, DMSO-$d_6$): δ=8.32 (t, 1H), 7.93 (d, 2H), 7.68 (s, 1H), 7.58 (d, 2H), 7.49 (d, 2H), 7.12 (d, 2H), 4.91 (t, 1H), 4.73 (s, 2H), 4.09 (t, 2H), 3.78-3.69 (m, 4H), 2.61-2.49 (m, 2H).

LC-MS (Method 2): $R_t$=1.34 min; MS (ESIpos): m/z=616 (M+H)$^+$.

Example 12

2-({(2-(4-Chlorophenyl)-1,3-thiazol-4-ylmethyl}sulfanyl)-4-(4-(2-hydroxyethoxy)phenyl)-6-(propylamino)pyridine-3,5-dicarbonitrile

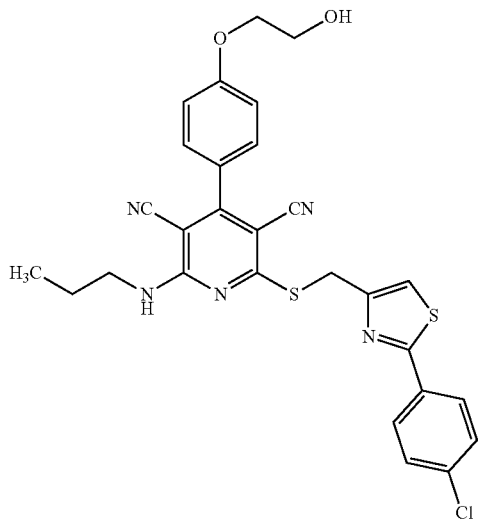 [SMILES: CCCNc1nc(SCc2csc(-c3ccc(Cl)cc3)n2)c(C#N)c(-c2ccc(OCCO)cc2)c1C#N]

At RT, 100 mg (0.19 mmol) of 2-chloro-6-({(2-(4-chlorophenyl)-1,3-thiazol-4-ylmethyl}sulfanyl)-4-(4-(2-hydroxyethoxy)phenyl)pyridine-3,5-dicarbonitrile (Example 2A) and 30 µl (0.37 mmol) of n-propylamine were stirred in 2.5 ml of THF for 2 h. The reaction mixture was then purified by preparative HPLC (acetonitrile/water+0.1% TFA). This gave 67 mg (64% of theory) of the target compound.

$^1$H-NMR (400 MHz, DMSO-$d_6$): δ=8.20 (t, 1H), 7.94 (d, 2H), 7.63 (s, 1H), 7.58 (d, 2H), 7.49 (d, 2H), 7.11 (d, 2H), 4.90 (t, 1H), 4.70 (s, 2H), 4.09 (t, 2H), 3.74 (q, 2H), 3.43-3.34 (m, 2H), 1.49 (Quintett, 2H), 0.78 (t, 3H).

LC-MS (Method 2): $R_t$=1.40 min; MS (ESIpos): m/z=562 (M+H)$^+$.

Example 13

2-({(2-(4-Chlorophenyl)-1,3-thiazol-4-ylmethyl}sulfanyl)-4-(4-(2-hydroxyethoxy)phenyl)-6-(piperidin-1-yl)pyridine-3,5-dicarbonitrile

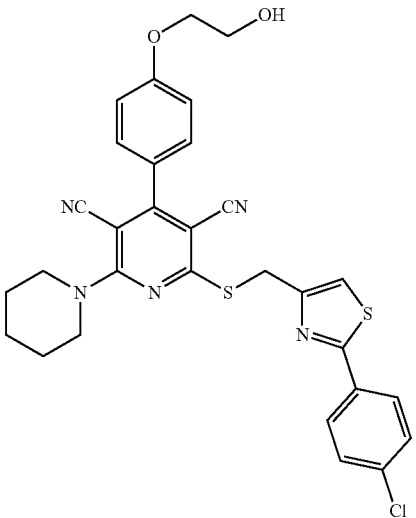 [SMILES: N#Cc1c(SCc2csc(-c3ccc(Cl)cc3)n2)nc(N2CCCCC2)c(C#N)c1-c1ccc(OCCO)cc1]

At RT, 300 mg (0.41 mmol, purity about 74%) of 2-chloro-6-({(2-(4-chlorophenyl)-1,3-thiazol-4-ylmethyl}sulfanyl)-4-(4-(2-hydroxyethoxy)phenyl)pyridine-3,5-dicarbonitrile (Example 2A) and 163 µl (1.65 mmol) of piperidine were stirred in 5.6 ml of THF for 2 h. The reaction mixture was then diluted with about 1 ml of water and about 3 ml of THF and purified by preparative HPLC (acetonitrile/water+0.1% TFA). This gave 215 mg (89% of theory) of the target compound.

$^1$H-NMR (400 MHz, DMSO-$d_6$): δ=7.96 (d, 2H), 7.69 (s, 1H), 7.58 (d, 2H), 7.54 (d, 2H), 7.11 (d, 2H), 4.90 (br s, 1H), 4.69 (s, 2H), 4.09 (t, 2H), 3.88-3.78 (m, 4H), 3.74 (t, 2H), 1.70-1.54 (m, 6H).

LC-MS (Method 2): $R_t$=1.45 min; MS (ESIpos): m/z=588 (M+H)$^+$.

The examples listed in Table 4 are prepared analogously to Example 13 from the appropriate starting materials. The amount of amine added is 2.2-4.0 equivalents based on the 2-chloro-6-({(2-(4-chlorophenyl)-1,3-thiazol-4-ylmethyl}sulfanyl)-4-(4-(2-hydroxyethoxy)phenyl)pyridine-3,5-dicarbonitrile (Example 2A):

TABLE 4
| Example No. | Structure (yield) | LC-MS: R$_t$ (min) (Method); MS (ESI): m/z (M + H)$^+$ | $^1$H-NMR (DMSO-d$_6$) |
|---|---|---|---|
| 14 | 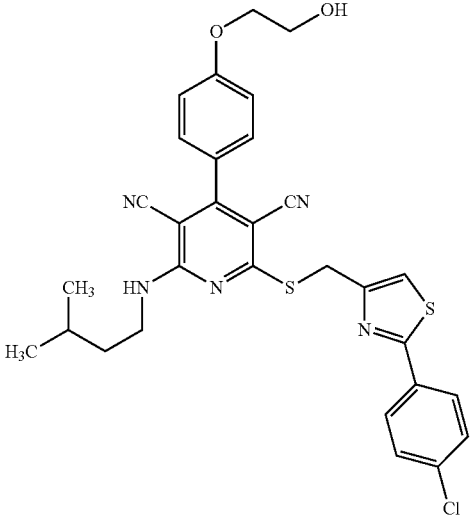 [SMILES: CC(C)CCNc1nc(SCc2csc(-c3ccc(Cl)cc3)n2)c(C#N)c(-c2ccc(OCCO)cc2)c1C#N]<br>(34% of theory) | 1.69 min (Method 4); m/z = 590 | δ (400 MHz) = 8.20 (t, 1H), 7.95 (d, 2H), 7.64 (s, 1H), 7.58 (d, 2H), 7.50 (d, 2H), 7.11 (d, 2H), 4.90 (t, 1H), 4.71 (s, 2H), 4.08 (t, 2H), 3.74 (q, 2H), 3.48 (q, 2H), 1.51 (septet, 1H), 1.39 (q, 2H), 0.80 (d, 6H). |
| 15 | 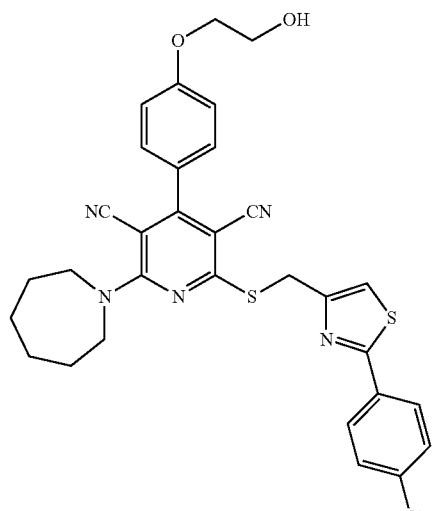<br>(93% of theory) | 1.45 min (Method 2); m/z = 602 | δ (400 MHz) = 7.94 (d, 2H), 7.69 (s, 1H), 7.58 (d, 2H), 7.50 (d, 2H), 7.10 (d, 2H), 4.69 (s, 2H), 4.09 (t, 2H), 3.92-3.59 (m, 7H), 1.78 (br s, 4H), 1.50 (br s, 4H). |

TABLE 4-continued
| Example No. | Structure (yield) | LC-MS: R$_t$ (min) (Method); MS (ESI): m/z (M + H)$^+$ | $^1$H-NMR (DMSO-d$_6$) |
|---|---|---|---|
| 16 | 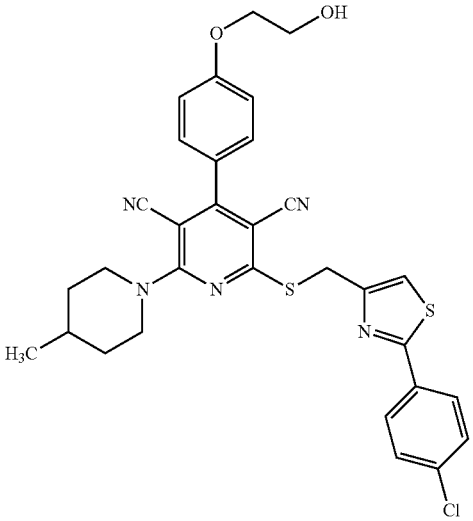 [SMILES: CC1CCN(c2nc(SCc3csc(-c4ccc(Cl)cc4)n3)c(C#N)c(-c3ccc(OCCO)cc3)c2C#N)CC1] (94% of theory) | 1.69 min (Method 4); m/z = 602 | δ (400 MHz) = 7.94 (d, 2H), 7.68 (s, 1H), 7.58 (d, 2H), 7.52 (d, 2H), 7.10 (d, 2H), 4.69 (s, 2H), 4.55 (d, 2H), 4.09 (t, 2H), 3.76 (t, 3H), 3.18 (t, 2H), 1.72-1.60 (m, 3H), 1.11 (q, 2H), 0.86 (d, 3H). |
| 17 | 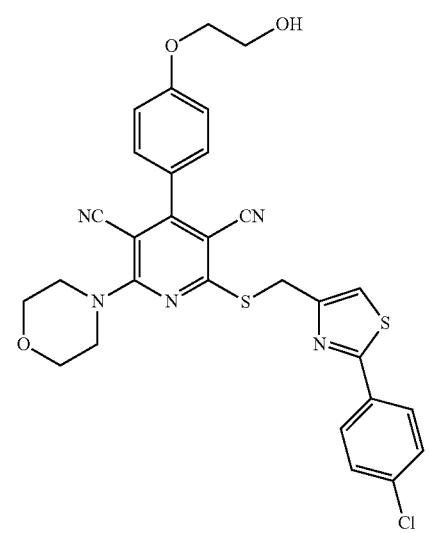 [SMILES: N#Cc1c(SCc2csc(-c3ccc(Cl)cc3)n2)nc(N2CCOCC2)c(C#N)c1-c1ccc(OCCO)cc1] (95% of theory) | 1.30 min (Method 2); m/z = 590 | δ (400 MHz) = 7.95 (d, 2H), 7.70 (s, 1H), 7.59 (d, 2H), 7.54 (d, 2H), 7.11 (d, 2H), 4.69 (s, 2H), 4.09 (t, 2H), 3.93-3.87 (m, 4H), 3.73 (t, 2H), 3.71-3.62 (m, 4H). |

TABLE 4-continued
| Example No. | Structure (yield) | LC-MS: R$_t$ (min) (Method); MS (ESI): m/z (M + H)$^+$ | $^1$H-NMR (DMSO-d$_6$) |
|---|---|---|---|
| 18 | 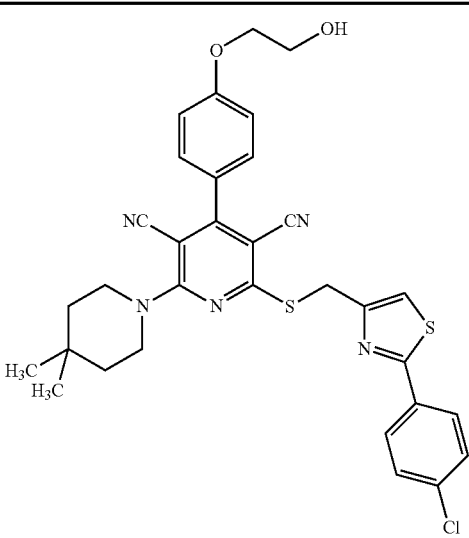 (96% of theory) | 1.52 min (Method 2); m/z = 616 | δ (400 MHz) = 7.95 (d, 2H), 7.67 (s, 1H), 7.59 (d, 2H), 7.54 (d, 2H), 7.11 (d, 2H), 4.68 (s, 2H), 4.09 (t, 2H), 3.86-3.80 (m, 4H), 3.73 (t, 2H), 1.40-1.36 (m, 4H), 0.92 (s, 6H). |
| 19 | 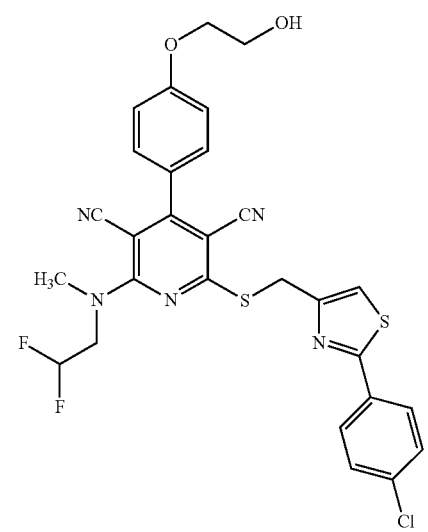 [SMILES: CN(CC(F)F)c1nc(SCc2csc(-c3ccc(Cl)cc3)n2)c(C#N)c(-c2ccc(OCCO)cc2)c1C#N] (63% of theory) | 1.32 min (Method 2); m/z = 598 | δ (400 MHz) = 7.94 (d, 2H), 7.70 (s, 1H), 7.58 (d, 2H), 7.54 (d, 2H), 7.11 (d, 2H), 6.50-6.18 (m, 1H), 4.70 (s, 2H), 4.32-4.20 (m, 2H), 4.09 (t, 2H), 3.74 (t, 2H), 3.49 (s, 3H). |

TABLE 4-continued
| Example No. | Structure (yield) | LC-MS: R$_t$(min) (Method); MS (ESI): m/z (M + H)$^+$ | $^1$H-NMR (DMSO-d$_6$) |
|---|---|---|---|
| 20 | 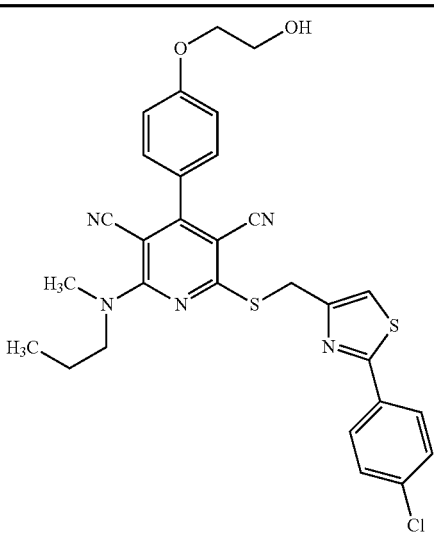 (86% of theory) | 1.40 min (Method 2); m/z = 576 | δ (400 MHz) = 7.95 (d, 2H), 7.68 (s, 1H), 7.58 (d, 2H), 7.53 (d, 2H), 7.11 (d, 2H), 4.69 (s, 2H), 4.09 (t, 2H), 3.76-3.60 (m, 4H), 3.32 (s, 3H), 1.62 (Sextett, 2H), 0.80 (t, 3H). |
| 21 | 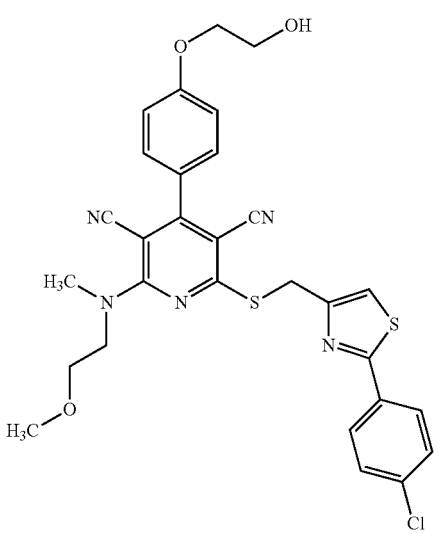 [SMILES: COCCN(C)c1nc(SCc2csc(-c3ccc(Cl)cc3)n2)c(C#N)c(-c2ccc(OCCO)cc2)c1C#N] (87% of theory) | 1.32 min (Method 2); m/z = 592 | δ (400 MHz) = 7.96 (d, 2H), 7.69 (s, 1H), 7.59 (d, 2H), 7.52 (d, 2H), 7.11 (d, 2H), 4.69 (s, 2H), 4.09 (t, 2H), 3.96 (t, 2H), 3.74 (t, 2H), 3.54 (t, 2H), 3.40 (s, 3H), 3.20 (s, 3H). |

TABLE 4-continued
| Example No. | Structure (yield) | LC-MS: $R_t$ (min) (Method); MS (ESI): m/z (M + H)+ | $^1$H-NMR (DMSO-$d_6$) |
|---|---|---|---|
| 22 | 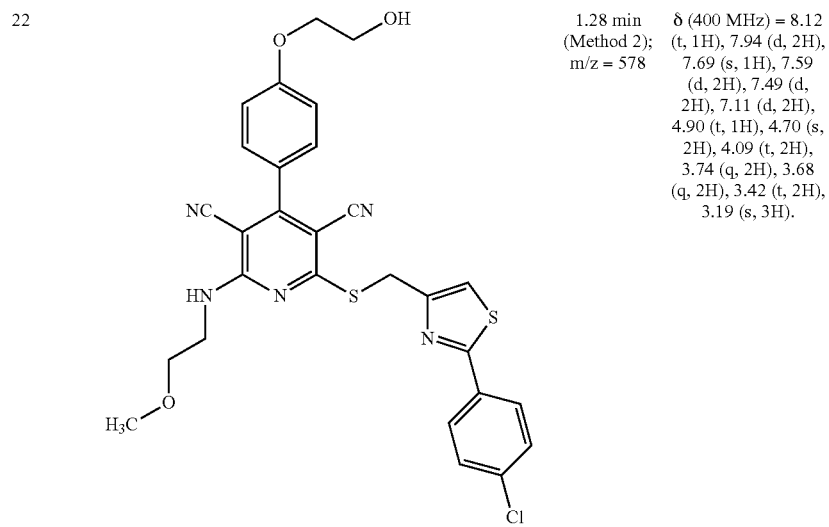<br>(87% of theory) | 1.28 min (Method 2); m/z = 578 | δ (400 MHz) = 8.12 (t, 1H), 7.94 (d, 2H), 7.69 (s, 1H), 7.59 (d, 2H), 7.49 (d, 2H), 7.11 (d, 2H), 4.90 (t, 1H), 4.70 (s, 2H), 4.09 (t, 2H), 3.74 (q, 2H), 3.68 (q, 2H), 3.42 (t, 2H), 3.19 (s, 3H). |
| 23 | 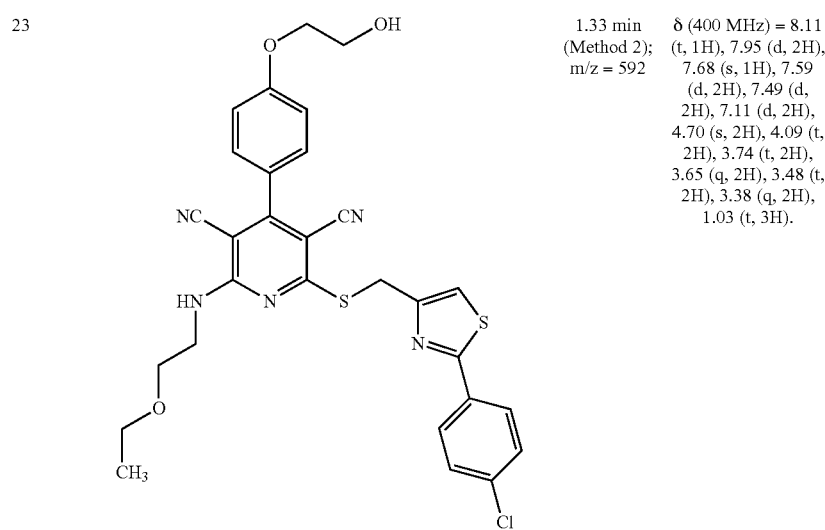<br>(88% of theory) | 1.33 min (Method 2); m/z = 592 | δ (400 MHz) = 8.11 (t, 1H), 7.95 (d, 2H), 7.68 (s, 1H), 7.59 (d, 2H), 7.49 (d, 2H), 7.11 (d, 2H), 4.70 (s, 2H), 4.09 (t, 2H), 3.74 (t, 2H), 3.65 (q, 2H), 3.48 (t, 2H), 3.38 (q, 2H), 1.03 (t, 3H). |

TABLE 4-continued
| Example No. | Structure (yield) | LC-MS: R_t (min) (Method); MS (ESI): m/z (M + H)+ | $^1$H-NMR (DMSO-d$_6$) |
|---|---|---|---|
| 24 | 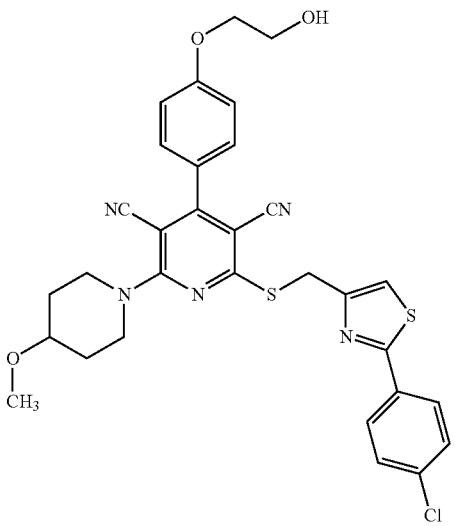 [SMILES: COC1CCN(c2nc(SCc3csc(-c4ccc(Cl)cc4)n3)c(C#N)c(-c3ccc(OCCO)cc3)c2C#N)CC1]<br>(35% of theory) | 1.37 min (Method 2); m/z = 618 | δ (400 MHz) = 7.96 (d, 2H), 7.68 (s, 1H), 7.59 (d, 2H), 7.55 (d, 2H), 7.10 (d, 2H), 4.68 (s, 2H), 4.13-4.05 (m, 4H), 3.72 (t, 2H), 3.67-3.58 (m, 2H), 3.50-3.38 (m, 1H), 3.23 (s, 3H), 1.96-1.87 (m, 2H), 1.56-1.46 (m, 2H). |
| 25 | 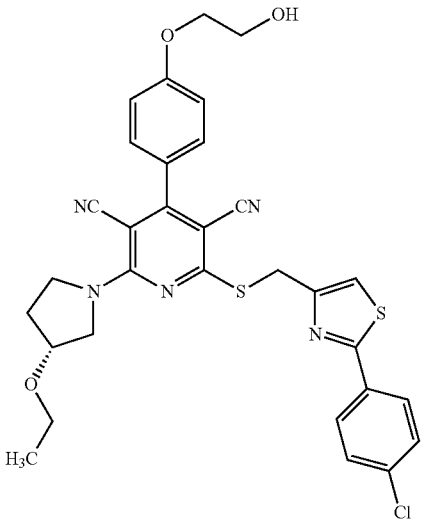 [SMILES: CCO[C@@H]1CCN(c2nc(SCc3csc(-c4ccc(Cl)cc4)n3)c(C#N)c(-c3ccc(OCCO)cc3)c2C#N)C1]<br>(68% of theory) | 1.58 min (Method 4); m/z = 618 | δ (400 MHz) = 7.95 (d, 2H), 7.69 (s, 1H), 7.59 (d, 2H), 7.49 (d, 2H), 7.10 (d, 2H), 4.70 (s, 2H), 4.14 (br s, 1H), 4.09 (t, 2H), 3.99-3.70 (m, 6H), 3.48-3.34 (m, 2H), 2.12-1.93 (m, 2H), 1.05 (t, 3H). |

Example 26

2-({(2-(4-Chlorophenyl)-1,3-thiazol-4-yl)methyl}sulfanyl)-6-(3,3-difluoropyrrolidin-1-yl)-4-(4-(2-hydroxyethoxy)phenyl)pyridine-3,5-dicarbonitrile

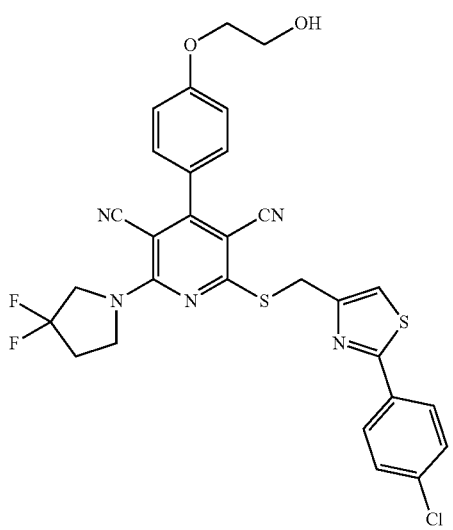 [SMILES: N#Cc1c(SCc2csc(-c3ccc(Cl)cc3)n2)nc(N2CCC(F)(F)C2)c(C#N)c1-c1ccc(OCCO)cc1]

At RT, 100 mg (0.19 mmol) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A) and 53 mg (0.37 mmol) of 3,3-difluoropyrrolidine hydrochloride and 52 μl (0.37 mmol) of triethylamine were stirred in 2.5 ml of THF for 2 h. The reaction mixture was then diluted with about 1 ml of water and about 3 ml of THF and purified by preparative HPLC (acetonitrile/water+0.1% TFA). This gave 62 mg (54% of theory) of the target compound.

$^1$H-NMR (400 MHz, DMSO-$d_6$): δ=7.92 (d, 2H), 7.71 (s, 1H), 7.58 (d, 2H), 7.50 (d, 2H), 7.11 (d, 2H), 4.72 (s, 2H), 4.29 (t, 2H), 4.17-4.07 (m, 4H), 3.73 (t, 2H), 2.62-2.50 (m, 2H).

LC-MS (Method 2): $R_t$=1.35 min; MS (ESIpos): m/z=610 $(M+H)^+$.

The examples listed in Table 5 are prepared analogously to Example 26 from the appropriate starting materials. The amount of amine added is 1.5-2.0 equivalents, that of triethylamine 2.0-3.0 equivalents based on the 2-chloro-6-({(2-(4-chlorophenyl)-1,3-thiazol-4-ylmethyl}sulfanyl)-4-(4-(2-hydroxyethoxy)phenyl)pyridine-3,5-dicarbonitrile (Example 2A):

TABLE 5

| Example No. | Structure (yield) | LC-MS: $R_t$ (min) (Method); MS (ESI): m/z $(M + H)^+$ | $^1$H-NMR (DMSO-$d_6$) |
|---|---|---|---|
| 27 | (48% of theory) | 1.36 min (Method 2); m/z = 624 | δ (400 MHz) = 7.95 (d, 2H), 7.70 (s, 1H), 7.59 (d, 2H), 7.55 (d, 2H), 7.12 (d, 2H), 4.90 (t, 1H), 4.71 (s, 2H), 4.09 (t, 2H), 4.02-3.93 (m, 4H), 3.74 (q, 2H), 2.19-2.05 (m, 4H). |

TABLE 5-continued
| Example No. | Structure (yield) | LC-MS: R$_t$ (min) (Method); MS (ESI): m/z (M + H)$^+$ | $^1$H-NMR (DMSO-d$_6$) |
|---|---|---|---|
| 28 | 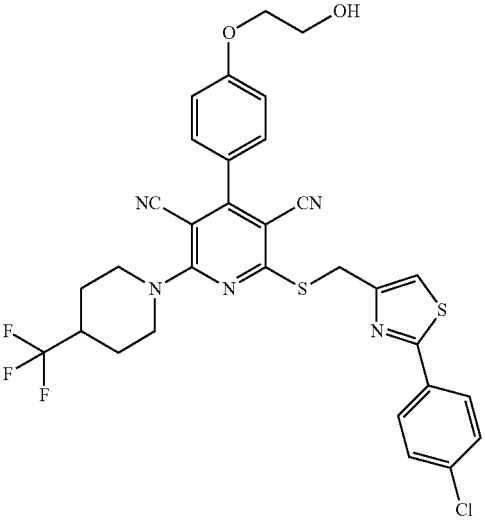 [SMILES: N#Cc1c(SCc2csc(-c3ccc(Cl)cc3)n2)nc(N2CCC(C(F)(F)F)CC2)c(C#N)c1-c1ccc(OCCO)cc1] (87% of theory) | 1.63 min (Method 4); m/z = 656 | δ (400 MHz) = 7.95 (d, 2H), 7.69 (s, 1H), 7.58 (d, 2H), 7.56 (d, 2H), 7.11 (d, 2H), 4.90 (br s, 1H), 4.70 (s, 2H), 4.64 (d, 2H), 4.09 (t, 2H), 3.74 (t, 2H), 3.22 (t, 2H), 2.78-2.62 (m, 1H), 1.91-1.82 (m, 2H), 1.50-1.39 (m, 2H). |
| 29 | 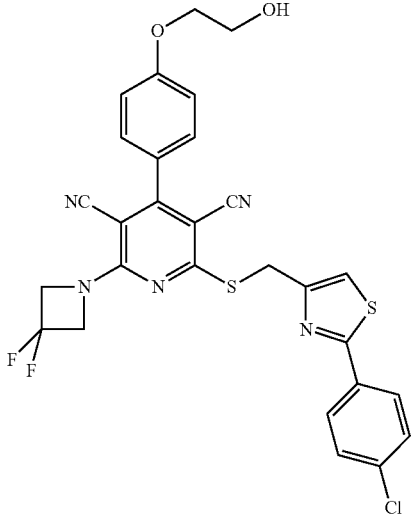 [SMILES: N#Cc1c(SCc2csc(-c3ccc(Cl)cc3)n2)nc(N2CC(F)(F)C2)c(C#N)c1-c1ccc(OCCO)cc1] (89% of theory) | 1.36 min (Method 2); m/z = 596 | δ (400 MHz) = 7.96 (d, 2H), 7.71 (s, 1H), 7.58 (d, 2H), 7.49 (d, 2H), 7.12 (d, 2H), 4.89 (t, 4H), 4.71 (s, 2H), 4.09 (t, 2H), 3.74 (t, 2H). |

TABLE 5-continued

| Example No. | Structure (yield) | LC-MS: R$_t$ (min) (Method); MS (ESI): m/z (M + H)$^+$ | $^1$H-NMR (DMSO-d$_6$) |
|---|---|---|---|
| 30 | 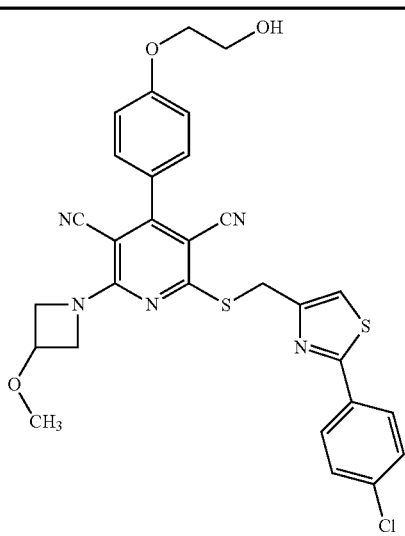<br>(76% of theory) | 1.32 min (Method 2); m/z = 590 | δ (400 MHz) = 7.96 (d, 2H), 7.69 (s, 1H), 7.58 (d, 2H), 7.47 (d, 2H), 7.10 (d, 2H), 4.85 (br s, 1H), 4.72-4.55 (m, 4H), 4.32-4.28 (m, 1H), 4.27-4.15 (m, 2H), 4.09 (t, 2H), 3.74 (t, 2H), 3.24 (s, 3H). |

Example 31

2-({(2-(4-Chlorophenyl)-1,3-thiazol-4-yl)methyl}sulfanyl)-6-(3,3-difluoropiperidin-1-yl)-4-(4-(2-hydroxyethoxy)phenyl)pyridine-3,5-dicarbonitrile

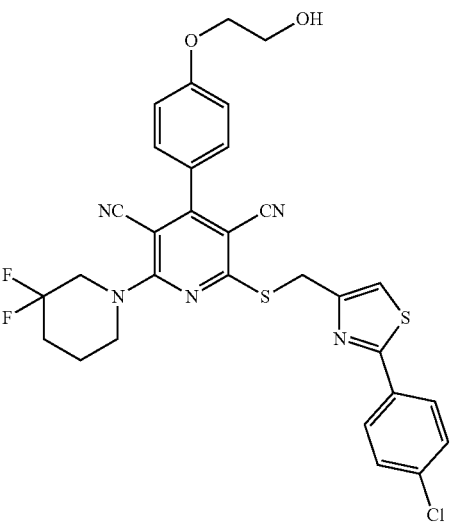 [SMILES: N#Cc1c(SCc2csc(-c3ccc(Cl)cc3)n2)nc(N2CCCC(F)(F)C2)c(C#N)c1-c1ccc(OCCO)cc1]

At RT, 150 mg (0.20 mmol, purity about 74%) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A), 64 mg (0.41 mmol) of 3,3-difluoropiperidine hydrochloride and 57 µl (0.41 mmol) of triethylamine were stirred in 3 ml of THF for 2 h. The reaction mixture was then diluted with about 1 ml of water and about 3 ml of THF and purified by preparative HPLC (acetonitrile/water+0.1% TFA). This gave 90 mg (71% of theory) of the target compound.

$^1$H-NMR (400 MHz, DMSO-d$_6$): δ=7.95 (d, 2H), 7.69 (s, 1H), 7.56 (d, 4H), 7.12 (d, 2H), 4.90 (br s, 1H), 4.71 (s, 2H), 4.17 (t, 2H), 4.09 (t, 2H), 3.92-3.85 (m, 2H), 3.74 (t, 2H), 2.20-2.07 (m, 2H), 1.86-1.78 (m, 2H).

LC-MS (Method 2): R$_t$=1.34 min; MS (ESIpos): m/z=624 (M+H)$^+$.

Example 32

2-({(2-(4-Chlorophenyl)-1,3-thiazol-4-yl)methyl}sulfanyl)-4-(4-(2-hydroxyethoxy)phenyl)-6-((2,2,2-trifluoroethyl)amino)pyridine-3,5-dicarbonitrile

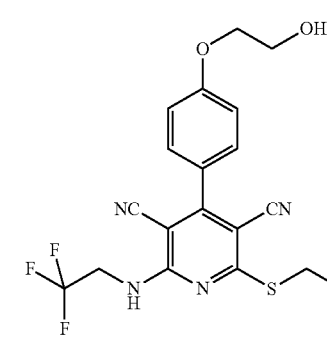

140 mg (0.260 mmol) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A) and 52 mg (0.519 mmol) of 2,2,2-trifluoro-1-aminoethane were dissolved in 2 ml of tetrahydrofuran and stirred at room temperature overnight. A further 52 mg (0.519 mmol) of 2,2,2-trifluoro-1-aminoethane were added and stirring was continued for 6 hours, after which the reaction mixture was heated to 50° C. and stirred at this temperature overnight. A further 52 mg (0.519 mmol) of 2,2,2-trifluoro-1-aminoethane were added. The mixture was then stirred initially at 50° C. for 2 hours and then under reflux for four hours. Without further work-up, the reaction mixture was purified by preparative HPLC. 36 mg (yield: 23%) of the target compound were obtained.

$^1$H-NMR (400 MHz, DMSO-$d_6$): δ=8.59 (t, 1H), 7.95 (d, 2H), 7.69 (s, 1H), 7.58 (d, 2H), 7.53 (d, 2H), 7.13 (d, 2H), 4.92 (t, 1H), 4.71 (s, 2H), 4.31 (m, 2H), 4.09 (t, 2H), 3.74 (m, 2H).

LC-MS (Method 1): $R_t$=2.77 min; MS (ESIpos): m/z=602 (M+H)$^+$.

Example 33

2-({(2-(4-Chlorophenyl)-1,3-thiazol-4-yl)methyl}sulfanyl)-6-((2-fluoroethyl)amino)-4-(4-(2-hydroxyethoxy)phenyl)pyridine-3,5-dicarbonitrile

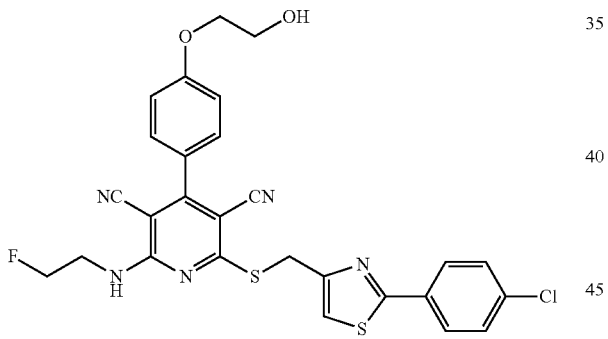

140 mg (0.260 mmol) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A), 52 mg (0.519 mmol) of 2-fluoroethylamine hydrochloride and 67 mg (0.519 mmol) of N,N-diisopropylethylamine were dissolved in 2 ml of tetrahydrofuran and stirred at room temperature overnight. Without further work-up, the reaction mixture was purified by preparative HPLC. 78 mg (yield: 53% of theory) of the target compound were obtained.

$^1$H-NMR (400 MHz, DMSO-$d_6$): δ=8.29 (t, 1H), 7.95 (d, 2H), 7.68 (s, 1H), 7.57 (d, 2H), 7.50 (d, 2H), 7.12 (d, 2H), 4.91 (t, 1H), 4.69 (s, 2H), 4.59 (t, 1H), 4.47 (t, 1H), 4.08 (t, 2H), 3.84 (m, 1H), 3.80-3.73 (m, 3H).

LC-MS (Method 2): $R_t$=1.27 min; MS (ESIpos): m/z=566 (M+H)$^+$.

Example 34

2-({(2-(4-Chlorophenyl)-1,3-thiazol-4-yl)methyl}sulfanyl)-6-((2,2-difluoroethyl)amino)-4-(4-(2-hydroxyethoxy)phenyl)pyridine-3,5-dicarbonitrile

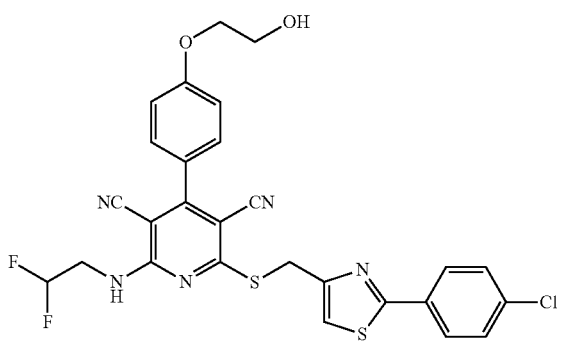 [SMILES: N#Cc1c(NCC(F)F)nc(SCc2csc(-c3ccc(Cl)cc3)n2)c(C#N)c1-c1ccc(OCCO)cc1]

140 mg (0.260 mmol) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A), 61 mg (0.519 mmol) of 2,2-difluoroethylamine hydrochloride and 67 mg (0.519 mmol) of N,N-diisopropylethylamine were dissolved in 2 ml of tetrahydrofuran and stirred at room temperature overnight. Without further work-up, the reaction mixture was purified by preparative HPLC. 77 mg (yield: 51% of theory) of the target compound were obtained.

$^1$H-NMR (400 MHz, DMSO-$d_6$): δ=8.41 (m, 1H), 7.95 (d, 2H), 7.69 (s, 1H), 7.57 (d, 2H), 7.51 (d, 2H), 7.13 (d, 2H), 6.17 (tt, 1H), 4.92 (t, 1H), 4.72 (s, 2H), 4.09 (t, 2H), 3.90 (m, 2H), 3.75 (m, 2H).

LC-MS (Method 2): $R_t$=1.28 min; MS (ESIpos): m/z=584 (M+H)$^+$.

Example 35

2-({(2-(4-Chlorophenyl)-1,3-thiazol-4-yl)methyl}sulfanyl)-4-(4-(2-hydroxyethoxy)phenyl)-6-(methyl(2,2,2-trifluoroethyl)amino)pyridine-3,5-dicarbonitrile

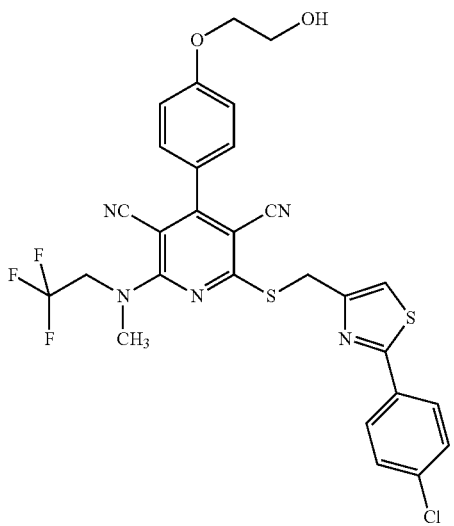 [SMILES: CN(CC(F)(F)F)c1nc(SCc2csc(-c3ccc(Cl)cc3)n2)c(C#N)c(-c2ccc(OCCO)cc2)c1C#N]

41 mg (0.27 mmol) of 2,2,2-trifluoro-N-methylethanamine hydrochloride were dissolved in 2 ml of DMF, 40 mg of Amberlyst A-21 were added and the mixture was stirred at RT for 30 min. The mixture was filtered off and added to 100 mg (0.14 mmol, purity about 74%) of 2-chloro-6-({(2-(4-chlorophenyl)-1,3-thiazol-4-yl)methyl}sulfanyl)-4-(4-(2-hydroxyethoxy)phenyl)pyridine-3,5-dicarbonitrile (Example 2A), and the solution was stirred at RT overnight. In a separate flask, another 82 mg (0.54 mmol) of 2,2,2-trifluoro-N-methylethanamine hydrochloride were then dissolved in 0.5 ml of DMF, 80 mg of Amberlyst A-21 were added and the mixture was stirred at RT for 30 min. The mixture was filtered off and added to the first solution. The reaction mixture obtained was stirred at RT overnight. The mixture was then warmed to 60° C., and the reaction mixture was stirred at this temperature overnight, after which it was heated to 100° C. After stirring at 100° C. overnight, the mixture was diluted with a little water/THF and purified by preparative HPLC (acetonitrile/water+0.1% TFA). This gave 64 mg (74% of theory) of the target compound.

$^1$H-NMR (400 MHz, DMSO-d$_6$): δ=7.94 (d, 2H), 7.70 (s, 1H), 7.58 (d, 2H), 7.56 (d, 2H), 7.11 (d, 2H), 4.90 (br s, 1H), 4.78 (q, 2H), 4.70 (s, 2H), 4.09 (t, 2H), 3.73 (t, 2H), 3.51 (s, 3H).

LC-MS (Method 2): R$_t$=1.36 min; MS (ESIpos): m/z=616 (M+H)$^+$.

Example 36

2-({(2-(4-Chlorophenyl)-1,3-thiazol-4-ylmethyl}sulfanyl)-6-(ethyl(2,2,2-trifluoroethyl)amino)-4-(4-(2-hydroxyethoxy)phenyl)pyridine-3,5-dicarbonitrile

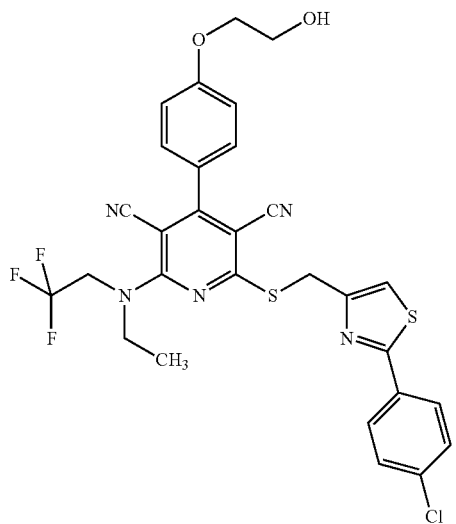 [SMILES: CCN(CC(F)(F)F)c1nc(SCc2csc(-c3ccc(Cl)cc3)n2)c(C#N)c(-c2ccc(OCCO)cc2)c1C#N]

133 mg (0.81 mmol) of N-ethyl-2,2,2-trifluoroethanamine hydrochloride were dissolved in 2 ml of DMF, 130 mg Amberlyst A-21 were added and the mixture was stirred at RT for 30 min. The mixture was filtered off and added to 100 mg (0.14 mmol, purity about 74%) of 2-chloro-6-({(2-(4-chlorophenyl)-1,3-thiazol-4-ylmethyl}sulfanyl)-4-(4-(2-hydroxyethoxy)phenyl)pyridine-3,5-dicarbonitrile (Example 2A), and the solution was stirred at RT overnight. The mixture was then warmed to 60° C. and stirred at this temperature overnight. In a separate flask, another 87 mg (0.54 mmol) of 2,2,2-trifluoro-N-methylethanamine hydrochloride were then dissolved in 0.5 ml of DMF, 88 mg of Amberlyst A-21 were added and the mixture was stirred at RT for 30 min. The mixture was filtered off and added to the first solution. The reaction mixture obtained was stirred at 100° C. for 4.5 h. The mixture was then diluted with a little water/THF and purified by preparative HPLC (acetonitrile/water+0.1% TFA). This gave 37 mg (41% of theory) of the target compound.

$^1$H-NMR (400 MHz, DMSO-d$_6$): δ=7.94 (d, 2H), 7.71 (s, 1H), 7.58 (d, 2H), 7.54 (d, 2H), 7.11 (d, 2H), 4.78 (q, 2H), 4.70 (s, 2H), 4.09 (t, 2H), 3.93 (q, 2H), 3.74 (t, 2H), 1.26 (t, 3H).

LC-MS (Method 2): R$_t$=1.40 min; MS (ESIpos): m/z=630 (M+H)$^+$.

Example 37

2-{4-(2-(Azetidin-1-yl)-6-({(2-(4-chlorophenyl)-1,3-thiazol-4-yl)methyl}sulfanyl)-3,5-dicyanopyridin-4-yl)phenoxy}ethyl beta-alanyl-L-alaninate

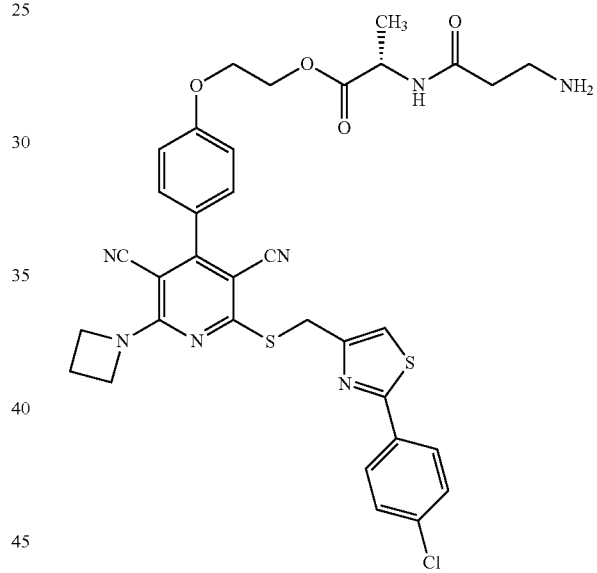

90 mg (0.113 mmol) of 2-{4-(2-(azetidin-1-yl)-6-({(2-(4-chlorophenyl)-1,3-thiazol-4-yl)methyl}sulfanyl)-3,5-dicyanopyridin-4-yl)phenoxy}ethyl N-(tert-butoxycarbonyl)-beta-alanyl-L-alaninate (Example 4A) were initially charged in 3.5 ml of dichloromethane. 0.347 ml (4.502 mmol) of trifluoroacetic acid was added, and the reaction solution was then stirred at RT overnight. The reaction solution was concentrated by evaporation and the residue was purified by preparative HPLC (acetonitrile/water+0.1% TFA). For further purification, the product was once more purified by preparative HPLC (column material: XBridge; mobile phase: acetonitrile/0.1% aq. ammonia=65/35). This gave 51 mg (65% of theory) of the target compound.

$^1$H-NMR (400 MHz, DMSO-d$_6$): δ=8.38 (d, 1H), 7.94 (d, 2H), 7.67 (s, 1H), 7.58 (d, 2H), 7.47 (d, 2H), 7.12 (d, 2H), 4.65 (s, 2H), 4.53-4.32 (m, 6H), 4.30-4.23 (m, 3H), 2.75-2.68 (m, 2H), 2.42-2.32 (m, 2H), 2.18 (t, 2H) 1.27 (d, 3H).

LC-MS (Method 1): R$_t$=2.25 min; MS (ESIpos): m/z=702 (M+H)$^+$.

Example 38

2-{4-(2-({(2-(4-Chlorophenyl)-1,3-thiazol-4-yl)methyl}sulfanyl)-3,5-dicyano-6-(propyl-amino)pyridin-4-yl)phenoxy}ethyl L-alaninate trifluoroacetate

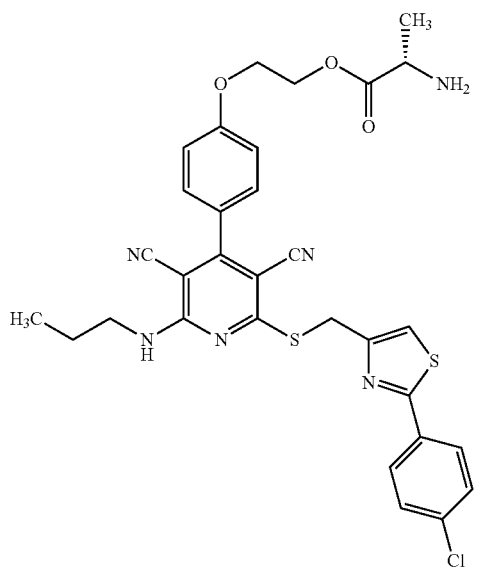 [SMILES: CCCNc1nc(SCc2csc(-c3ccc(Cl)cc3)n2)c(C#N)c(-c2ccc(OCCOC(=O)[C@H](C)N)cc2)c1C#N]

873 mg (1.191 mmol) of 2-{4-(2-({(2-(4-chlorophenyl)-1,3-thiazol-4-yl)methyl}sulfanyl)-3,5-dicyano-6-(propylamino)pyridin-4-yl)phenoxy}ethyl N-(tert-butoxycarbonyl)-L-alaninate (Example 14A) were initially charged in 29 ml of dichloromethane. 1.84 ml (23.817 mmol) of trifluoroacetic acid were added, and the reaction solution was then stirred at RT overnight. The reaction solution was concentrated by evaporation and the residue was triturated with diethyl ether. The solid formed was filtered off and dried. This gave 914 mg (89% of theory) of the target compound.

$^1$H-NMR (400 MHz, DMSO-$d_6$): δ=8.32 (br s, 2H), 8.22 (t, 1H), 7.94 (d, 2H), 7.62 (s, 1H), 7.58 (d, 2H), 7.52 (d, 2H), 7.13 (d, 2H), 4.70 (s, 2H), 4.62-4.49 (m, 2H), 4.38-4.28 (m, 2H), 4.19 (q, 1H), 3.40 (q, 2H), 1.50 (Sextett, 2H), 1.40 (d, 3H), 0.78 (t, 3H).

LC-MS (Method 4): $R_t$=1.37 min; MS (ESIpos): m/z=633 (M+H-TFA)$^+$.

Example 39

2-{4-(2-({(2-(4-Chlorophenyl)-1,3-thiazol-4-yl)methyl}sulfanyl)-3,5-dicyano-6-(methylamino)-pyridin-4-yl)phenoxy}ethyl L-alaninate trifluoroacetate

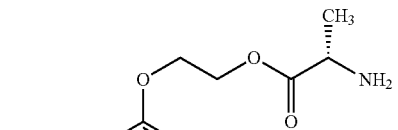
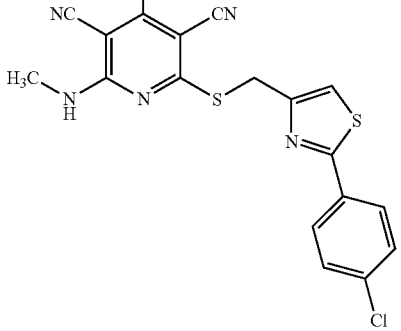

2.18 g (3.091 mmol) of 2-{4-(2-({(2-(4-chlorophenyl)-1,3-thiazol-4-yl)methyl}sulfanyl)-3,5-dicyano-6-(methylamino)pyridin-4-yl)phenoxy}ethyl N-(tert-butoxycarbonyl)-L-alaninate (Example 17A) were initially charged in 45 ml of dichloromethane. 4.76 ml (61.821 mmol) of trifluoroacetic acid were added, and the reaction solution was then stirred at RT overnight. The reaction solution was concentrated on a rotary evaporator and the residue was purified by preparative HPLC (acetonitrile/water+0.1% TFA). This gave 2.04 g (92% of theory) of the target compound.

LC-MS (Method 2): $R_t$=1.10 min; MS (ESIpos): m/z=605 (M+H-TFA)$^+$.

Example 40

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl L-alaninate trifluoroacetate

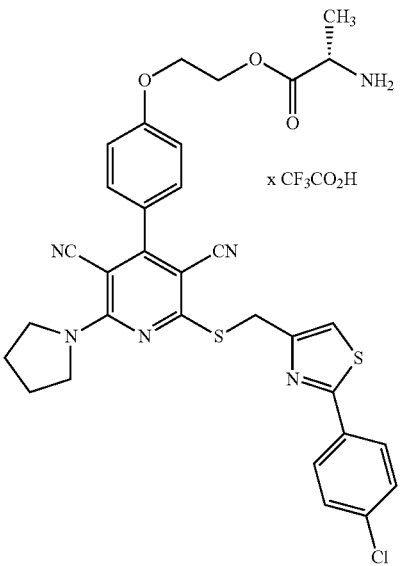 [SMILES: C[C@H](N)C(=O)OCCOc1ccc(-c2c(C#N)c(SCc3csc(-c4ccc(Cl)cc4)n3)nc(N3CCCC3)c2C#N)cc1]

250 mg (0.335 mmol) of 2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl N-(tert-butoxycarbonyl)-L-alaninate (Example 25A) were initially charged in 3.5 ml of dichloromethane. 0.258 ml (3.354 mmol) of trifluoroacetic acid was added, and the reaction solution was then stirred at RT overnight. After one day, another 0.125 ml (1.624 mmol) of trifluoroacetic acid was added to the reaction. The reaction solution was concentrated by evaporation and the residue was triturated with diethyl ether. The solid formed was filtered off. This gave 255 mg (98% of theory) of the target compound.

$^1$H-NMR (400 MHz, DMSO-$d_6$): δ=8.41-8.41 (m, 2H), 7.94 (d, 2H), 7.69 (s, 1H), 7.58 (d, 2H), 7.49 (d, 2H), 7.14 (d, 2H), 4.70 (s, 2H), 4.61-4.50 (m, 2H), 4.40-4.29 (m, 2H), 4.23-4.12 (m, 1H), 3.84 (br s, 4H), 1.95 (br s, 4H), 1.40 (d, 3H).

LC-MS (Method 4): $R_t$=1.36 min; MS (ESIpos): m/z=645 (M+H-TFA)$^+$.

Example 41

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl L-lysyl-L-alaninate dihydrochloride

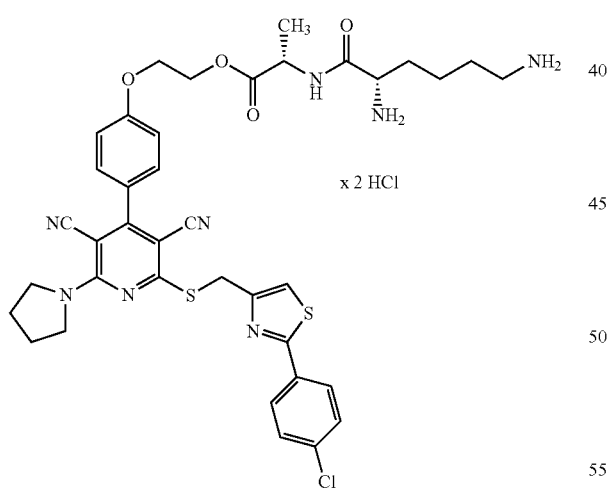

300 mg (0.308 mmol) of 2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl N$^2$,N$^6$-bis(tert-butoxycarbonyl)-L-lysyl-L-alaninate (Example 26A) were initially charged in 5.4 ml of dichloromethane. 3.08 ml (6.163 mmol) of a 1N solution of hydrogen chloride in diethyl ether were added, and the reaction solution was then stirred at RT overnight. The solid formed was filtered off, triturated with 2.5 ml of cold dichloromethane and filtered off again. This gave 250 mg (96% of theory) of the target compound.

$^1$H-NMR (400 MHz, DMSO-$d_6$): δ=8.99 (d, 1H), 8.25 (br s, 3H), 7.95 (d, 2H), 7.89 (br s, 3H), 7.70 (s, 1H). 7.58 (d, 2H), 7.50 (d, 2H), 7.13 (d, 2H), 4.70 (s, 2H), 4.52-4.35 (m, 3H), 4.33-4.26 (m, 2H), 3.85 (br s, 4H), 3.82-3.74 (m, 1H), 2.79-2.71 (m, 2H), 1.94 (br s, 4H), 1.81-1.70 (m, 2H), 1.62-1.51 (m, 2H), 1.46-1.38 (m, 2H), 1.35 (d, 3H).

LC-MS (Method 2): $R_t$=0.98 min; MS (ESIpos): m/z=773 (M+H-2HCl)$^+$.

Example 42

2-{4-(2-({(2-(4-Chlorophenyl)-1,3-thiazol-4-ylmethyl}sulfanyl)-3,5-dicyano-6-(methyl-amino)pyridin-4-yl)phenoxy}ethyl L-lysyl-L-alaninate dihydrochloride

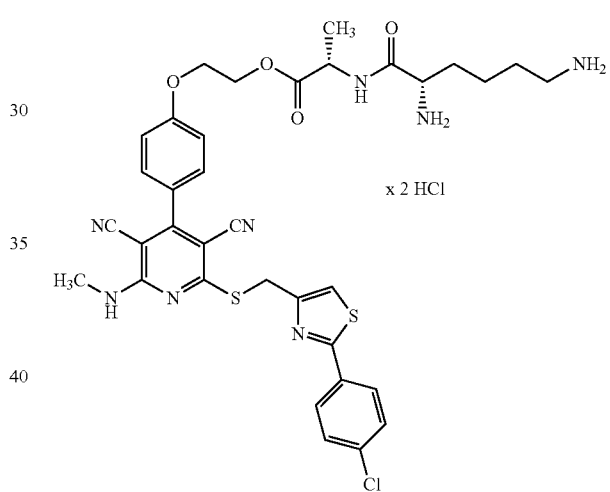

1.00 g (1.071 mmol) of 2-{4-(2-({(2-(4-chlorophenyl)-1,3-thiazol-4-ylmethyl}sulfanyl)-3,5-dicyano-6-(methylamino)pyridin-4-yl)phenoxy}ethyl N$^2$,N$^6$-bis(tert-butoxycarbonyl)-L-lysyl-L-alaninate (Example 23A) were initially charged in 18.7 ml of dichloromethane. 10.71 ml of a 1N solution of hydrogen chloride in diethyl ether were added, and the reaction solution was stirred at RT for 18 h. Another 10.71 ml of a 1N solution of hydrogen chloride in diethyl ether were then added. After a reaction time of 18 h, the reaction mixture was treated in an ultrasonic bath for 90 min. The mixture was concentrated by evaporation. This gave 867 mg (100% of theory) of the target compound.

$^1$H-NMR (400 MHz, DMSO-$d_6$): δ=8.98 (d, 1H), 8.29-8.19 (m, 2H), 8.16 (q, 1H), 7.95 (d, 2H), 7.91-7.81 (m, 2H), 7.69 (s, 1H), 7.58 (d, 2H), 7.50 (d, 2H), 7.13 (d, 2H), 4.72 (s, 2H), 4.51-4.34 (m, 3H), 4.32-4.25 (m, 2H), 3.85-3.75 (m, 1H), 3.01 (d, 3H), 2.79-2.69 (m, 2H), 1.79-1.68 (m, 2H), 1.62-1.50 (m, 2H), 1.46-1.37 (m, 2H), 1.35 (d, 3H).

LC-MS (Method 2): $R_t$=0.95 min; MS (ESIpos): m/z=733 (M+H-2HCl)$^+$.

Example 43

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl L-lysyl-beta-alaninate dihydrochloride

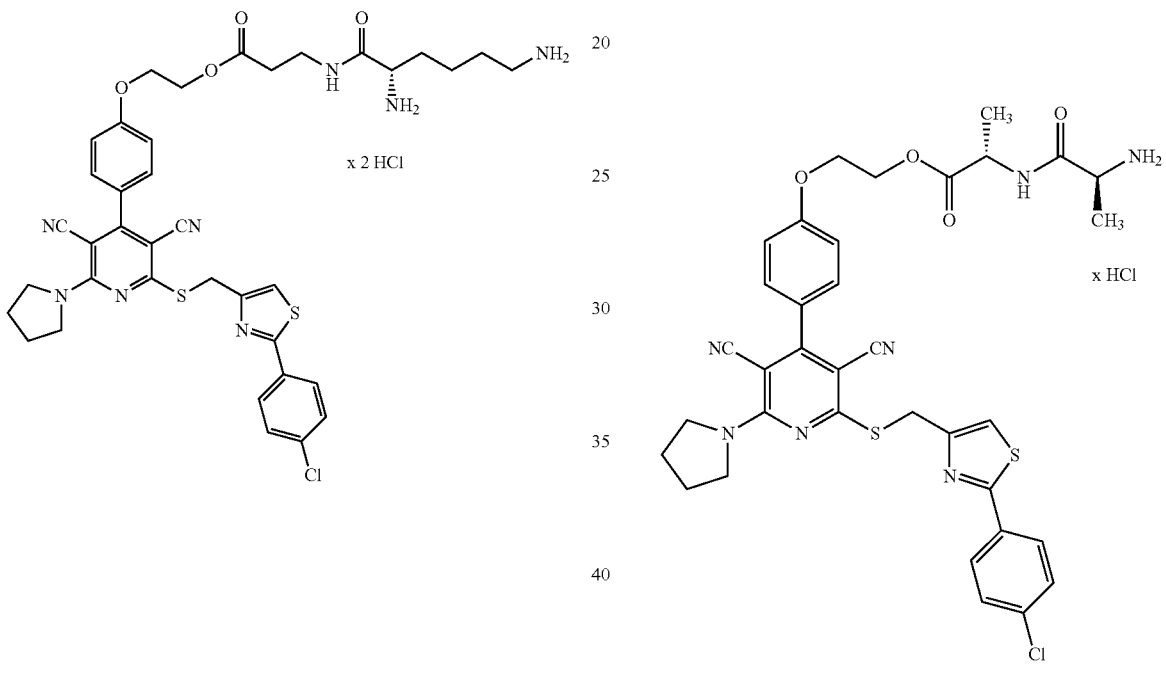

950 mg (0.976 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl N²,N⁶-bis(tert-butoxycarbonyl)-L-lysyl-beta-alaninate (Example 24A) were initially charged in 25 ml of dichloromethane. 9.76 ml of a 1N solution of hydrogen chloride in diethyl ether were added, and the reaction solution was then stirred at RT overnight. For 15 min, argon was introduced into the reaction mixture, and the mixture was then concentrated by evaporation. This gave 816 mg (99% of theory) of the target compound.

$^1$H-NMR (400 MHz, DMSO-$d_6$): δ=8.68 (t, 1H), 8.21 (br s, 3H), 7.95 (d, 2H), 7.89 (br s, 3H), 7.70 (s, 1H), 7.58 (d, 2H), 7.49 (d, 2H), 7.12 (d, 2H), 4.70 (s, 2H), 4.44-4.38 (m, 2H), 4.33-4.27 (m, 2H), 3.85 (br s, 4H), 3.79-3.65 (m, 1H), 3.49-3.28 (m, 2H), 2.79-2.71 (m, 2H), 2.60 (t, 2H), 1.95 (br s, 4H), 1.72-1.65 (m, 2H), 1.60-1.51 (m, 2H), 1.38-1.29 (m, 2H).

LC-MS (Method 2): $R_t$=1.08 min; MS (ESIpos): m/z=773 (M+H-2HCl)⁺.

Example 44

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl L-alanyl-L-alaninate hydrochloride 1.5 g (1.84 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl N-(tert-butoxycarbonyl)-L-alanyl-L-alaninate (Example 7A) were initially charged in 24 ml of dichloromethane. 18.37 ml of a 1N solution of hydrogen chloride in diethyl ether were added, and the reaction solution was then stirred at RT overnight. The solid formed was filtered off and washed with diethyl ether. This gave 1.44 g (97% of theory, purity about 94%) of the target compound.

$^1$H-NMR (400 MHz, DMSO-$d_6$): δ=8.82 (d, 1H), 8.19-8.06 (m, 2H), 7.94 (d, 2H), 7.70 (s, 1H), 7.58 (d, 2H), 7.49 (d, 2H), 7.11 (d, 2H), 4.68 (s, 2H), 4.49-4.34 (m, 3H), 4.31-4.25 (m, 2H), 3.88-3.78 (m, 5H), 1.99-1.89 (m, 4H), 1.36-1.27 (m, 6H).

LC-MS (Method 2): $R_t$=2.26 min; MS (ESIpos): m/z=716 (M+H—HCl)⁺.

Example 45

2-{4-(2-(Azetidin-1-yl)-6-({(2-(4-chlorophenyl)-1,3-thiazol-4-yl)methyl}sulfanyl)-3,5-dicyanopyridin-4-yl)phenoxy}ethyl L-alaninate trifluoroacetate

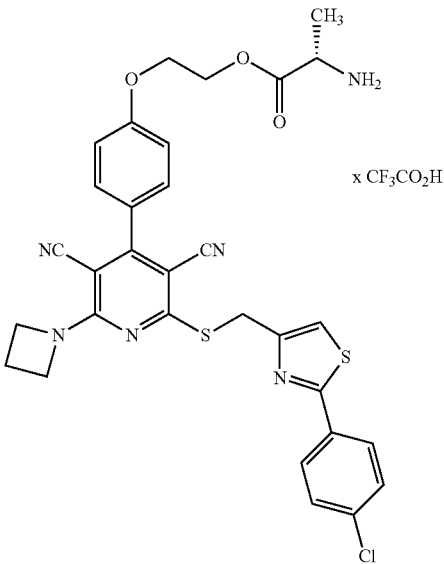 [SMILES: C[C@H](N)C(=O)OCCOc1ccc(-c2c(C#N)c(SCc3csc(-c4ccc(Cl)cc4)n3)nc(N3CCC3)c2C#N)cc1]

39 mg (0.053 mmol) of 2-{4-(2-(azetidin-1-yl)-6-({(2-(4-chlorophenyl)-1,3-thiazol-4-yl)methyl}sulfanyl)-3,5-dicyanopyridin-4-yl)phenoxy}ethyl N-(tert-butoxycarbonyl)-L-alaninate (Example 13A) were initially charged in 1.5 ml dichloromethane. 0.5 ml (6.49 mmol) of trifluoroacetic acid was added, and the reaction solution was then stirred at RT for 1.5 h. The reaction solution was concentrated by evaporation and the residue was purified by preparative HPLC (acetonitrile/water+0.1% TFA). This gave 40 mg (100% of theory) of the target compound.

$^1$H-NMR (400 MHz, DMSO-$d_6$): δ=8.37-8.26 (m, 2H), 7.95 (d, 2H), 7.67 (s, 1H), 7.58 (d, 2H), 7.48 (d, 2H), 7.13 (d, 2H), 4.65 (s, 2H), 4.60-4.42 (m, 6H), 4.37-4.31 (m, 2H), 4.22-4.12 (m, 1H), 2.44-2.31 (m, 2H), 1.39 (d, 3H).

LC-MS (Method 1): $R_t$=2.26 min; MS (ESIpos): m/z=631 (M+H-TFA)$^+$.

Example 46

2-{4-(2-(Azetidin-1-yl)-6-({(2-(4-chlorophenyl)-1,3-thiazol-4-ylmethyl}sulfanyl)-3,5-dicyanopyridin-4-yl)phenoxy}ethyl L-lysyl-L-alaninate bis(trifluoroacetate)

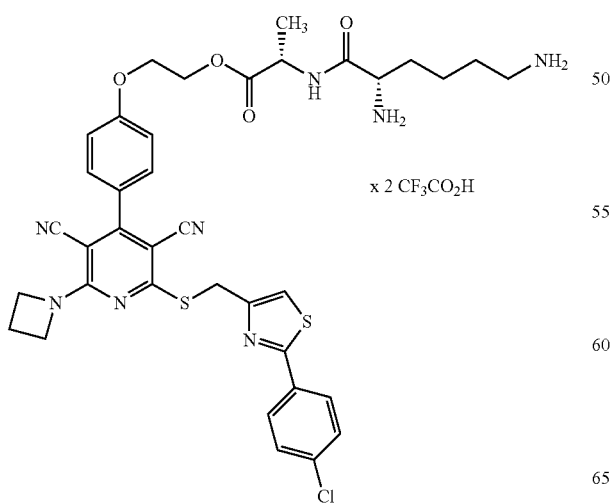

180 mg (0.188 mmol) of 2-{4-(2-(azetidin-1-yl)-6-({(2-(4-chlorophenyl)-1,3-thiazol-4-yl)methyl}sulfanyl)-3,5-dicyanopyridin-4-yl)phenoxy}ethyl $N^2,N^6$-bis(tert-butoxycarbonyl)-L-lysyl-L-alaninate (Example 3A) were initially charged in 5 ml dichloromethane. 1.0 ml (12.98 mmol) of trifluoroacetic acid was added, and the reaction solution was then stirred at RT for 30 min. The reaction solution was concentrated by evaporation and the residue was purified by preparative HPLC (acetonitrile/water+0.1% TFA). This gave 153 mg (83% of theory) of the target compound.

$^1$H-NMR (400 MHz, DMSO-$d_6$): δ=8.88 (d, 1H), 8.27-8.10 (m, 2H), 7.95 (d, 2H), 7.82-7.69 (m, 2H), 7.67 (s, 1H), 7.58 (d, 2H), 7.47 (d, 2H), 7.12 (d, 2H), 4.66 (s, 2H), 4.54-4.35 (m, 7H), 4.32-4.26 (m, 2H), 3.82-3.71 (m, 1H), 2.80-2.69 (m, 2H), 2.43-2.31 (m, 2H), 1.77-1.64 (m, 2H), 1.59-1.47 (m, 2H), 1.43-1.36 (m, 2H), 1.34 (d, 3H).

LC-MS (Method 6): $R_t$=1.67 min; MS (ESIpos): m/z=759 (M+H-2TFA)$^+$.

Example 47

2-{4-(2-({(2-(4-Chlorophenyl)-1,3-thiazol-4-ylmethyl}sulfanyl)-3,5-dicyano-6-(propyl-amino)pyridin-4-yl)phenoxy}ethyl L-ornithinate bis(trifluoroacetate)

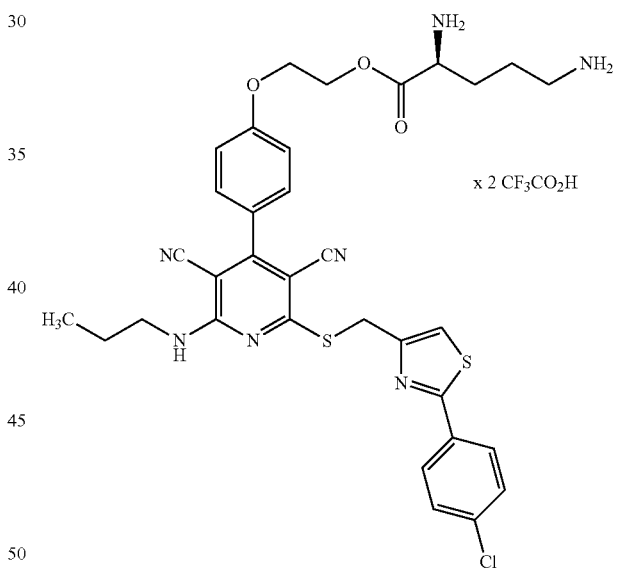

60 mg (0.068 mmol) of 2-{4-(2-({(2-(4-chlorophenyl)-1,3-thiazol-4-ylmethyl}sulfanyl)-3,5-dicyano-6-(propylamino)pyridin-4-yl)phenoxy}ethyl $N^2,N^5$-bis(tert-butoxycarbonyl)-L-ornithinate (Example 20A) were initially charged in 1.8 ml dichloromethane. 0.211 ml (2.738 mmol) of trifluoroacetic acid was added, and the reaction solution was then stirred at RT overnight. The reaction solution was concentrated by evaporation and the residue was purified by preparative HPLC (acetonitrile/water+0.1% TFA). This gave 55 mg (89% of theory) of the target compound.

$^1$H-NMR (400 MHz, DMSO-$d_6$): δ=8.46-8.38 (m, 2H), 8.26-8.20 (t, 1H), 7.94 (d, 2H), 7.78-7.67 (m, 2H), 7.64 (s, 1H), 7.58 (d, 2H), 7.53 (d, 2H), 7.15 (d, 2H), 4.70 (s, 2H), 4.63-4.50 (m, 2H), 4.38-4.32 (m, 2H), 4.21-4.13 (m, 1H), 3.46-3.37 (m, 2H), 2.85-2.77 (m, 2H), 1.96-1.56 (m, 4H), 1.55-1.46 (m, 2H), 0.79 (t, 3H).

LC-MS (Method 1): $R_t$=1.98 min; MS (ESIpos): m/z=676 (M+H-2TFA)$^+$.

Example 48

2-{4-(2-(Azetidin-1-yl)-6-({(2-(4-chlorophenyl)-1,3-thiazol-4-ylmethyl}sulfanyl)-3,5-dicyanopyridin-4-yl)phenoxy}ethyl L-ornithinate bis(trifluoroacetate)

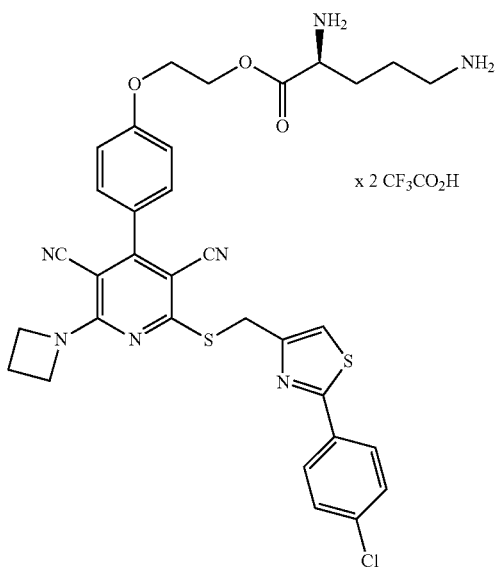 [SMILES: N#Cc1c(SCc2csc(-c3ccc(Cl)cc3)n2)nc(N2CCC2)c(C#N)c1-c1ccc(OCCOC(=O)[C@@H](N)CCCN)cc1]

The preparation was carried out as described in Example 47 using the appropriate starting materials.

Yield: 71% of theory $^1$H-NMR (400 MHz, DMSO-$d_6$): δ=8.55-8.38 (m, 2H), 7.94 (d, 2H), 7.84-7.69 (m, 2H), 7.67 (s, 1H), 7.58 (d, 2H), 7.49 (d, 2H), 7.13 (d, 2H), 4.67 (s, 2H), 4.62-4.51 (m, 2H), 4.50-4.41 (m, 4H), 4.37-4.31 (m, 2H), 4.21-4.12 (m, 1H), 2.85-2.75 (m, 2H), 2.44-2.35 (m, 2H), 1.92-1.53 (m, 4H).

LC-MS (Method 1): $R_t$=1.93 min; MS (ESIpos): m/z=674 (M+H-2TFA)$^+$.

Example 49

2-{4-(2-(Azetidin-1-yl)-6-({(2-(4-chlorophenyl)-1,3-thiazol-4-yl)methyl}sulfanyl)-3,5-dicyanopyridin-4-yl)phenoxy}ethyl beta-alaninate trifluoroacetate

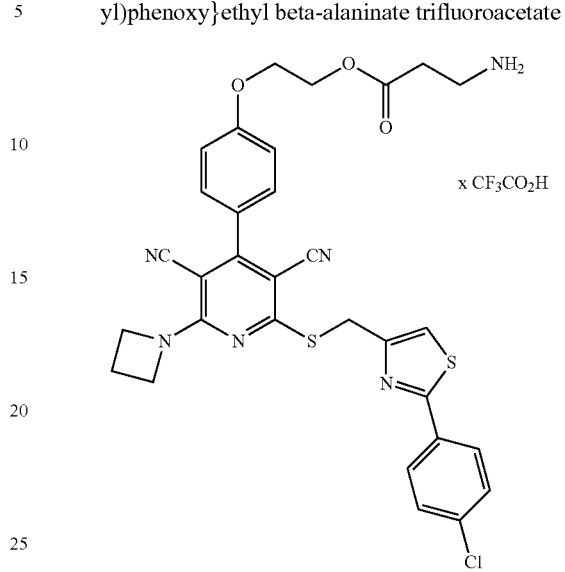

The preparation was carried out as described in Example 47 using the appropriate starting materials.

Yield: 54% of theory $^1$H-NMR (400 MHz, DMSO-$d_6$): δ=7.95 (d, 2H), 7.80-7.58 (m, 2H), 7.67 (s, 1H), 7.58 (d, 2H), 7.47 (d, 2H), 7.13 (d, 2H), 4.66 (s, 2H), 4.53-4.40 (m, 6H), 4.34-4.27 (m, 2H), 3.10-2.99 (m, 2H), 2.74-2.66 (m, 2H), 2.44-2.31 (m, 2H).

LC-MS (Method 1): $R_t$=2.23 min; MS (ESIpos): m/z=631 (M+H-TFA)$^+$.

Example 50

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl beta-alaninate trifluoroacetate

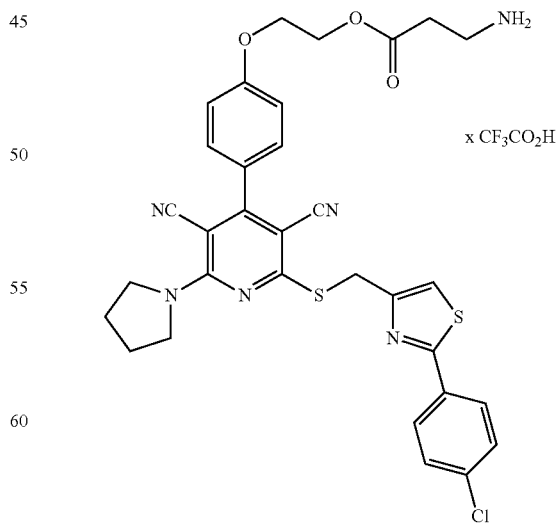

The preparation was carried out as described in Example 47 using the appropriate starting materials.

Yield: 63% of theory

¹H-NMR (400 MHz, DMSO-d₆): δ=7.94 (d, 2H), 7.80-7.68 (br s, 2H), 7.70 (s, 1H), 7.58 (d, 2H), 7.49 (d, 2H), 7.14 (d, 2H), 4.70 (s, 2H), 4.47-4.41 (m, 2H), 4.34-4.28 (m, 2H), 3.87-3.80 (m, 4H), 3.09-3.01 (m, 2H), 2.74-2.67 (m, 2H), 1.99-1.91 (m, 4H).

LC-MS (Method 1): R$_t$=2.31 min; MS (ESIpos): m/z=645 (M+H-TFA)⁺.

Example 51

2-{4-(2-({(2-(4-Chlorophenyl)-1,3-thiazol-4-yl)methyl}sulfanyl)-3,5-dicyano-6-(propylamino)pyridin-4-yl)phenoxy}ethyl L-alanyl-L-alaninate trifluoroacetate

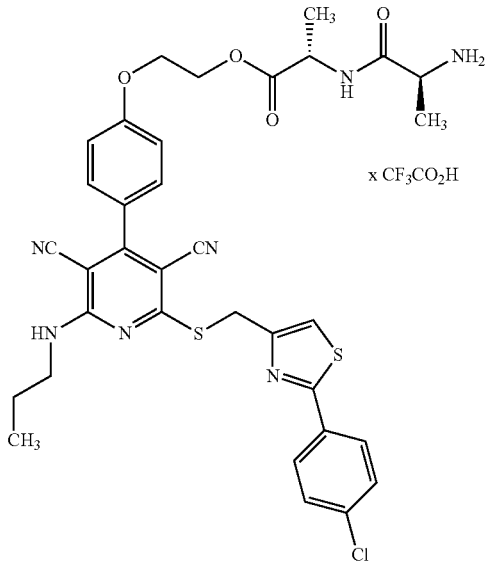 [SMILES: CCCNc1nc(SCc2csc(-c3ccc(Cl)cc3)n2)c(C#N)c(-c2ccc(OCCOC(=O)[C@H](C)NC(=O)[C@H](C)N)cc2)c1C#N]

The preparation was carried out as described in Example 47 using the appropriate starting materials. 20 equivalents of trifluoroacetic acid were used.

Yield: 44% of theory

¹H-NMR (400 MHz, DMSO-d₆): δ=8.78 (d, 1H), 8.22 (t, 1H), 8.12-8.02 (m, 2H), 7.95 (d, 2H), 7.65 (s, 1H), 7.58 (d, 2H), 7.51 (d, 2H), 7.13 (d, 2H), 4.70 (s, 2H), 4.49-4.35 (m, 3H), 4.31-4.26 (m, 2H), 3.87-3.80 (m, 1H), 3.40 (q, 2H), 1.56-1.45 (m, 2H), 1.34 (dd, 6H), 0.78 (t, 3H).

LC-MS (Method 1): R$_t$=2.31 min; MS (ESIpos): m/z=704 (M+H-TFA)⁺.

Example 52

2-{4-(2-({(2-(4-Chlorophenyl)-1,3-thiazol-4-yl)methyl}sulfanyl)-3,5-dicyano-6-(methylamino)pyridin-4-yl)phenoxy}ethyl L-ornithinate bis(trifluoroacetate)

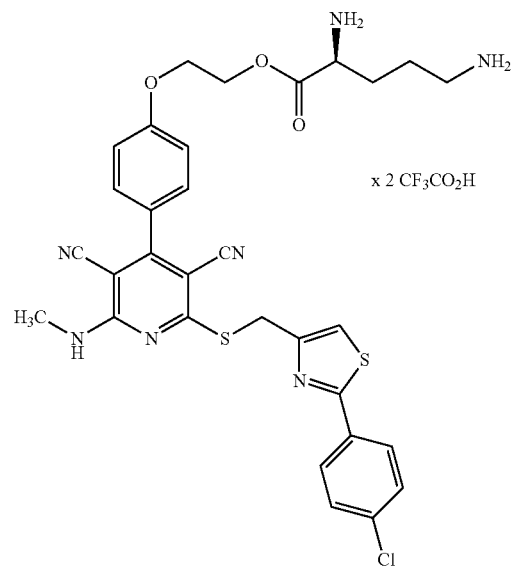 [SMILES: CNc1nc(SCc2csc(-c3ccc(Cl)cc3)n2)c(C#N)c(-c2ccc(OCCOC(=O)[C@@H](N)CCCN)cc2)c1C#N]

The preparation was carried out as described in Example 47 using the appropriate starting materials.

Yield: 87% of theory

¹H-NMR (400 MHz, DMSO-d₆): δ=8.51-8.39 (m, 2H), 8.17 (q, 1H), 7.94 (d, 2H), 7.84-7.72 (m, 2H), 7.68 (s, 1H), 7.59 (d, 2H), 7.51 (d, 2H), 7.15 (d, 2H), 4.73 (s, 2H), 4.62-4.49 (m, 2H), 4.38-4.31 (m, 2H), 4.21-4.14 (m, 1H), 3.03 (d, 3H), 2.85-2.76 (m, 2H), 1.95-1.55 (m, 4H).

LC-MS (Method 1): R$_t$=1.84 min; MS (ESIpos): m/z=648 (M+H-2TFA)⁺.

Example 53

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl L-alanyl-beta-alaninate trifluoroacetate

Example 54

2-{4-(2-({(2-(4-Chlorophenyl)-1,3-thiazol-4-yl)methyl}sulfanyl)-3,5-dicyano-6-(propylamino)pyridin-4-yl)phenoxy}ethyl L-lysyl-L-alaninate bis(trifluoroacetate)

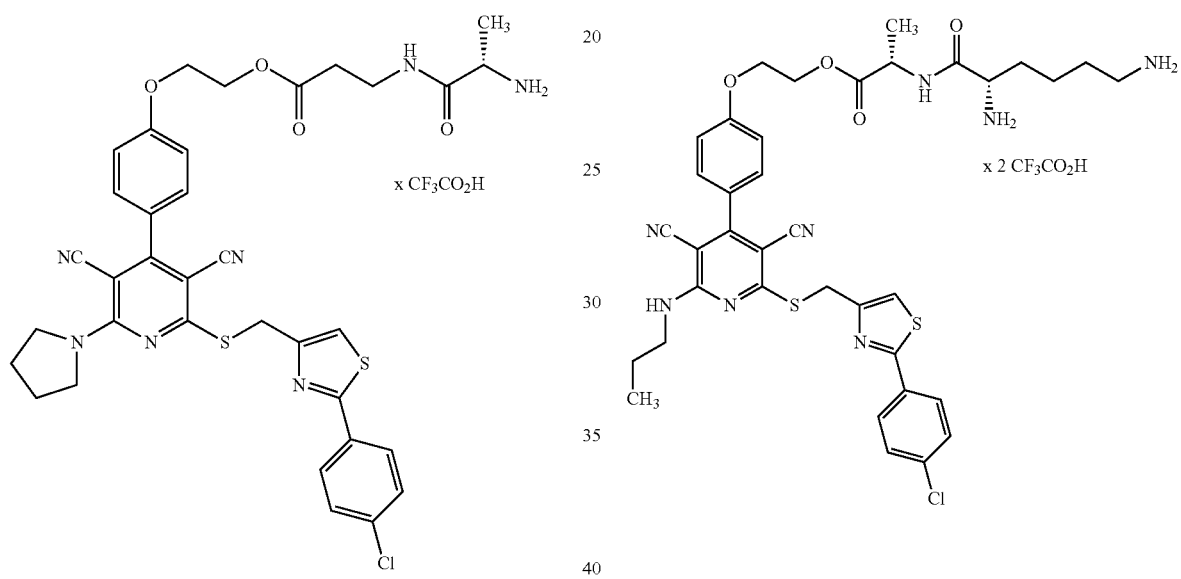

The preparation was carried out as described in Example 47 using the appropriate starting materials.

Yield: 88% of theory $^1$H-NMR (400 MHz, DMSO-d$_6$): δ=8.47 (t, 1H), 8.09-7.99 (m, 2H), 7.95 (d, 2H), 7.69 (s, 1H), 7.58 (d, 2H), 7.50 (d, 2H), 7.13 (d, 2H), 4.70 (s, 2H), 4.44-4.37 (m, 2H), 4.32-4.25 (m, 2H), 4.11-4.04 (m, 1H), 3.85 (br s, 4H) 3.47-3.28 (m, 2H), 2.59-2.54 (m, 2H), 1.95 (br s, 4H), 1.30 (d, 3H).

LC-MS (Method 1): R$_t$=2.31 min; MS (ESIpos): m/z=716 (M+H-TFA)$^+$.

The preparation was carried out as described in Example 47 using the appropriate starting materials. 20 equivalents of trifluoroacetic acid were used.

Yield: 26% of theory $^1$H-NMR (400 MHz, DMSO-d$_6$): δ=8.88 (d, 1H), 8.23 (t, 1H), 8.16-8.11 (m, 2H), 7.94 (d, 2H), 7.75-7.60 (m, 2H), 7.64 (s, 1H), 7.58 (d, 2H), 7.51 (d, 2H), 7.10 (d, 2H), 4.69 (s, 2H), 4.54-4.35 (m, 3H), 4.33-4.23 (m, 2H), 3.78-3.75 (m, 1H), 3.41 (q, 2H), 2.80-2.71 (m, 2H), 1.73 (q, 2H), 1.59-1.44 (m, 4H), 1.43-1.31 (m, 2H), 1.35 (d, 3H), 0.79 (t, 3H).

LC-MS (Method 4): R$_t$=1.19 min; MS (ESIpos): m/z=761 (M+H-2TFA)$^+$.

Example 55

2-{4-(2-({(2-(4-Chlorophenyl)-1,3-thiazol-4-yl)methyl}sulfanyl)-3,5-dicyano-6-(propylamino)pyridin-4-yl)phenoxy}ethyl beta-alanyl-L-alaninate trifluoroacetate

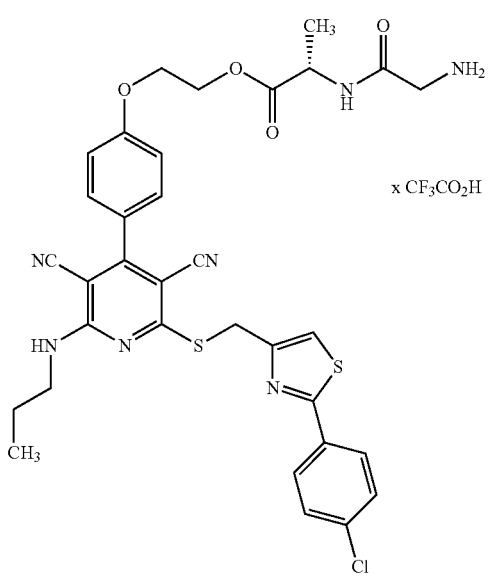 [SMILES: CCCNc1nc(SCc2csc(-c3ccc(Cl)cc3)n2)c(C#N)c(-c2ccc(OCCOC(=O)[C@H](C)NC(=O)CN)cc2)c1C#N]

Example 56

2-{4-(2-({(2-(4-Chlorophenyl)-1,3-thiazol-4-yl)methyl}sulfanyl)-3,5-dicyano-6-(methyl-amino)pyridin-4-yl)phenoxy}ethyl beta-alaninate trifluoroacetate

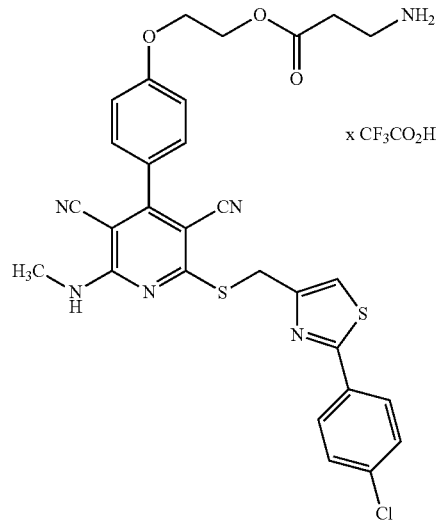 [SMILES: CNc1nc(SCc2csc(-c3ccc(Cl)cc3)n2)c(C#N)c(-c2ccc(OCCOC(=O)CCN)cc2)c1C#N]

The preparation was carried out as described in Example 47 using the appropriate starting materials. 20 equivalents of trifluoroacetic acid were used.

Yield: 87% of theory $^1$H-NMR (400 MHz, DMSO-d$_6$): δ=8.58 (d, 1H), 8.21 (t, 1H), 7.94 (d, 2H), 7.75-7.62 (m, 2H), 7.65 (s, 1H), 7.58 (d, 2H), 7.50 (d, 2H), 7.13 (d, 2H), 4.69 (s, 2H), 4.51-4.23 (m, 5H), 3.40 (q, 2H), 3.02-2.93 (m, 2H), 2.58-2.48 (m, 2H), 1.58-1.42 (m, 2H), 1.29 (d, 3H), 0.79 (t, 3H).

LC-MS (Method 2): R$_t$=1.19 min; MS (ESIpos): m/z=704 (M+H-TFA)$^+$.

The preparation was carried out as described in Example 47 using the appropriate starting materials.

Yield: 91% of theory $^1$H-NMR (400 MHz, DMSO-d$_6$): δ=8.16 (q, 1H), 7.94 (d, 2H), 7.79-7.67 (m, 2H), 7.69 (s, 1H), 7.58 (d, 2H), 7.50 (d, 2H), 7.14 (d, 2H), 4.73 (s, 2H), 4.47-4.41 (m, 2H), 4.34-4.28 (m, 2H), 3.11-2.99 (m, 2H), 3.02 (d, 3H), 2.74-2.65 (m, 2H).

LC-MS (Method 4): R$_t$=1.28 min; MS (ESIpos): m/z=605 (M+H-TFA)$^+$.

Example 57

2-{4-(2-({(2-(4-Chlorophenyl)-1,3-thiazol-4-yl)methyl}sulfanyl)-3,5-dicyano-6-(methylamino)pyridin-4-yl)phenoxy}ethyl L-alanyl-L-alaninate trifluoroacetate

Example 58

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl L-ornithyl-L-alaninate bis(trifluoroacetate)

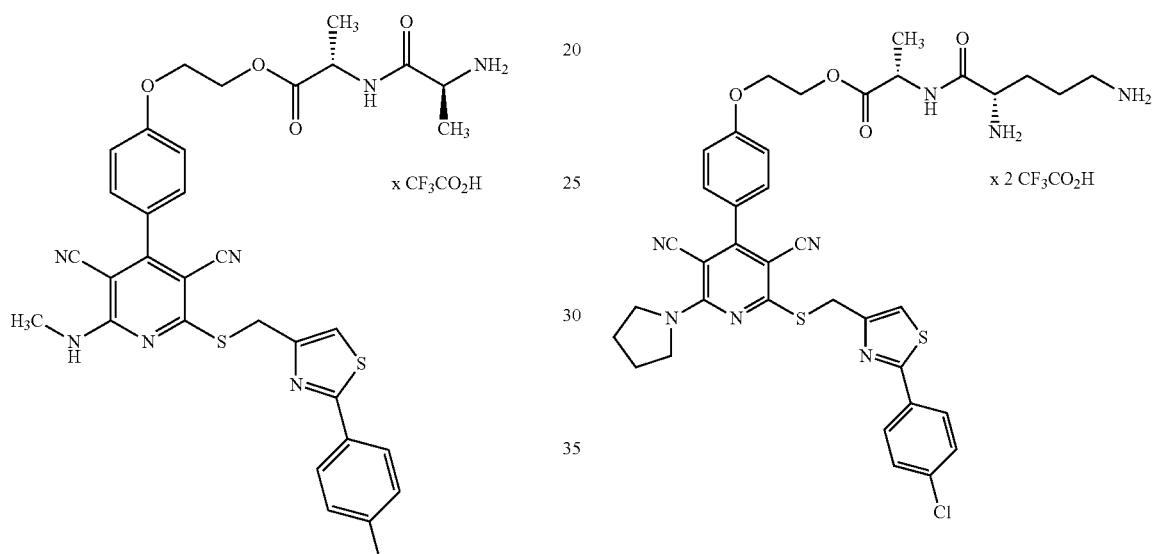

The preparation was carried out as described in Example 47 using the appropriate starting materials. 20 equivalents of trifluoroacetic acid were used.

Yield: 90% of theory $^1$H-NMR (400 MHz, DMSO-$d_6$): δ=8.79 (d, 1H), 8.16 (q, 1H), 8.10-8.02 (m, 2H), 7.95 (d, 2H), 7.69 (s, 1H), 7.58 (d, 2H), 7.50 (d, 2H), 7.13 (d, 2H), 4.73 (s, 2H), 4.49-4.35 (m, 3H), 4.31-4.25 (m, 2H), 3.86-3.79 (m, 1H), 3.01 (d, 3H), 1.34 (d, 6H).

LC-MS (Method 2): $R_t$=1.12 min; MS (ESIpos): m/z=676 (M+H-TFA)$^+$.

The preparation was carried out as described in Example 47 using the appropriate starting materials. 20 equivalents of trifluoroacetic acid were used.

Yield: 60% of theory $^1$H-NMR (400 MHz, DMSO-$d_6$): δ=8.90 (d, 1H), 8.25-8.17 (m, 2H), 7.94 (d, 2H), 7.82-7.71 (m, 2H), 7.70 (s, 1H), 7.58 (d, 2H), 7.50 (d, 2H), 7.12 (d, 2H), 4.70 (s, 2H), 4.53-4.35 (m, 3H), 4.32-4.28 (m, 2H), 3.88-3.76 (m, 5H), 2.85-2.74 (m, 2H), 1.95 (br s, 4H), 1.81-1.69 (m, 2H), 1.67-1.57 (m, 2H), 1.36 (d, 3H).

LC-MS (Method 2): $R_t$=1.09 min; MS (ESIpos): m/z=759 (M+H-2TFA)$^+$.

Example 59

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl L-ornithinate bis(trifluoroacetate)

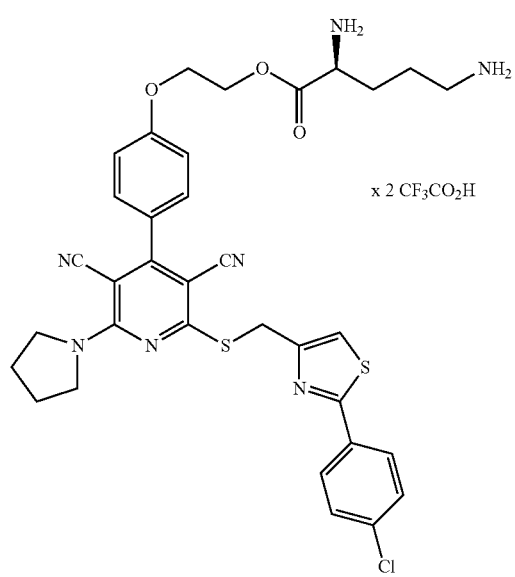 [SMILES: N#Cc1c(SCc2csc(-c3ccc(Cl)cc3)n2)nc(N2CCCC2)c(C#N)c1-c1ccc(OCCOC(=O)[C@@H](N)CCCN)cc1]

The preparation was carried out as described in Example 47 using the appropriate starting materials. 20 equivalents of trifluoroacetic acid were used.

Yield: 72% of theory $^1$H-NMR (400 MHz, DMSO-d$_6$): δ=8.54-8.39 (m, 2H), 7.94 (d, 2H), 7.83-7.71 (m, 2H), 7.70 (s, 1H), 7.59 (d, 2H), 7.51 (d, 2H), 7.14 (d, 2H), 4.70 (s, 2H), 4.64-4.50 (m, 2H), 4.38-4.32 (m, 2H), 4.21-4.13 (m, 1H), 3.84 (br s, 4H), 2.85-2.76 (m, 2H), 1.95 (br s, 4H), 1.90-1.55 (m, 4H).

LC-MS (Method 1): R$_t$=1.93 min; MS (ESIpos): m/z=688 (M+H-2TFA)$^+$.

Example 60

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl beta-alanyl-L-alaninate trifluoroacetate

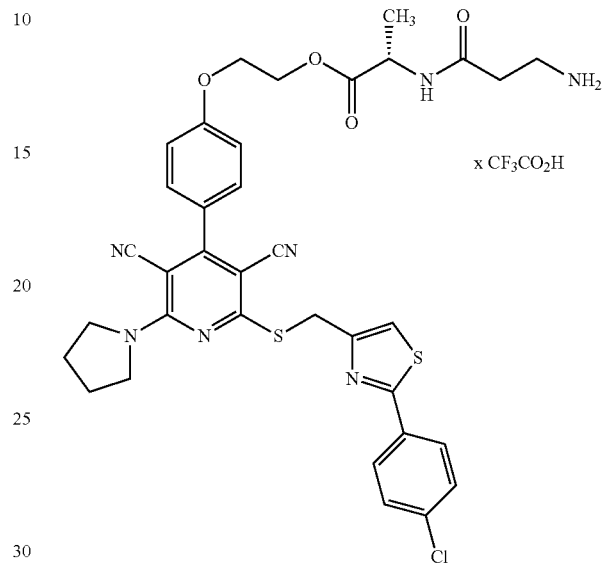

The preparation was carried out as described in Example 47 using the appropriate starting materials.

Yield: 69% of theory $^1$H-NMR (400 MHz, DMSO-d$_6$): δ=8.57 (d, 1H), 7.95 (d, 2H), 7.70 (s, 1H), 7.68-7.61 (m, 2H), 7.58 (d, 2H), 7.49 (d, 2H), 7.12 (d, 2H), 4.70 (s, 2H), 4.50-4.24 (m, 5H), 3.84 (br s, 4H), 3.03-2.92 (m, 2H), 2.51-2.48 (m, 2H), 2.00-1.90 (m, 4H), 1.31 (d, 3H).

LC-MS (Method 4): R$_t$=1.38 min; MS (ESIpos): m/z=716 (M+H-TFA)$^+$.

Example 61

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl beta-alanyl-L-alaninate hydrochloride

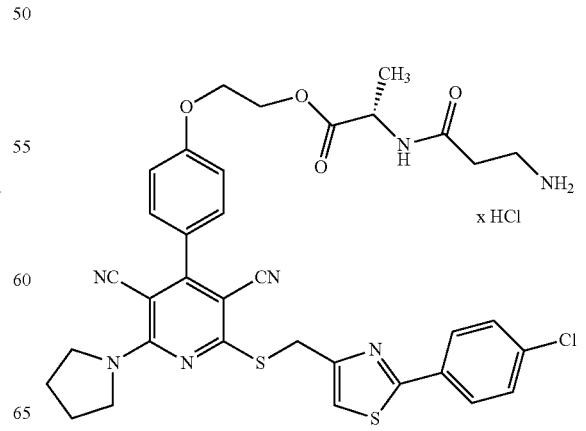

200 mg (0.245 mmol) of 2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl N-(tert-butoxycarbonyl)-beta-alanyl-L-alaninate (Example 8A) were dissolved in 2 ml dichloromethane, and 2.45 ml 1M HCl in diethyl ether were added. After 3 hours, 1 ml of a 1N solution of hydrogen chloride in diethyl ether was added and the mixture was stirred at room temperature for a further 2 hours. The precipitated solid was filtered off with suction, washed with diethyl ether and dried under reduced pressure. 155 mg (yield: 82% of theory) of the target compound were obtained.

$^1$H-NMR (400 MHz, DMSO-d$_6$): δ=8.60 (d, 1H), 7.95 (d, 2H), 7.79 (m br, 3H), 7.70 (s, 1H), 7.58 (d, 2H), 7.49 (d, 2H), 7.13 (d, 2H), 4.70 (s, 2H), 4.48-4.27 (m, 6H), 3.99 (m, 1H), 3.83 (m, 4H), 2.96 (m, 2H), 1.94 (m, 4H), 1.29 (d, 3H).

LC-MS (Method 1): R$_t$=2.30 min; MS (ESIpos): m/z=716 (M+H—HCl)$^+$.

Example 62

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl L-prolyl-L-alaninate hydrochloride

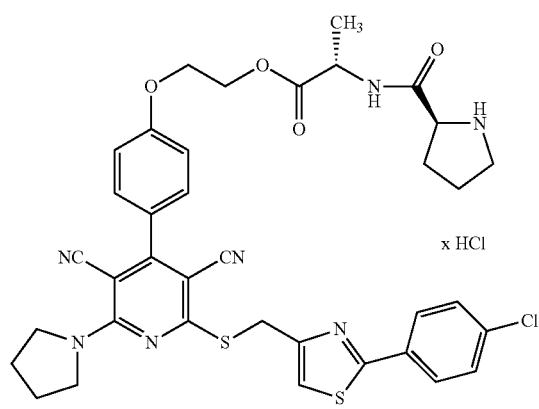 [SMILES: C[C@H](NC(=O)[C@@H]1CCCN1)C(=O)OCCOc1ccc(-c2c(C#N)c(SCc3csc(-c4ccc(Cl)cc4)n3)nc(N3CCCC3)c2C#N)cc1]

495 mg (0.588 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl 1-(tert-butoxycarbonyl)-L-prolyl-L-alaninate were dissolved in 3 ml dichloromethane, and 5.876 ml of a 1N solution of hydrogen chloride in diethyl ether were added. After 6 hours of stirring, the precipitated solid was filtered off with suction, washed with diethyl ether and dried under reduced pressure. 410 mg (90% of theory) of the target compound were obtained.

$^1$H-NMR (400 MHz, DMSO-d$_6$): δ=9.56 (m, 1H), 8.97 (d, 1H), 8.53 (m, 1H), 7.94 (d, 2H), 7.70 (s, 1H), 7.58 (d, 2H), 7.49 (d, 2H), 7.12 (d, 2H), 4.70 (s, 2H), 4.46 (m, 1H), 4.40 (m, 2H), 4.27 (m, 2H), 4.16 (m, 1H), 3.91 (m, 4H), 3.14 (m, 2H), 2.28 (m, 1H), 1.94 (m, 4H), 1.86-1.67 (m, 3H), 1.35 (d, 3H).

LC-MS (Method 4): R$_t$=1.35 min; MS (ESIpos): m/z=742 (M+H—HCl)$^+$.

Example 63

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl L-isoleucyl-L-alaninate hydrochloride

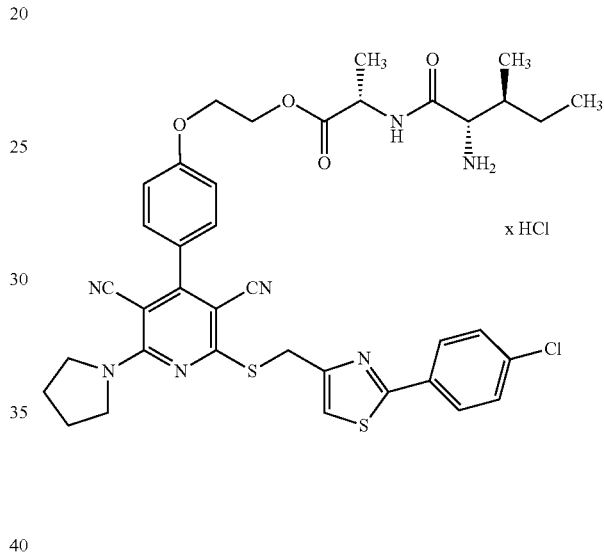

414 mg (0.482 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl N-(tert-butoxycarbonyl)-L-isoleucyl-L-alaninate were dissolved in 3 ml dichloromethane, and 4.822 ml of a 1N solution of hydrogen chloride in diethyl ether were added. After 6 hours of stirring, 2 ml of a 1N solution of hydrogen chloride in diethyl ether were added, and the mixture was stirred at room temperature for a further 24 hours. The precipitated solid was filtered off with suction, washed with diethyl ether and dried under reduced pressure. Since the reaction was still incomplete, the solid was stirred in 5 ml of a 1N solution of hydrogen chloride in diethyl ether for a further 24 h. The precipitated solid was filtered off with suction, washed with diethyl ether and dried under reduced pressure. 312 mg (81% of theory) of the target compound were obtained.

$^1$H-NMR (400 MHz, DMSO-d$_6$): δ=8.83 (d, 1H), 8.20-8.09 (m, 3H), 7.94 (d, 2H), 7.70 (s, 1H), 7.58 (d, 2H), 7.49 (d, 2H), 7.11 (d, 2H), 4.70 (s, 2H), 4.49-4.39 (m, 3H), 4.27 (m, 2H), 3.83 (m, 4H), 3.60 (m, 1H), 1.94 (m, 4H), 1.80 (m, 1H), 1.52 (m, 1H), 1.34 (d, 3H), 1.22-1.07 (m, 1H), 0.91 (d, 3H), 0.83 (t, 3H).

LC-MS (Method 2): R$_t$=1.19 min; MS (ESIpos): m/z=758 (M+H—HCl)$^+$.

Example 64

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl N-((2S)-2,4-diaminobutanoyl)-L-alaninate dihydrochloride

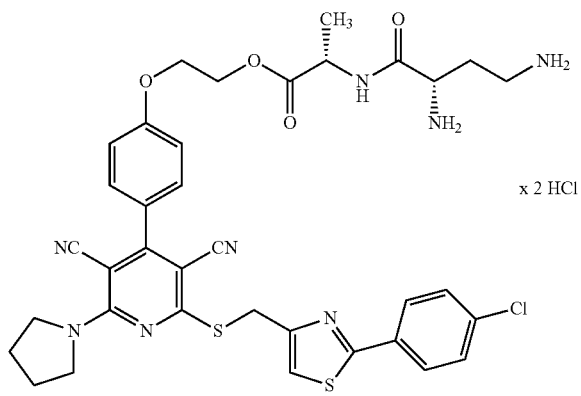 [SMILES: C[C@H](NC(=O)[C@@H](N)CCN)C(=O)OCCOc1ccc(-c2c(C#N)c(SCc3csc(-c4ccc(Cl)cc4)n3)nc(N3CCCC3)c2C#N)cc1]

420 mg (0.444 mmol) of 2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl N-{(2S)-2,4-bis((tert-butoxycarbonyl)-amino)butanoyl}-L-alaninate were dissolved in 5 ml dichloromethane, and 4.442 ml of a 1N solution of hydrogen chloride in diethyl ether were added. After 4 hours of stirring, the precipitated solid was filtered off with suction, washed with diethyl ether and dried under reduced pressure. 322 mg (88% of theory) of the target compound were obtained.

$^1$H-NMR (400 MHz, DMSO-$d_6$): δ=9.36 (d, 1H), 8.45 (m, 3H), 8.21 (m, 3H), 7.94 (d, 2H), 7.70 (s, 1H), 7.58 (d, 2H), 7.50 (d, 2H), 7.14 (d, 2H), 4.70 (s, 2H), 4.52-4.34 (m, 5H), 4.05 (m, 1H), 3.83 (m, 4H), 3.01 (m, 2H), 2.16-1.99 (m, 2H), 1.94 (m, 4H), 1.37 (d, 3H).

LC-MS (Method 4): $R_t$=1.15 min; MS (ESIpos): m/z=745 (M+H-2HCl)$^+$.

Example 65

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl L-histidyl-L-alaninate dihydrochloride

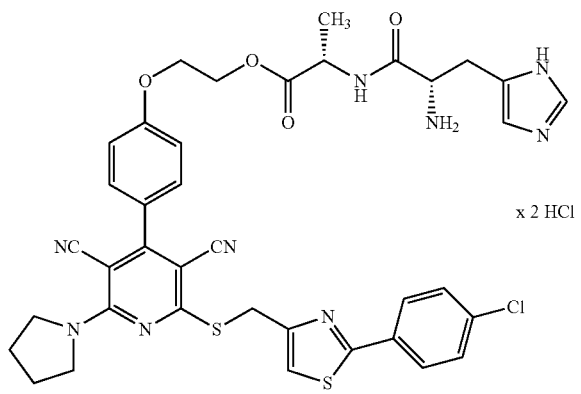 [SMILES: C[C@H](NC(=O)[C@@H](N)Cc1cnc[nH]1)C(=O)OCCOc1ccc(-c2c(C#N)c(SCc3csc(-c4ccc(Cl)cc4)n3)nc(N3CCCC3)c2C#N)cc1]

169 mg (0.192 mmol) of 2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl N-(tert-butoxycarbonyl)-L-histidyl-L-alaninate were dissolved in 3 ml dichloromethane, and 1.915 ml of a 1N solution of hydrogen chloride in diethyl ether were added. After 6 hours of stirring, the precipitated solid was filtered off with suction, washed with diethyl ether and dried under reduced pressure. 75 mg (44% of theory) of the target compound were obtained.

$^1$H-NMR (400 MHz, DMSO-$d_6$): δ=14.73-14.30 (m, 2H), 9.22 (d, 1H), 9.07 (s, 1H), 8.54 (m, 3H), 7.94 (d, 2H), 7.70 (s, 1H), 7.58 (d, 2H), 7.47 (m, 3H), 7.12 (d, 2H), 4.70 (s, 2H), 4.50-4.34 (m, 3H), 4.29 (m, 3H), 3.63 (m, 4H), 3.34-3.14 (m, 2H), 1.94 (m, 4H), 1.35 (d, 3H).

LC-MS (Method 4): $R_t$=1.18 min; MS (ESIpos): m/z=782 (M+H-2HCl)$^+$.

Example 66

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl L-argyl-L-alaninate dihydrochloride

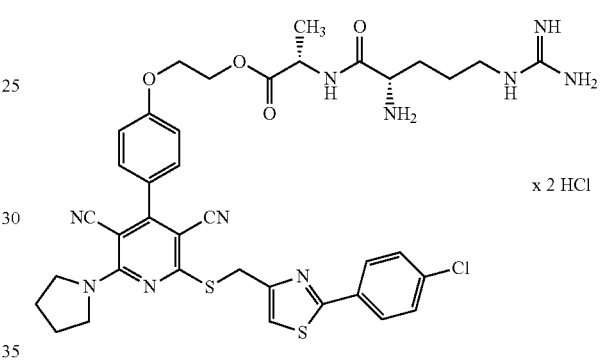

341 mg (0.310 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl $N^5$—(N,N'-bis(tert-butoxycarbonyl)carbamimidoyl)-$N^2$-(tert-butoxycarbonyl)-L-ornithyl-L-alaninate were dissolved in 5 ml dichloromethane, and 3.095 ml of a 1N solution of hydrogen chloride in diethyl ether were added. After 6 hours of stirring, 5 ml of a 1N solution of hydrogen chloride in diethyl ether were added, and stirring was continued at room temperature overnight. A further 10 ml of a 1N solution of hydrogen chloride in diethyl ether were added and stirring at room temperature was continued for a further 24 hours. The precipitated solid was filtered off with suction, washed with diethyl ether and dried under reduced pressure. Since the reaction was still incomplete, the solid was suspended in 10 ml of a 1N solution of hydrogen chloride in diethyl ether and stirred at room temperature for 24 hours. Another 2 ml of a 1N solution of hydrogen chloride in diethyl ether were added, and stirring at room temperature was continued for a further 24 hours. The precipitated solid was filtered off with suction, washed with diethyl ether and dried under reduced pressure. 69 mg (24% of theory) of the target compound were obtained.

$^1$H-NMR (400 MHz, DMSO-$d_6$): δ=9.07 (d, 1H), 8.28 (m, 3H), 7.95 (d, 2H), 7.76 (t, 1H), 7.70 (s, 1H), 7.58 (d, 2H), 7.50 (d, 2H), 7.42-7.18 (m br, 2H), 7.13 (d, 2H), 7.07-6.84 (m br, 2H), 4.70 (s, 2H), 4.50-4.33 (m, 3H), 4.29 (m, 2H), 3.83 (m, 5H), 3.15 (m, 2H), 1.94 (m, 4H), 1.75 (m, 2H), 1.57 (m, 2H), 1.36 (d, 3H).

LC-MS (Method 4): $R_t$=1.18 min; MS (ESIpos): m/z=801 (M+H-2HCl)$^+$.

Example 67

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl 3-amino-L-alanyl-L-alaninate bis(trifluoroacetate)

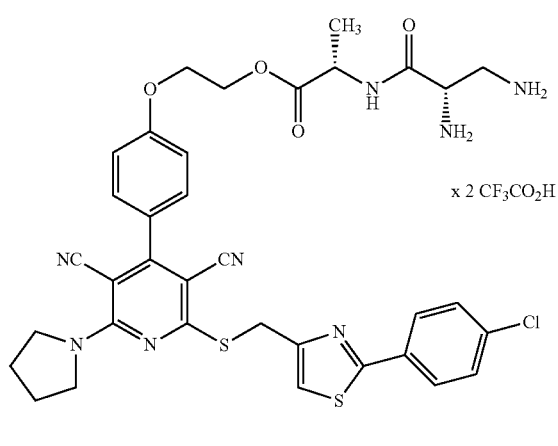 [SMILES: C[C@H](NC(=O)[C@@H](N)CN)C(=O)OCCOc1ccc(-c2c(C#N)c(SCc3csc(-c4ccc(Cl)cc4)n3)nc(N3CCCC3)c2C#N)cc1]

290 mg (0.311 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl N-(tert-butoxycarbonyl)-3-((tert-butoxycarbonyl)amino)-L-alanyl-L-alaninate were dissolved in 5 ml dichloromethane, and 3.113 ml of a 1N solution of hydrogen chloride in diethyl ether were added. After 6 hours of stirring, a further 3.113 ml of a 1N solution of hydrogen chloride in diethyl ether were added and the mixture was stirred at room temperature overnight. Another 10 ml of a 1N solution of hydrogen chloride in diethyl ether were added, and stirring at room temperature was continued for a further 24 hours. The precipitated solid was then filtered off with suction, washed with diethyl ether and dried under reduced pressure. The crude product was dissolved in 2 ml of dichloromethane, and 0.126 ml (1.632 mmol) of trifluoroacetic acid was added. After 6 hours of stirring, the reaction mixture was concentrated and the residue was purified by preparative HPLC (acetonitrile/water+0.1% TFA). 81 mg (27% of theory) of the target compound were obtained.

$^1$H-NMR (400 MHz, DMSO-d$_6$): δ=9.04 (d, 1H), 8.54-8.01 (m br, 6H), 7.94 (d, 2H), 7.70 (s, 1H), 7.58 (d, 2H), 7.50 (d, 2H), 7.13 (d, 2H), 4.70 (s, 2H), 4.53-4.39 (m, 3H), 4.32 (m, 2H), 4.17 (m, 1H), 3.83 (m, 4H), 3.34-3.17 (m, 2H), 1.94 (m, 4H), 1.37 (d, 3H).

LC-MS (Method 4): $R_t$=1.32 min; MS (ESIpos): m/z=731 (M+H-2TFA)$^+$.

Example 68

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl N-(tert-butoxycarbonyl)-L-alanyl-L-leucinate hydrochloride

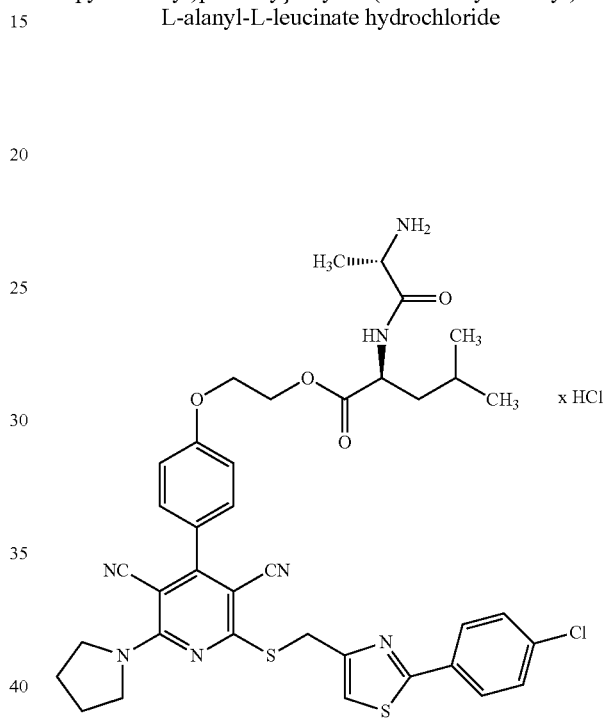

153 mg (0.18 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl N-(tert-butoxycarbonyl)-L-alanyl-L-leucinate were dissolved in 5 ml dichloromethane and 5 ml diethyl ether. 4.5 ml (17.8 mmol) of 4M hydrogen chloride in dioxane were added, and the mixture was stirred at room temperature for 3 h. The precipitate was filtered off, washed with diethyl ether and dried under high vacuum. This gave 68 mg (55. % of theory) of the desired target compound.

$^1$H-NMR (400 MHz, DMSO-d$_6$): δ=8.76 (d, 1H), 8.14 (m, 3H), 7.94 (d, 2H), 7.70 (s, 1H), 7.58 (d, 2H), 7.49 (d, 2H), 7.11 (d, 2H), 4.70 (s, 2H), 4.40-4.27 (m, 4H), 4.01-3.52 (m, 6H), 1.94 (s br, 4H), 1.67 (m, 1H), 1.58 (m, 2H), 1.35 (d, 3H), 0.90 (d, 3H), 0.85 (d, 3H).

LC/MS (Method 2): $R_t$=1.17 min; MS (ESIpos): m/z=758 (M−HCl+H)$^+$.

Example 69

2-{4-(2-({(2-(4-Chlorophenyl)-1,3-thiazol-4-yl)methyl}sulfanyl)-3,5-dicyano-6-(pyrrolidin-1-yl)pyridin-4-yl)phenoxy}ethyl beta-alanyl-L-leucinate hydrochloride

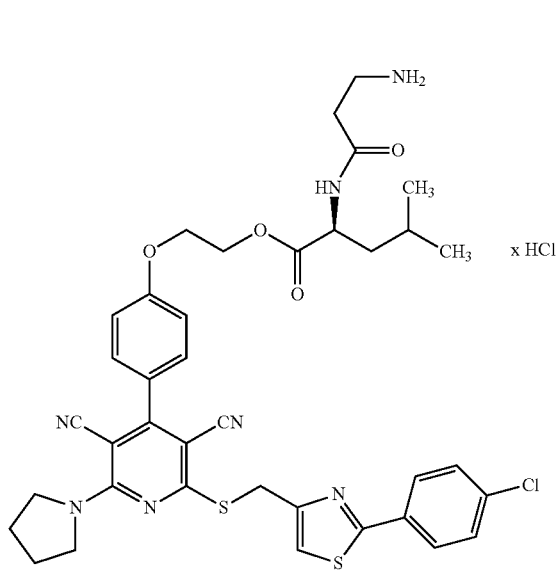 [SMILES: CC(C)C[C@H](NC(=O)CCN)C(=O)OCCOc1ccc(-c2c(C#N)c(SCc3csc(-c4ccc(Cl)cc4)n3)nc(N3CCCC3)c2C#N)cc1]

131 mg (0.15 mmol) of 2-{4-(2-({(2-(4-chlorophenyl)-1,3-thiazol-4-ylmethyl}sulfanyl)-3,5-dicyano-6-(pyrrolidin-1-yl)pyridin-4-yl)phenoxy}ethyl N-(tert-butoxycarbonyl)-L-alanyl-L-leucinate were dissolved in 1.5 ml dichloromethane and 1.5 ml diethyl ether. 3.8 ml (15.2 mmol) of 4M hydrogen chloride in dioxane were added, and the mixture was stirred at room temperature for 3 h. The precipitate was filtered off, washed with diethyl ether and dried under high vacuum. This gave 68 mg (55.% of theory) of the desired target compound.

$^1$H-NMR (400 MHz, DMSO-$d_6$): δ=8.55 (d, 1H), 7.94 (d, 2H), 7.86 (s br, 3H), 7.40 (s, 1H), 7.58 (d, 2H), 7.49 (d, 2H), 7.12 (d, 2H), 4.87 (br s, 2H), 4.70 (s, 2H), 4.42 (m, 2H), 4.30 (m, 3H), 3.85 (s br, 4H), 2.95 (m, 2H), 1.94 (s br, 4H), 1.64 (m, 1H), 1.54 (m, 2H), 0.88 (d, 3H), 0.83 (d, 3H).

LC/MS (Method 2): $R_t$=1.16 min; MS (ESIpos): m/z=758 (M−HCl+H)$^+$.

Example 70

2-{4-(2-({(2-(4-Chlorophenyl)-1,3-thiazol-4-ylmethyl}sulfanyl)-3,5-dicyano-6-(pyrrolidin-1-yl)pyridin-4-yl)phenoxy}ethyl glycyl-L-leucinate hydrochloride

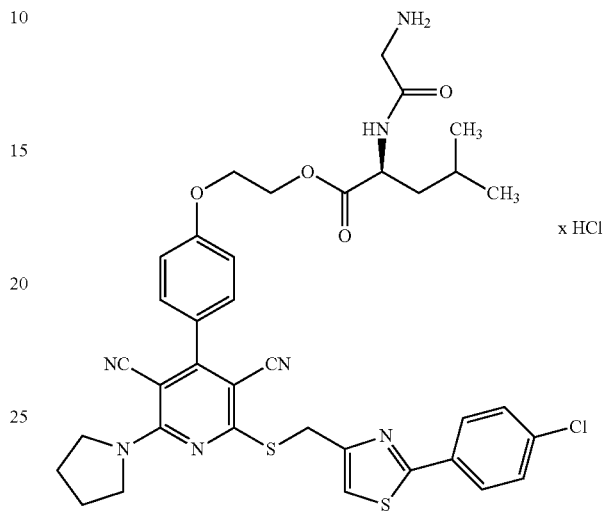

168 mg (0.20 mmol) of 2-{4-(2-({(2-(4-chlorophenyl)-1,3-thiazol-4-yl)methyl}sulfanyl)-3,5-dicyano-6-(pyrrolidin-1-yl)pyridin-4-yl)phenoxy}ethyl N-(tert-butoxycarbonyl)glycyl-L-leucinate were dissolved in 1.5 ml dichloromethane and 1.5 ml diethyl ether. 3.8 ml (15.2 mmol) of 4M hydrogen chloride in dioxane were added, and the mixture was stirred at room temperature for 3 h. The precipitate was filtered off, washed with diethyl ether and dried under high vacuum. This gave 97 mg (60.% of theory) of the desired target compound.

$^1$H-NMR (400 MHz, DMSO-$d_6$): δ=8.84 (d, 1H), 8.10 (m, 3H), 7.94 (d, 2H), 7.70 (s, 1H), 7.58 (d, 2H), 7.49 (d, 2H), 7.12 (d, 2H), 4.70 (s, 2H), 4.41-4.30 (m, 5H), 3.85 (s br, 4H), 3.59 (m, 2H), 1.94 (s br, 4H), 1.75-1.49 (m, 3H), 0.87 (d, 3H), 0.85 (d, 3H).

LC/MS (Method 2): $R_t$=1.16 min; MS (ESIpos): m/z=744 (M−HCl+H)$^+$.

B. ASSESSING THE PHARMACOLOGICAL AND PHYSIOLOGICAL ACTIVITY

The pharmacological and physiological activity of the compounds according to the invention can be demonstrated in the following assays:

B-1. Indirect Determination of the Adenosine Agonism by Way of Gene Expression

Cells of the CHO (Chinese Hamster Ovary) permanent cell line are transfected stably with the cDNA for the adenosine receptor subtypes A1, A2a and A2b. The adenosine A1 receptors are coupled to the adenylate cyclase by way of G, proteins, while the adenosine A2a and A2b receptors are coupled by way of Gs proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance screening:

The stock cultures are grown, at 37° C. and under 5% $CO_2$, in DMEM/F12 medium containing 10% FCS (fetal calf serum) and in each case split 1:10 after 2-3 days. The test cultures are seeded in 384-well plates with 2000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride hexahydrate, 5 mM sodium bicarbonate, pH 7.4). The substances to be tested, which are dissolved in DMSO, are pipetted into the test cultures (maximum final concentration of DMSO in the test mixture: 0.5%) in a dilution series of from $5 \times 10^{-11}$ M to $3 \times 10^{-6}$ M (final concentration). 10 minutes later, forskolin is added to the A1 cells and all the cultures are subsequently incubated at 37° C. for four hours. After that, 35 µl of a solution which is composed of 50% lysis reagent (30 mM disodium hydrogenphosphate, 10% glycerol, 3% TritonX100, 25 mM TrisHCl, 2 mM dithiotreitol (DTT), pH 7.8) and 50% luciferase substrate solution (2.5 mM ATP, 0.5 mM luciferin, 0.1 mM coenzyme A, 10 mM tricine, 1.35 mM magnesium sulfate, 15 mM DTT, pH 7.8) are added to the test cultures, which are shaken for approx. 1 minute and the luciferase activity is measured using a camera system. The ECK values are determined, i.e., the concentrations at which 50% of the luciferase answer is inhibited in the case of the A1 cell, and, respectively, 50% of the maximum stimulation with the corresponding substance is achieved in the case of the A2b and A2a cells. The adenosine-analogous compound NECA (5-N-ethylcarboxamidoadenosine), which binds to all adenosine receptor subtypes with high affinity and possesses an agonistic effect, is used in these experiments as the reference compound (Klotz, K. N., Hessling, J., Hegler, J., Owman, C., Kull, B., Fredholm, B. B., Lohse, M. J., "Comparative pharmacology of human adenosine receptor subtypes—characterization of stably transfected receptors in CHO cells", *Naunyn Schmiedebergs Arch. Pharmacol.*, 357, 1-9 (1998)).

Table 1 below lists the ECK values of representative working examples for the receptor stimulation on adenosine A1, A2a and A2b receptor subtypes:

TABLE 1

| Example No. | $EC_{50}$ A1 (nM) (1 µM forskolin) | $EC_{50}$ A2a (nM) | $EC_{50}$ A2b (nM) |
|---|---|---|---|
| 1 | 0.1 | 673 | 80 |
| 3 | 0.3 | 282 | 138 |
| 5 | 0.5 | 315 | 150 |
| 9 | 0.7 | 281 | 231 |
| 17 | 0.3 | 3000 | 55 |
| 21 | 0.9 | 743 | 3000 |
| 24 | 0.6 | 287 | 675 |
| 26 | 0.5 | 3000 | 1000 |
| 33 | 0.05 | 27 | 900 |

B-2. Studies on Isolated Blood Vessels

The caudal artery of anesthetized rats is excised and mounted in a conventional apparatus for measuring isolated blood vessels. The vessels are perfused in a heated bath and contracted using phenylephrine. The extent of the contraction is determined using a contraction meter. Test substances are added to the precontracted blood vessels, and the reduction of the contraction of the vessels is measured. A reduction of contraction corresponds to a dilation of the vessels. The concentration at which the contraction of the blood vessels is reduced by 50% is given as the $EC_{50}$ value of a test substance with respect to its relaxing properties.

B-3. Measurement of Blood Pressure and Heart Rate on Awake Marmosets

Various concentrations of the test substances are administered orally to awake marmosets which carry an internal transmitter capable of measuring permanently both blood pressure and heart rate (telemetric monitoring of hemodynamic parameters). Blood pressure, heart rate and their changes are then recorded for a period of 6-24 hours.

B-4. Hemodynamic Measurements on Anesthetized Rats:

Wistar rats (body weight 250-300 g; from Harlan-Winkelmann) are anesthetized with 5% Isofluran®. Anesthesia is maintained with 2% Isofluran® and pressurized air in an anesthesia mask. The carotid artery is exposed, and a tip catheter (Millar Micro-Tip transducer, 2 French; from HSE) is inserted and advanced into the left ventricle. A second catheter is then inserted into the jugular vein. Through this catheder, placebo solution and test substance solutions in increasing concentration are infused into the animals. At the same time, the heart function (such as heart rate, left ventricular pressure, contractility (dp/dt), left-ventricular end-diastolic pressure) is measured via the left-ventricular catheter. By withdrawing the catheder from the left ventricle into the aorta, it is also possible to measure the systemic blood pressure.

B-5. Measurement of Blood Pressure and Heart Rate a) On Awake Rats:

Awake spontaneously hypertensive rats (SH-Ratten) carrying an internal transmitter capable of measuring permanently both blood pressure and heart rate (telemetric monitoring of hemodynamic parameters) and sitting in a cage fitted with motion sensors are orally administered test substances in various dosages. Blood pressure and heart rate and changes thereof, and also the movements and the activity of the animals are then recorded and evaluated for 24 hours.

Table 2 shows the maximum reduction in heart rate following oral administration of 3 mg/kg of the compound from Example 1 or Example 2 or Example 41:

TABLE 2

| Example No. | Dosage | Heart rate reduction |
|---|---|---|
| 1 | 3 mg/kg | −20% |
| 2 | 3 mg/kg | −45% |
| 41 | 3 mg/kg | −5% |
| 44 | 3 mg/kg | −20% |
| 63 | 3 mg/kg | −20% | b) On Awake Dogs:

Awake male Beagle dogs carrying an internal transmitter capable of measuring permanently both blood pressure and heart rate (telemetric monitoring of hemodynamic parameters) are administered test substances in various dosages orally or intraduodenally. Blood pressure and heart rate and changes thereof are then recorded and evaluated for 24 hours. At the same time, the behavior of the animals with respect to their activity (gait, side position, rest phases etc.) is observed to obtain indications of a possible CNS action of the substances.

B-6. GTP Shift Experiment

Preparation of the Brain Membrane

The brains of male Wistar rats are removed and immediately transferred into an ice-cooled 0.32 mol/l sucrose solution. The tissue is comminuted using a glass-Teflon homogenizer and then centrifuged (1000×g for 10 minutes). The supernatant is then ultracentrifuged at 30 000 g for 30 minutes. The pellet obtained in this manner is resuspended in 10 ml of water and allowed to stand on ice for 30 minutes. After a final centrifugation step at 48 000 g for 10 min, the membranes are resuspended in 50 mmol/l Tris-HCl buffer, pH 7.4, and incubated with 2 U/ml of adenosine deaminase at 37° C. for 30 min. This is followed by a protein determination according to Bradford. The membranes are frozen in small aliquots and stored at −80° C. until required for the binding assay.

Receptor Binding Study

The A1 receptor GTP shift binding assay is carried out using rat brain membranes and 0.4 nM ($^3$H) DPCPX ($K_d$=0.28 nM) as radioligand. 10 µg of membrane protein are incubated at 37° C. for 20 min with 0.4 nM ($^3$H)DPCPX and adenosine A1 agonists in various concentrations in buffer (50 mM tris-HCl, pH 7.4, 2 U/ml ADA) in the presence and absence of 1 mM guanosine triphosphate (GTP). The incubation is terminated by filtration through GF/B glass fiber filter plates. The filters are then washed three times with ice-cold tris-HCl buffer 50 mM, pH 7.4. The radioactivity on the filter is measured with addition of 100 it of scintillation cocktail in a Microbeta TriLux beta counter (PerkinElmer, Massachusetts, USA).

B-7. Test of Adenosine A1 Receptor Agonists on Locomotor Action in the Treadmill Experiment To determine the action of adenosine A1 receptor agonists on locomotor function, the running behavior of mice (strain: CD1) in treadmills (M. Weber et al., Psychopharmacology 2008, in print) is examined. To get the mice accustomed to voluntary use of the treadmill, 2-3 weeks prior to the start of the experiment the animals are isolated in cages with a treadmill and trained. 2 weeks prior to the start of the experiment, the movements of the mice in the treadmill are recorded by a photo cell using a computer, and various running parameters such as, for example, the distance run in a day, the individual distances covered, and also their distribution over the day are determined. According to their natural running behavior, the animals are randomized into groups (8-12 animals) (control group and 1—a plurality of substance groups). After the initial 2-week phase, the animals are treated orally with the substances to be tested. Here, single doses or else increasing dosages (for example 0.3-1-3-10-30 mg/kg) are administered. The substances are tested in two independent experiments. Between 2 experiments, there are at least 3 days where the animals are not administered any substances. The running behavior of the animals is observed and recorded for 24 hours after administration. Evaluation of the running intervals and the total distance covered takes place over a period of several hours during the main activity period of the mice. Effects are stated in percent of the control.

| Example No. | Reduction of the total distance run by 1 mg/kg |
|---|---|
| 1 | 0% |
| 13 | 0% |
| 21 | 7.5% |
| 33 | 24% |

B-8. Determination of Solubility, Stability and Liberation Behavior a) Determination of the Solubility:

The test substance is suspended in 5% strength aqueous dextrose solution. This suspension is shaken at room temperature for 24 h. After ultracentrifugation at 224 000 g for 30 min, the supernatant is diluted with DMSO and analyzed by HPLC. A two-point calibration plot of the test compound in DMSO is used for quantification.

HPLC Method for Acids:

Agilent 1100 with DAD (G1315A), quat. pump (G1311A), autosampler CTC HTS PAL, degasser (G1322A) and column thermostat (G1316A); column: Phenomenex Gemini C18, 5 µm, 50 mm×2 mm; temperature: 40° C.; eluent A: water/phosphoric acid pH 2; eluent B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 3.5 µm, 60 mm×2.1 mm; temperature: 30° C.; eluent A: water+5 ml perchloric acid/l; eluent B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

The solubilities of representative exemplary embodiments in 5% strength aqueous dextrose solution are shown in Table 1:

TABLE 1

| Example No. | Solubility (mg/liter) |
|---|---|
| 41 | 650 |
| 44 | 410 |
| 51 | 540 |
| 52 | 280 |
| 54 | 640 |
| 58 | 470 |

No decomposition of the exemplary compounds in these solutions was observed.

The solubility of the active substance from Example 1, Example 2 and Example 12 is below the detection limit.

b) Stability in Buffer at Various pH Values:

0.3 mg of the test substance is weighed into a 2 ml HPLC vial and 0.5 ml of acetonitrile or acetonitrile/DMSO (9:1) is added. The substance is dissolved by putting the sample vessel in an ultrasonic bath for about 10 seconds. Then 0.5 ml of the respective (buffer) solution is added, and the sample is again treated in the ultrasonic bath.

(Buffer) solutions employed:

pH 2: 0.03 mol of citric acid, 0.061 mol of sodium chloride and 0.0082 mol of hydrochoric acid ad 1 liter of water;

pH 4: 1 liter of Millipore water is adjusted to pH 4.0 with 1 N hydrochloric acid;

pH 5: 0.096 mol of citric acid and 0.2 mol of sodium hydroxide ad 1 liter of water;

pH 6: 0.06 mol of citric acid and 0.16 mol of sodium hydroxide ad 1 liter of water;

pH 7.4: 90.0 g of sodium chloride, 13.61 g of potassium dihydrogen phosphate and 83.35 g of 1 N sodium hydroxide solution are made up to 1 liter with water; this solution is then further diluted 1:10 with Millipore water.

pH 8: 0.013 mol of borax and 0.021 mol of hydrochloric acid ad 1 liter of water.

5 µl portions of the test solution are analyzed by HPLC for their content of unchanged test substance, and of active substance (A) produced, every hour over a period of 24 hours at 37° C. The percentage areas of the appropriate peaks are used for quantification.

HPLC method for Examples 41 and 44:

Agilent 1100 with DAD (G1315B), binary pump (G1312A), autosampler (G1329A), column oven (G1316A), thermostat (G1330B); column: Kromasil 100 C18, 250 mm×4 mm, 5 µm; column temperature: 30° C.; mobile phase A: water+5 ml of perchloric acid/liter, eluent B: acetonitrile; gradient: 0 min 90% A→5.0 min 40% A→18.0 min 10% A→19.0 min 10% A→21.0 min 90% A→23.0 min 90% A; flow rate: 2.0 ml/min; UV detection: 288 nm.

HPLC Method for Examples 50 and 59:

Agilent 1100 with DAD (G1315B), binary pump (G1312A), autosampler (G1329A), column oven (G1316A), thermostat (G1330B); column: Kromasil 100 C18, 125 mm×4 mm, 5 µm; column temperature: 30° C.; mobile phase A: water+5 ml of perchloric acid/liter, eluent B: acetonitrile; gradient: 0 min 90% A→5.0 min 60% A→7.0 min 60% A→10.0 min 10% A→12.0 min 10% A→14.0 min 90% A→16.0 min 90% A; flow rate: 2.0 ml/min; UV detection: 294 nm.

HPLC Method for Example 54:

Agilent 1100 with DAD (G1314A), binary pump (G1312A), autosampler (G1329A), column oven (G1316A), thermostat (G1330A); column: Kromasil 100 C18, 250 mm×4 mm, 5 µm; column temperature: 30° C.; mobile phase A: water+5 ml of perchloric acid/liter, eluent B: acetonitrile; gradient: 0 min 90% A→5.0 min 40% A→18.0 min 10% A→19.0 min 10% A→21.0 min 90% A→23.0 min 90% A; flow rate: 2.0 ml/min; UV detection: 288 nm.

The ratios of the peak areas (F) at the respective time points in relation to the peak areas at the starting time are shown in Table 2 for representative exemplary embodiments:

TABLE 2

| Example No. | pH | % test substance after 4 h (F(t = 4 h) × 100/ F(t = 0 h)) | % test substance after 24 h (F(t = 24 h) × 100/ F(t = 0 h)) |
| --- | --- | --- | --- |
| 41 | 4 | 97 | 99 |
| 41 | 7.4 | 37 | 0 |
| 44 | 4 | 99 | 99 |
| 44 | 7.4 | 78 | 26 |
| 50 | 4 | 99 | 99 |
| 50 | 7.4 | 94 | 78 |
| 54 | 4 | 98 | 97 |
| 54 | 7.4 | 29 | 0 |
| 59 | 4 | 99 | 95 |
| 59 | 7.4 | 0 | 0 |
| 63 | 4 | 98 | 98 |
| 63 | 7.4 | 93 | 67 |

In this test there was found to be a decrease in the content of test substance at the same time as an increase in the active ingredient compound from Example 1 or 12.

c) Stability in Suspension and as Solid:

4.7-4.8 g of the test substance are suspended in 200 ml of isopropanol and stirred at room temperature for 7 days. The solid is filtered off and air-dried at room temperature for 3 days. LC/MS (Method 2) is then used to measure whether there has been a degradation of the test substance. Examples 63 and 44 showed no degradation.

To assess the stability of the solids, 20 mg of the solids obtained in this manner are stored in a sealed Head-Space vial at 90° C. in a drying cabinet without vacuum for 7 days. HPLC is then used to measure whether there has been a degradation of the test substance.

HPLC Method for Measuring the Stability of the Solid of Example 63:

Instrument: Agilent 1100 or comparable instrument, UV variable wavelength (for example diode array); wavelength measured: 215 nm, band width 6 nm; reference wavelength: switched off; oven temperature: 40° C.; column: Nucleodur Gravity C18, length 150 mm, internal diameter 2.0 mm, particle size 3 µm; mobile phase: A acidic ammonium phosphate buffer (pH 2.4), B acetonitrile; analysis program: flow rate 0.25 ml/min, start 0 min 85% A→35 min 20% A→stop 45 min 20% A; equilibration: 12 min; sample solution: about 25 mg of the sample are weighed out accurately into a 50 ml measuring flask, dissolved in 25 ml of isopropanol and made up with water to the calibration mark; calibration solution: about 25 mg of the standard are weighed out accurately into a 50 ml measuring flask, dissolved in 25 ml of isopropanol and made up with water to the calibration mark; injection volume: 3 µl.

HPLC Method for Measuring the Stability of the Solid of Example 44:

Instrument: Agilent 1100 or comparable instrument, UV variable wavelength (for example diode array); wavelength measured: 220 nm, band width 6 nm; reference wavelength: switched off; oven temperature: 45° C.; column: Zorbax SB-CN, length 150 mm, internal diameter 3.0 mm, particle size 3.5 µm; mobile phase: neutral ammonium phosphate buffer (pH 7.2), B acetonitrile; analysis program: flow rate 0.5 ml/min, start 0 min 80% A→25 min 20% A→stop 35 min 20% A; equilibration: 10 min; sample solution: about 22 mg of the sample are weighed out accurately into a 50 ml measuring flask, dissolved in 25 ml of acetonitrile and made up with water to the calibration mark; calibration solution: about 25 mg of the standard are weighed out accurately into a 50 ml measuring flask, dissolved in 25 ml of acetonitrile and made up with water to the calibration mark; injection volume: 3 µl.

Within the accuracy of measurement, Examples 63 and 44 showed no degradation.

d) In Vitro Stability in Rat and Human Plasma:

1 mg of the test substance is weighed into a 2 ml HPLC vial, and 1.5 ml of DMSO and 1 ml of water are added. The substance is dissolved by placing the sample vessel in an ultrasonic bath for about 10 seconds. 0.5 ml of rat or human plasma at 37° C. is added to 0.5 ml of this solution. The sample is shaken, and about 10 µl are removed for a first analysis (time point to). 4-6 further aliquots are removed for quantification in the period up to 2 hours after the start of incubation. The sample is kept at 37° C. during the time of the test. Characterization and quantification take place by HPLC.

HPLC Method:

Agilent 1100 with DAD (G1314A), binary pump (G1312A), autosampler (G1329A), column oven (G1316A), thermostat (G1330A); column: Kromasil 100 C18, 250 mm×4 mm, 5 µm; column temperature: 30° C.; eluent A: water+5 ml of perchloric acid/liter, eluent B: acetonitrile; gradient: 0-8.0 min 53% A, 47% B; 8.0-18.0 min 53% A, 47% B; 18.0-20.0 min 90% A, 10% B; 20.0-21.0 min 90% A, 10% B; 21.0-22.5 min 98% A, 2% B; 22.5-25.0 min 98% A, 2% B; flow rate: 2 ml/min; UV detection: 294 nm.

e) i.v. Pharmacokinetics in Wistar Rats:

On the day before administration of the substance, a catheter for obtaining blood is implanted in the jugular vein of the experimental animals (male Wistar rats, body weight 200-250 g) under Isofluran® anesthesia.

On the day of the experiment, a defined dose of the test substance is administered as solution into the tail vein using a Hamilton® glass syringe (bolus administration, duration of administration<10 s). Blood samples (8-12 time points) are taken through the catheter sequentially over the course of 24 h after administration of the substance. Plasma is obtained by centrifuging the samples in heparinized tubes. Acetonitrile is added to a defined plasma volume per time point to precipitate proteins. After centrifugation, test substance and, where appropriate, known cleavage products of the test substance in the supernatant are determined quantitatively using a suitable LC/MS-MS method.

The measured plasma concentrations are used to calculate pharmacokinetic parameters of the test substance and of the active ingredient compound (A) liberated therefrom, such as AUC, $C_{max}$, $T_{1/2}$ (half-life) and CL (clearance).

After i.v. administration of the compounds from Example 63, 44 or 41, these substances were no longer detectable in plasma even at the first measurement point. Only the active ingredient (Example 1) was detectable up to the 24-hour time point too.

f) Oral Pharmacokinetics in Wistar Rats:

On the day before administration of the substance, a catheter for obtaining blood is implanted in the jugular vein of the experimental animals (male Wistar rats, body weight 200-250 g) under Isofluran® anesthesia.

On the day of the experiment, a defined dose of the test substance is administered as solution into the stomach by gavage. Blood samples (8-12 time points) are taken through the catheter sequentially over the course of 24 h after administration of the substance. Plasma is obtained by centrifuging the samples in heparinized tubes. Acetonitrile is added to a defined plasma volume per time point to precipitate proteins. After centrifugation, test substance and, where appropriate, known cleavage products of the test substance in the supernatant are determined quantitatively using a suitable LC/MS-MS method.

The measured plasma concentrations are used to calculate pharmacokinetic parameters of the test substance and of the active ingredient compound (A) liberated therefrom, such as AUC, $C_{max}$ and $T_{1/2}$ (half-life).

After oral administration of the compounds from Example 63, 44 or 41, these substances were no longer detectable in plasma even at the first measurement point. Only the active ingredient (Example 1) was detectable up to the 24-hour time point too.

B-9. Determination of the Metabolic Stability

To determine the metabolic stability of test compounds, the latter are incubated in vitro with liver microsomes or, preferably, with primary fresh hepatocytes of various animal species (for example from rat and dog) and also of human origin to obtain and to compare metabolite profiles of a hepatic phase I and phase II metabolism which is as complete as possible.

The test compounds are incubated at a concentration of 10-20 µM. To this end, stock solutions of the substances with a concentration of 1-2 mM are prepared in acetonitrile and then pipetted with a 1:100 dilution into the incubation mixture. The liver microsomes are incubated in 50 mM potassium phosphate buffer (pH 7.4) with and without NADPH-generating system consisting of 1 mM $NADP^+$, 10 mM glucose 6-phosphate and 1 unit of glucose 6-phosphate dehydrogenase, at 37° C. Primary hepatocytes are also incubated at 37° C. in suspension in Williams E medium. After an incubation time of 0-4 hours, the incubation mixtures are stopped with acetonitrile (final concentration about 30%), and the protein is removed by centrifugation at about 15 000×g. The samples stopped in this way are either analyzed directly or stored at −20° C. until analyzed.

The analysis takes place by high performance liquid chromatography with ultraviolet and mass spectrometry detection (HPLC-UV-MS/MS). To this end, the supernatants of the incubation samples are chromatographed using suitable C18 reversed-phase columns and variable mobile phase mixtures of acetonitrile and 10 mM aqueous ammonium formate solution. The UV chromatograms in combination with mass-spectrometric MS/MS data serve to identify the metabolites and to elucidate their structures.

B-10. CYP Inhibition Assay

The ability of substances to inhibit CYP1A2, CYP 2C8, CYP2C9, CYP2D6 and CYP3A4 in humans is investigated with pooled human liver microsomes as enzyme source in the presence of standard substrates (see below) which form CYP-isoform-specific metabolites. The inhibitory effects are investigated with six different concentrations of the test compounds (0.6, 1.3, 2.5, 5, and 20 µM or 1.5, 3.1, 6.3, 12.5, 25 and 50 µM), compared with the extent of the CYP-isoform-specific metabolite formation of the standard substrates in the absence of the test compounds, and the corresponding 1050 values are calculated. A standard inhibitor which specifically inhibits a single CYP isoform serves as control of the results obtained.

Procedure:

Incubation of phenacetin, amodiaquin, diclofenac, dextromethorphan or midazolam with human liver microsomes in the presence of in each case six different concentrations of a test compound (as potential inhibitor) is carried out on a work station (Tecan, Genesis, Crailsheim, Germany). Standard incubation mixtures comprise 1.0 mM NADP, 1.0 mM EDTA, 5.0 mM glucose 6-phosphate, glucose 6-phosphate dehydrogenase (1.5 U/ml) and 50 mM phosphate buffer (pH 7.4) in a total volume of 200 µl. Test compounds are preferably dissolved in acetonitrile. 96-well plates are incubated with pooled human liver microsomes at 37° C. for a defined time. The reactions are stopped by adding 100 µl of acetonitrile in which a suitable internal standard is always present. Precipitated proteins are removed by centrifugation, and the supernatants are combined and analyzed by LC-MS/MS.

With the CYP isoenzymes 1A2, 2C8, 2C9, 2D6, 3A4 and 3A4, the compounds from Examples 1, 13, 19, 6, 27, 10, 26, 8, 14 and 29 show, after a preincubation of 30 minutes, an $IC_{50}/K_i$ value of >20 µM.

B-11. Determination of Pharmacokinetic Parameters after Intravenous and Oral Administration The substance to be tested is administered intravenously as a solution to animals (for example mice, rats, dogs), and oral administration takes place as solution or suspension by gavage. After administration of the substance, blood is taken from the animals at fixed times and is heparinized, and then plasma is obtained therefrom by centrifugation. The substance is quantified analytically in the plasma by LC/MS-MS. The plasma concentration/time courses found in this way are used to calculate the pharmacokinetic parameters such as AUC (area under the concentration, $C_{max}$ time curve), $T_{1/2}$ (half-life) and CL (clearance) by means of a validated pharmacokinetic computer program.

B-12. Determination of the Free Plasma Fraction with Transil

The distribution (maximum plasma concentration) of a compound between, firstly, water and surface-supported egg lecithin membranes (Transil) ($MA_{buffer}$) and, secondly, between plasma and surface-supported egg lecithin membranes (Transil) ($MA_{plasma}$) is measured.

The dissolved test substance is pipetted to suspensions of Transil/buffer and Transil/plasma. After these incubations, the Transil is separated from the respective phase by centrifugation at 1800 g. The substance concentrations before the centrifugation and in the supernatant after the centrifugation are determined. The free fraction is calculated as the ratio of the membrane affinity in the plasma ($MA_{plasma}$) and in the buffer ($MA_{buffer}$).

B-13. CNS Action of Substances

Possible effects of a single oral administration of a test substance on behavior parameters, locomotor activity ("open field test") and body temperature are investigated in rats. The test substances are administered orally in increasing dosage. Control animals receive only the vehicle (ethanol/Solutol/water (10:40:50, v/v/v). Each treatment group consists of 6 male rats. The animals are examined for changes in their behavior and in body temperature after 0.5, 1, 2 and 7 hours. After about 0.5 and 7 hours, the animals are also examined for possible substance-related changes in their locomotor activity in the "open field test" (free movement in the cage). Plasma concentrations of the test substances are determined in satellite groups.

C. EXEMPLARY EMBODIMENTS OF PHARMACEUTICAL COMPOSITIONS

The compounds of the invention can be converted into pharmaceutical preparations in the following ways:

Tablet:
Composition:
100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:
The mixture of compound of the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:
The Rhodigel is suspended in ethanol, and the compound of the invention is added to the suspension. The water is added while stirring. The mixture is stirred for about 6 h until the swelling of the Rhodigel is complete.

Solution which can be Administered Orally:
Composition:
500 mg of the compound of the invention, 2.5 g of polysorbate and 97 g of polyethylene glycol 400.20 g of oral solution correspond to a single dose of 100 mg of the compound of the invention.

Production:
The compound of the invention is suspended in the mixture of polyethylene glycol and polysorbate with stirring. The stirring process is continued until the compound of the invention has completely dissolved.

i.v. Solution:
The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

What is claimed is:
1. A compound of formula (VII)

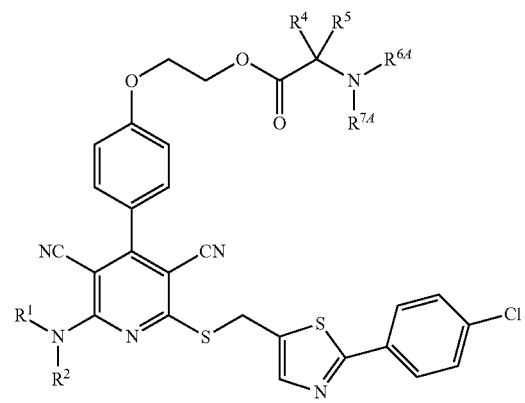

(VII)

or wherein,
$R^1$ represents hydrogen or ($C_1$-$C_4$)-alkyl,
$R^2$ represents ($C_1$-$C_6$)-alkyl, ($C_2$-$C_4$)-alkenyl, ($C_2$-$C_4$)-alkynyl or ($C_3$-$C_7$)-cycloalkyl,
where ($C_1$-$C_6$)-alkyl may be substituted by 1 to 3 substituents selected independently of one another from the group consisting of fluorine, chlorine, trifluoromethyl, trifluoromethoxy, ($C_1$-$C_4$)-alkoxy, ($C_3$-$C_7$)-cycloalkyl, ($C_3$-$C_7$)-cycloalkoxy, ($C_1$-$C_4$)-alkylsulfanyl and ($C_1$-$C_4$)-alkylsulfonyl,
and
where ($C_2$-$C_4$)-alkenyl and ($C_2$-$C_4$)-alkynyl may be substituted by 1 or 2 substituents selected independently of one another from the group consisting of fluorine, trifluoromethyl, ($C_1$-$C_4$)-alkyl, trifluoromethoxy and ($C_1$-$C_4$)-alkoxy,
and
where ($C_3$-$C_7$)-cycloalkyl may be substituted by 1 or 2 substituents selected independently of one another from the group consisting of fluorine, chlorine, trifluoromethyl, ($C_1$-$C_4$)-alkyl, trifluoromethoxy and ($C_1$-$C_4$)-alkoxy,
or
$R^1$ and $R^2$ together with the nitrogen atom to which they are attached form a 4- to 7-membered heterocycle which may contain a further heteroatom from the group consisting of N, O and S,
where the 4- to 7-membered heterocycle may be substituted by 1 or 2 substituents selected independently of one another from the group consisting of fluorine, chlorine, oxo, trifluoromethyl, ($C_1$-$C_4$)-alkyl, trifluoromethoxy and ($C_1$-$C_4$)-alkoxy,
$R^4$ represents hydrogen or the side group of a natural α-amino acid or its homologs or isomers,
$R^5$ represents hydrogen or methyl, $R^{6A}$ represents hydrogen, $(C_1-C_4)$-alkyl, or an amino protective group, $R^{7A}$ represents hydrogen, $(C_1-C_4)$-alkyl, or an amino protective group, or $R^{6A}$ and $R^{7A}$ together with the nitrogen atom to which they are attached form a 5- or 6-membered heterocycle, where the 5- or 6-membered heterocycle may be substituted by 1 or 2 substituents independently selected from the group consisting of $(C_1-C_4)$-alkyl, amino, hydroxyl and $(C_1-C_4)$-alkoxy, or $R^{7A}$ together with $R^4$ and the atoms, to which they are attached, forms a pyrrolidine or piperidine ring, or a salt thereof.

2. The compound of claim 1, wherein $R^1$ represents hydrogen, methyl, or ethyl;

$R^2$ represents $(C_1-C_3)$-alkyl, cyclopropyl, or cyclobutyl, where $(C_1-C_3)$-alkyl may be substituted by 1 or 2 substituents selected independently of one another from the group consisting of fluorine, chlorine, trifluoromethyl, methoxy, ethoxy, cyclopropyl, and cyclobutyl;

or $R^1$ and $R^2$ together with the nitrogen atom to which they are attached form a 4- to 6-membered heterocycle which may contain a further heteroatom from the group consisting of N, O, and S, where the 4- to 6-membered heterocycle may be substituted by 1 or 2 substituents selected independently of one another from the group consisting of fluorine, trifluoromethyl, methyl, ethyl, methoxy, and ethoxy;

$R^4$ represents methyl or 3-aminopropan-1-yl;

$R^5$ represents hydrogen;

$R^{6A}$ represents hydrogen, methyl, or an amino protecting group; and $R^{7A}$ represents hydrogen, or an amino protecting group; or $R^{7A}$ together with $R^4$ and the atoms, to which they are attached, forms a pyrrolidine ring.

3. The compound of claim 1, wherein $R^1$ represents hydrogen, methyl, or ethyl;

$R^2$ represents methyl, ethyl, or n-propyl, where methyl, ethyl, and n-propyl may be substituted by 1 or 2 substituents selected independently of one another from the group consisting of fluorine, trifluoromethyl, and methoxy;

or $R^1$ and $R^2$ together with the nitrogen atom to which they are attached form an azetidinyl, pyrrolidinyl, or piperidinyl ring, where the azetidinyl, and piperidinyl ring may be substituted by a methoxy substituent.

4. The compound of claim 1, wherein $R^1$ represents hydrogen, methyl or ethyl, $R^2$ represents $(C_1-C_3)$-alkyl, cyclopropyl or cyclobutyl, where $(C_1-C_3)$-alkyl may be substituted by 1 or 2 substituents selected independently of one another from the group consisting of fluorine, chlorine, trifluoromethyl, methoxy, ethoxy, cyclopropyl and cyclobutyl.

5. A compound of formula (VIII)

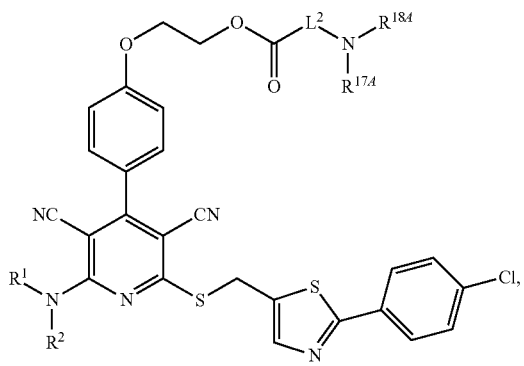

(VIII)

wherein $R^1$ represents hydrogen or $(C_1-C_4)$-alkyl, $R^2$ represents $(C_1-C_6)$-alkyl, $(C_2-C_4)$-alkenyl, $(C_2-C_4)$-alkynyl or $(C_3-C_7)$-cycloalkyl, where $(C_1-C_6)$-alkyl may be substituted by 1 to 3 substituents selected independently of one another from the group consisting of fluorine, chlorine, trifluoromethyl, trifluoromethoxy, $(C_1-C_4)$-alkoxy, $(C_3-C_7)$-cycloalkyl, $(C_3-C_7)$-cycloalkoxy, $(C_1-C_4)$-alkylsulfanyl and $(C_1-C_4)$-alkylsulfonyl, where $(C_2-C_4)$-alkenyl and $(C_2-C_4)$-alkynyl may be substituted by 1 or 2 substituents selected independently of one another from the group consisting of fluorine, trifluoromethyl, $(C_1-C_4)$-alkyl, trifluoromethoxy and $(C_1-C_4)$-alkoxy, and where $(C_3-C_7)$-cycloalkyl may be substituted by 1 or 2 substituents selected independently of one another from the group consisting of fluorine, chlorine, trifluoromethyl, $(C_1-C_4)$-alkyl, trifluoromethoxy and $(C_1-C_4)$-alkoxy, or $R^1$ and $R^2$ together with the nitrogen atom to which they are attached form a 4- to 7-membered heterocycle which may contain a further heteroatom from the group consisting of N, O and S, where the 4- to 7-membered heterocycle may be substituted by 1 or 2 substituents selected independently of one another from the group consisting of fluorine, chlorine, oxo, trifluoromethyl, $(C_1-C_4)$-alkyl, trifluoromethoxy and $(C_1-C_4)$-alkoxy;

$L^2$ represents $(C_2-C_6)$-alkanediyl;

$R^{17A}$ represents hydrogen, $(C_1-C_4)$-alkyl, or an amino protective group, and $R^{18A}$ represents hydrogen, $(C_1-C_4)$-alkyl, or an amino protective group; or $R^{17}$ and $R^{18}$ together with the nitrogen atom to which they are attached form a 5- or 6-membered heterocycle, where the 5- or 6-membered heterocycle may be substituted by 1 or 2 substituents independently selected from the group consisting of $(C_1-C_4)$-alkyl, amino, hydroxyl, and $(C_1-C_4)$-alkoxy.

6. The compound of claim 5, wherein $R^1$ represents hydrogen, methyl, or ethyl;

$R^2$ represents $(C_1-C_3)$-alkyl, cyclopropyl, or cyclobutyl, where $(C_1-C_3)$-alkyl may be substituted by 1 or 2 substituents selected independently of one another from the group consisting of fluorine, chlorine, trifluoromethyl, methoxy, ethoxy, cyclopropyl, and cyclobutyl;

or

R$^1$ and R$^2$ together with the nitrogen atom to which they are attached form a 4- to 6-membered heterocycle which may contain a further heteroatom from the group consisting of N, O, and S,
  where the 4- to 6-membered heterocycle may be substituted by 1 or 2 substituents selected independently of one another from the group consisting of fluorine, trifluoromethyl, methyl, ethyl, methoxy, and ethoxy;

L$^2$ represents ethane-1,2-diyl or propane-1,3-diyl,

R$^{17}$ represents hydrogen, methyl, or an amino protecting group; and

R$^{18}$ represents hydrogen, methyl, or an amino protecting group.

7. The compound of claim 5, wherein

R$^1$ represents hydrogen, methyl, or ethyl;

R$^2$ represents methyl, ethyl, or n-propyl, where methyl, ethyl, and n-propyl may be substituted by 1 or 2 substituents selected independently of one another from the group consisting of fluorine, trifluoromethyl, and methoxy;

or

R$^1$ and R$^2$ together with the nitrogen atom to which they are attached form an azetidinyl, pyrrolidinyl, or piperidinyl ring, where the azetidinyl, and piperidinyl ring may be substituted by a methoxy substituent.

* * * * *